US008623196B2

(12) United States Patent

Kohli et al.

(10) Patent No.: US 8,623,196 B2

(45) Date of Patent: Jan. 7, 2014

(54) NANOSTRUCTURED BIOSENSOR CONTAINING NEUROPATHY TARGET ESTERASE ACTIVITY

(75) Inventors: Neeraj Kohli, Cambridge, MA (US); Devesh Srivastava, East Lansing, MI (US); Rudy J. Richardson, Ann Arbor, MI (US); Jun Sun, Hockessin, DE (US); Ilsoon Lee, Okemos, MI (US); Robert M. Worden, Holt, MI (US)

(73) Assignees: Michigan State University, East Lansing, MI (US); The Regents of the University of Michigan, Ann Arbor, MI (US)

( * ) Notice: Subject to any disclaimer, the term of this patent is extended or adjusted under 35 U.S.C. 154(b) by 1496 days.

(21) Appl. No.: 12/121,389

(22) Filed: May 15, 2008

(65) Prior Publication Data

US 2012/0160708 A1 Jun. 28, 2012

Related U.S. Application Data

(60) Provisional application No. 60/930,465, filed on May 16, 2007.

(51) Int. Cl.
*G01N 27/327* (2006.01)

(52) U.S. Cl.
USPC ................ 205/777.5; 204/403.04; 204/403.14

(58) Field of Classification Search
USPC ............. 204/403.01–403.15; 205/777.5, 778, 205/792
See application file for complete search history.

(56) References Cited

FOREIGN PATENT DOCUMENTS

| | | | | |
|---|---|---|---|---|
| JP | 07-103933 A | * | 4/1995 | ........... G01N 27/327 |
| JP | 2005-83965 A | * | 3/2005 | ........... G01N 27/327 |

OTHER PUBLICATIONS

Mizutani et al. “Enzyme electrodes based on self-assembled monolayers of thiol compounds on gold,” Electrochimica Acta 44 (1999) 3833-3838.*

JPO computer-generated English language translation of the Claims section and Detailed Description section of Hayashi et al. JP 2005-083965 A.*

JPO computer-generated English language translation of the Claims section and Detailed Description section of Yamamoto et al. JP 07-103933 A.*

Taira et al. “Preparation of Enzyme Electrode Based on Self-assembly of Redox Active Polymer and Polyion Complex Formation,” Electrochemistry (Tokyo, Japan) (2001), 69(12), 940-941.*

Akram et al. “Direct application strategy to immobilize a thiotic acid self-assembled monolayer on a gold electrode” Analytica Chimica Acta 504 (2004) 243-251.*

Campanella et al. “Organophosphorus and carbamate pesticide analysis using an inhibition tyrosinase organic phase enzyme sensor; comparison by butyrylcholinesterase + choline oxidase opee and application to natural waters,” Analytica Chimica Acta 587 (2007, available online Jan. 19, 2007) 22-32.*

Sokolovskaya et al. “Improved electrochemical analysis of neuropathy target esterase activity by a tyrosinase carbon paste electrode modified by 1-methoxyphenazine methosulfate,” Biotechnol. Lett. Aug. 27, 2005 (16):1211-8.*

* cited by examiner

*Primary Examiner* — Alex Noguerola

(74) *Attorney, Agent, or Firm* — Schwegman Lundberg & Woessner, P.A.

(57) ABSTRACT

The present invention provides compositions, devices and methods for detecting esterase activity. The present invention also provides devices and methods of detecting esterase inhibitors, for example, organophosphates. In particular, the present invention provides a biosensor comprising Neuropathy Target Esterase (NTE) polypeptides. Further, the present invention relates to medicine, industrial chemistry, agriculture, and homeland security.

21 Claims, 36 Drawing Sheets

Neuropathy target esterase (NTE): Integral membrane protein in vertebrate neurons

Glynn, Biochem. J. (1999) 344:625-631; herein incorporated by reference.

NEST

- In one example, NEST comprises residues 727-1216 of NTE.
- In one example, a Molecular mass of NEST is approximately 47 kDa.

Immobilization of Tyrosinase

Figure 3B Immobilization of enzyme, ex. Tyrosinase
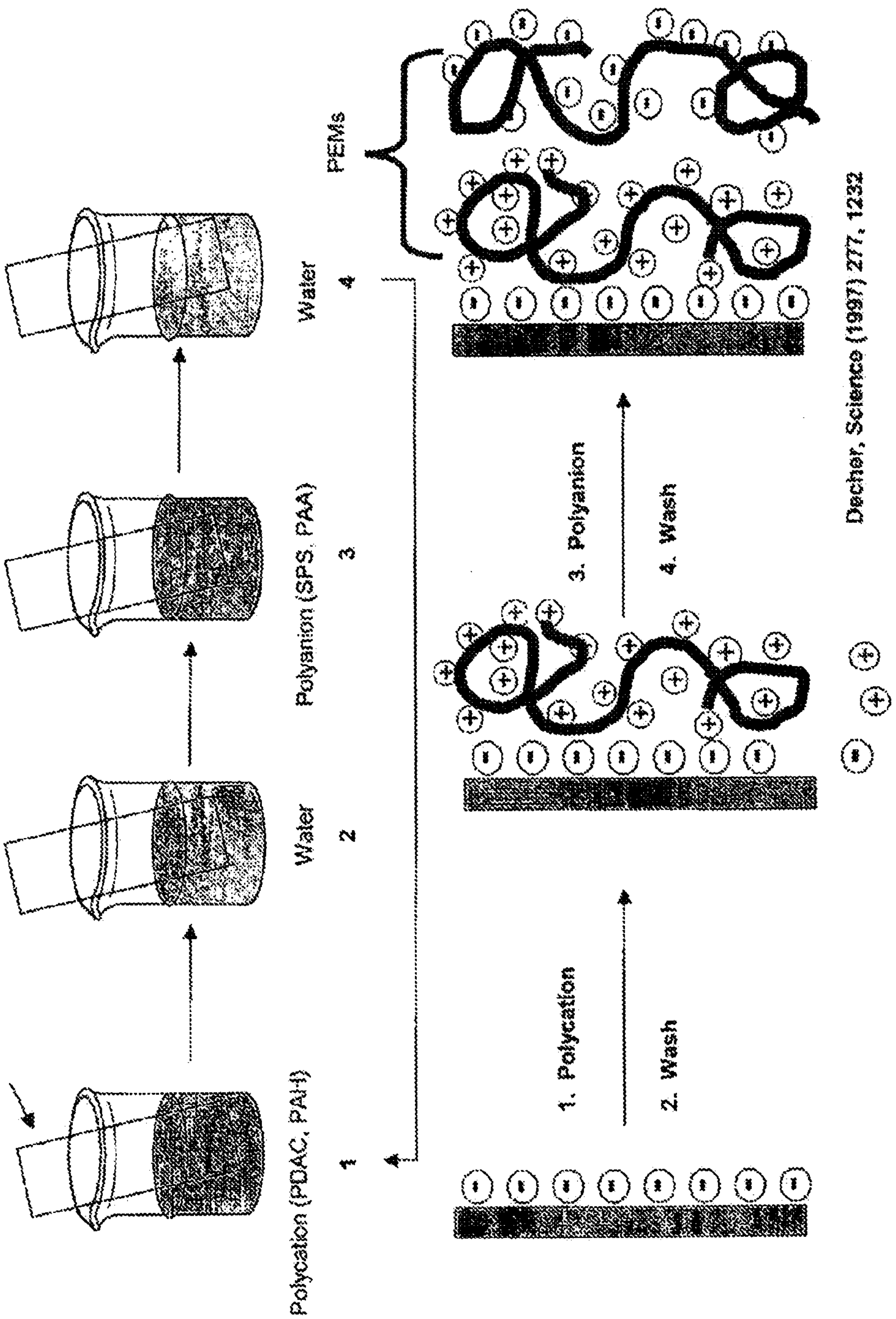

Phenol sensor

A
Thickness (nm)
Number of bilayers
B
Thickness (A°)
Number of Bilayers
C
-Z" (Ω)(Imaginary)
Z' (Ω)(Real)
(a)
(b)
(c)
(d)
(e)

Sensing technique: Step voltammetry

SEQ ID NO: 1
ctcaccaacccagccagcaacctggcaactgtggcaatcctgcctgtgtgtgctgaggtccccatggtggccttcacgctggag
ctgcagcacgccctgcaggccatcggtccgacgctactccttaacagtgacatcatccgggcacgcctgggggcctccgcact
ggatagcatccaagagttccggctgtcagggtggctggcccagcaggaggatgcacaccgtatcgtactctaccagacggac
gcctcgctgacgccctggaccgtgcgctgcctgcgacaggccgactgcatcctcattgtgggcctgggggaccaggagccta
ccctcggccagctggagcagatgctggagaacacggctgtgcgcgcccttaagcagctagtcctgctccaccgagaggaggg
tgcgggccccacgcgcaccgtggagtggctaaatatgcgcagctggtgctcggggcacctgcacctgcgctgtccgcgccgc
ctcttttcgcgccgcagccctgccaagctgcatgagctctacgagaaggttttctccaggcgcgcggaccggcacagcgacttc
tcccgcttggcgagggtgctcacggggaacaccattgcccttgtgctaggcgggggcggggccaggggctgctcgcacatcg
gagtactaaaggcattagaggaggcgggggtccccgtggacctggtgggcggcacgtccattggctctttcatcggagcgttgt
acgcggaggagcgcagcgccagccgcacgaagcagcgggcccgggagtgggccaagagcatgacttcggtgctggaacc
tgtgttggacctcacgtacccagtcacctccatgttcactgggtctgcctttaaccgcagcatccatcgggtcttccaggataagca
gattgaggacctgtggctgccttacttcaacgtgaccacagatatcaccgcctcagccatgcgagtccacaaagatggctccctg
tggcggtacgtgcgcgccagcatgacgctgtcgggctacctgcccccgctgtgcgaccccaaggacgggcacctactcatgg
atggcggctacatcaacaatctgccagcggacatcgcccgcagcatgggtgccaaaacggtcatcgccattgacgtggggag
ccaggatgagacggacctcagcacctacggggacagcctgtccggctggtggctgctgtggaagcggctgaatccctgggct
gacaaggtaaaggttccagacatggctgaaatccagtcccgcctggcctacgtgtcctgtgtgcggcagctagaggttgtcaag
tccagctcctactgcgagtacctgcgcccgcccatcgactgcttcaagaccatggactttgggaagttcgaccagatctatgatgt
gggctaccagtacgggaaggcggtgtttggaggctggagccgtggcaacgtcattgag

Figure 12A

SEQ ID NO:2
LTNPASNLATVAILPVCAEVPMVAFTLELQHALQAIGPTLLLNSDIIRARLGASAL
DSIQEFRLSGWLAQQEDAHRIVLYQTDASLTPWTVRCLRQADCILIVGLGDQEPT
LGQLEQMLENTAVRALKQLVLLHREEGAGPTRTVEWLNMRSWCSGHLHLRCPR
RLFSRRSPAKLHELYEKVFSRRADRHSDFSRLARVLTGNTIALVLGGGGARGCSH
IGVLKALEEAGVPVDLVGGTSIGSFIGALYAEERSASRTKQRAREWAKSMTSVLE
PVLDLTYPVTSMFTGSAFNRSIHRVFQDKQIEDLWLPYFNVTTDITASAMRVHKD
GSLWRYVRASMTLSGYLPPLCDPKDGHLLMDGGYINNLPADIARSMGAKTVIAI
DVGSQDETDLSTYGDSLSGWWLLWKRLNPWADKVKVPDMAEIQSRLAYVSCV
RQLEVVKSSSYCEYLRPPIDCFKTMDFGKFDQIYDVGYQYGKAVFGGWSRGNVI
E

Figure 12B

SEQ ID NO: 3 atggaggctccgctgcaaactggaatggtgcttggcgtgatgatcggggccggagtggcggtggtggtcacggccgtgctcat
cctcctggtggtgcggaggctgcgagtgccaaaaaccccagccccggatggcccccggtatcggttccggaagagggacaa
agtgctcttctatggccggaagattatgcggaaggtgtcacaatccacctcctccctcgtggatacctctgtctccgccacctccc
ggccacgcatgaggaagaaactgaagatgctcaacattgccaagaagatcctgcgcatccagaaagagacgcccacgctgca
gcggaaggagcccccgcccgcagtgctagaagctgacctgaccgagggcgacctggctaactcccatctgccctctgaagtg
ctttatatgctcaagaacgtccgggtgctgggccacttcgagaagccactcttcctggagctctgccgccacatggtcttccagcg
gctgggccagggtgactacgtcttccggccgggccagccagatgccagcatctacgtggtgcaggacgggctgctggagctc
tgtctgccagggcctgacgggaaggagtgtgtggtgaaggaagtggttcctggggacagcgtcaacagccttctcagcatcct
ggatgtcatcaccggtcaccagcatccccagcggaccgtgtctgcccgggcggcccgggactccacggtgctgcgcctgccg
gtggaagcattctccgcggtcttcaccaagtacccggagagcttggtgcgggtcgtgcagatcatcatggtgcggctgcagcga
gtcaccttcctggcactgcacaactacctgggtctgaccaatgagctcttcagccacgagatccagcccctgcgtctgttcccca
gccccggcctcccaactcgcaccagccctgtgcggggctccaagagaatggtcagcacctcagctacagacgagcccaggg
agaccccagggcggccacccgatcccaccggggccccgctgcctggacctacaggggaccctgtgaagcccacatccctgg
aaacccccctcggcccctctgctgagccgctgcgtctccatgccaggggacatctcaggcttgcagggtggcccccgctccgac
ttcgacatggcctatgagcgtggccggatctccgtgtccctgcaggaagaggcctccgggggtccctggcagcccccgctcg
gacccccactcaggagcctcgtgagcagccggcaggcgcctgtgaatacagctactgtgaggatgagtcggccactggtggc
tgccctttcgggccctaccagggccgccagaccagcagcatcttcgaggcagcaaagcaggagctggccaagctgatgcgg
attgaggacccctccctcctgaacagcagagtcttgctgcaccacgccaaagctggcaccatcattgcccgccagggagacca
ggacgtgagcctgcacttcgtgctctggggctgcctgcacgtgtaccagcgcatgatcgacaaggcggaggacgtgtgcctgtt
cgtagcgcagcccggggaactggtggggcagctggcggtgctcactggcgaacctctcatcttcacactgcgagcccaacgc
gactgcaccttcctgcggatctccaagtccgacttctatgagatcatgcgcgcacagcccagtgtggtgctgagtgcggcgcac
acggtggcagccaggatgtcgcccttcgtgcgccagatggacttcgccatcgactggactgcagtggaggcgggacgcgcgc
tgtacaggcagggcgaccgctccgactgcacttacatcgtgctcaatgggcggctgcgtagcgtgatccagcgaggcagtggc
aagaaggagctggtgggcgagtacggccgcggcgacctcatcggcgtggtggaggcactgacccggcagccgcgagcca
cgacggtgcacgcggtgcgcgacacggagctagccaagcttcccgagggcaccttgggtcacatcaaacgccggtacccgc
aggtcgtgacccgccttatccacctactgagccagaaaattctagggaatttgcagcagctgcaaggacccttcccagcaggct
ctgggttgggtgtgcccccacactcggaactcaccaacccagccagcaacctggcaactgtggcaatcctgcctgtgtgtgctg
aggtccccatggtggccttcacgctggagctgcagcacgccctgcaggccatcggtccgacgctactccttaacagtgacatca
tccgggcacgcctggggggcctccgcactggatagcatccaagagttccggctgtcagggtggctggcccagcaggaggatgc
acaccgtatcgtactctaccagacggacgcctcgctgacgccctggaccgtgcgctgcctgcgacaggccgactgcatcctcat
tgtgggcctgggggaccaggagcctaccctcggccagctggagcagatgctggagaacacggctgtgcgcgcccttaagca
gctagtcctgctccaccgagaggagggtgcgggccccacgcgcaccgtggagtggctaaatatgcgcagctggtgctcggg
gcacctgcacctgcgctgtccgcgccgcctcttttcgcgccgcagccctgccaagctgcatgagctctacgagaaggttttctcc
aggcgcgcggaccggcacagcgacttctcccgcttggcgagggtgctcacggggaacaccattgcccttgtgctaggcgggg
gcggggccaggggctgctcgcacatcggagtactaaaggcattagaggaggcgggggtccccgtggacctggtgggcggc
acgtccattggctctttcatcggagcgttgtacgcggaggagcgcagcgccagccgcacgaagcagcgggcccgggagtgg
gccaagagcatgacttcggtgctggaacctgtgttggacctcacgtacccagtcacctccatgttcactgggtctgcctttaaccg
cagcatccatcgggtcttccaggataagcagattgaggacctgtggctgccttacttcaacgtgaccacagatatcaccgcctca
gccatgcgagtccacaaagatggctccctgtggcggtacgtgcgcgccagcatgacgctgtcgggctacctgcccccgctgtg
cgaccccaaggacgggcacctactcatggatggcggctacatcaacaatctgccagcggacatcgcccgcagcatgggtgcc
aaaacggtcatcgccattgacgtggggagccaggatgagacggacctcagcacctacggggacagcctgtccggctggtgg
ctgctgtggaagcggctgaatccctgggctgacaaggtaaaggttccagacatggctgaaatccagtcccgcctggcctacgtg
tcctgtgtgcggcagctagaggttgtcaagtccagctcctactgcgagtacctgcgcccgcccatcgactgcttcaagaccatgg
actttgggaagttcgaccagatctatgatgtgggctaccagtacgggaaggcggtgtttggaggctggagccgtggcaacgtca
ttgagaaaatgctcacagaccggcggtctacagaccttaatgagagccgccgtgcagacgtgcttgccttcccaagctctggctt
cactgacttggcagagattgtgtcccggattgagcccccacgagctatgtctctgatggctgtgctgacggagaggagtcagat
tgtctgacagagtatgaggaggacgccggacccgactgctcgagggatgaagggggtcccccgagggcgcaagtcccag
cactgcctccgagatggaggaggagaagtcgattctccggcaacgacgctgtctgccccaggagccgcccggctcagccaca
gatgcc

Figure 12C

SEQ ID NO: 4
MEAPLQTGMVLGVMIGAGVAVVVTAVLILLVVRRLRVPKTPAPDGPRYRFRKR
DKVLFYGRKIMRKVSQSTSSLVDTSVSATSRPRMRKKLKMLNIAKKILRIQKETP
TLQRKEPPPAVLEADLTEGDLANSHLPSEVLYMLKNVRVLGHFEKPLFLELCRH
MVFQRLGQGDYVFRPGQPDASIYVVQDGLLELCLPGPDGKECVVKEVVPGDSV
NSLLSILDVITGHQHPQRTVSARAARDSTVLRLPVEAFSAVFTKYPESLVRVVQII
MVRLQRVTFLALHNYLGLTNELFSHEIQPLRLFPSPGLPTRTSPVRGSKRMVSTSA
TDEPRETPGRPPDPTGAPLPGPTGDPVKPTSLETPSAPLLSRCVSMPGDISGLQGG
PRSDFDMAYERGRISVSLQEEASGGSLAAPARTPTQEPREQPAGACEYSYCEDES
ATGGCPFGPYQGRQTSSIFEAAKQELAKLMRIEDPSLLNSRVLLHHAKAGTIIARQ
GDQDVSLHFVLWGCLHVYQRMIDKAEDVCLFVAQPGELVGQLAVLTGEPLIFTL
RAQRDCTFLRISKSDFYEIMRAQPSVVLSAAHTVAARMSPFVRQMDFAIDWTAV
EAGRALYRQGDRSDCTYIVLNGRLRSVIQRGSGKKELVGEYGRGDLIGVVEALT
RQPRATTVHAVRDTELAKLPEGTLGHIKRRYPQVVTRLIHLLSQKILGNLQQLQG
PFPAGSGLGVPPHSELTNPASNLATVAILPVCAEVPMVAFTLELQHALQAIGPTLL
LNSDIIRARLGASALDSIQEFRLSGWLAQQEDAHRIVLYQTDASLTPWTVRCLRQ
ADCILIVGLGDQEPTLGQLEQMLENTAVRALKQLVLLHREEGAGPTRTVEWLNM
RSWCSGHLHLRCPRRLFSRRSPAKLHELYEKVFSRRADRHSDFSRLARVLTGNTI
ALVLGGGGARGCSHIGVLKALEEAGVPVDLVGGTSIGSFIGALYAEERSASRTKQ
RAREWAKSMTSVLEPVLDLTYPVTSMFTGSAFNRSIHRVFQDKQIEDLWLPYFN
VTTDITASAMRVHKDGSLWRYVRASMTLSGYLPPLCDPKDGHLLMDGGYINNL
PADIARSMGAKTVIAIDVGSQDETDLSTYGDSLSGWWLLWKRLNPWADKVKVP
DMAEIQSRLAYVSCVRQLEVVKSSSYCEYLRPPIDCFKTMDFGKFDQIYDVGYQ
YGKAVFGGWSRGNVIEKMLTDRRSTDLNESRRADVLAFPSSGFTDLAEIVSRIEP
PTSYVSDGCADGEESDCLTEYEEDAGPDCSRDEGGSPEGASPSTASEMEEEKSIL
RQRRCLPQEPPGSATDA

Figure 12D

SEQ ID NO: 5 ccccacgccaccccaagcatcccaggactcttctgaaacagggcagtgacccgggaggaagtcaccaggtgcagaggaccg
tgccctgtggggacctgcctgcaggctgctgacagactccgggctaccagatcggccgtccagctggaatcaaccgatggag
gctccgctgcaaactggaatggtgcttggcgtgatgatcggggccggagtggcggtggtggtcacggccgtgctcatcctcctg
gtggtgcggaggctgcgagtgccaaaaaccccagccccggatggcccccggtatcggttccggaagagggacaaagtgctc
ttctatggccggaagattatgcggaaggtgtcacaatccacctcctccctcgtggatacctctgtctccgccacctcccggccacg
catgaggaagaaactgaagatgctcaacattgccaagaagatcctgcgcatccagaaagagacgccccacgctgcagcggaag
gagcccccgcccgcagtgctagaagctgacctgaccgagggcgacctggctaactcccatctgccctctgaagtgctttatatg
ctcaagaacgtccgggtgctgggccacttcgagaagccactcttcctggagctctgccgccacatggtcttccagcggctgggc
cagggtgactacgtcttccggccgggccagccagatgccagcatctacgtggtgcaggacgggctgctggagctctgtctgcc
agggcctgacgggaaggagtgtgtggtgaaggaagtggttcctggggacagcgtcaacagccttctcagcatcctggatgtca
tcaccggtcaccagcatccccagcggaccgtgtctgcccggcggcggcccgggactccacggtgctgcgcctgccggtggaag
cattctccgcggtcttcaccaagtacccggagagcttggtgcgggtcgtgcagatcatcatggtgcggctgcagcgagtcacctt
cctggcactgcacaactacctgggtctgaccaatgagctcttcagccacgagatccagcccctgcgtctgttccccagccccgg
cctcccaactcgcaccagccctgtgcggggctccaagagaatggtcagcacctcagctacagacgagcccagggagaccccc
agggcggccacccgatcccaccggggccccgctgcctggacctacaggggaccctgtgaagcccacatccctggaaacccc
ctcggcccctctgctgagccgctgcgtctccatgccaggggacatctcaggcttgcagggtggcccccgctccgacttcgacat
ggcctatgagcgtggccggatctccgtgtccctgcaggaagaggcctccggggggtccctggcagcccccgctcggacccc
cactcaggagcctcgtgagcagccggcaggcgcctgtgaatacagctactgtgaggatgagtcggccactggtggctgccctt
tcgggccctaccagggccgccagaccagcagcatcttcgaggcagcaaagcaggagctggccaagctgatgcggattgagg
acccctccctcctgaacagcagagtcttgctgcaccacgccaaagctggcaccatcattgcccgccagggagaccaggacgtg
agcctgcacttcgtgctctggggctgcctgcacgtgtaccagcgcatgatcgacaaggcggaggacgtgtgcctgttcgtagcg
cagcccggggaactggtggggcagctggcggtgctcactggcgaacctctcatcttcacactgcgagcccaacgcgactgca
ccttcctgcggatctccaagtccgacttctatgagatcatgcgcgcacagcccagtgtggtgctgagtgcggcgcacacggtgg
cagccaggatgtcgcccttcgtgcgccagatggacttcgccatcgactggactgcagtggaggcgggacgcgcgctgtacag
gcagggcgaccgctccgactgcacttacatcgtgctcaatgggcggctgcgtagcgtgatccagcgaggcagtggcaagaag
gagctggtgggcgagtacggccgcggcgacctcatcggcgtggtggaggcactgacccggcagccgcgagccacgacggt
gcacgcggtgcgcgacacggagctagccaagcttcccgagggcaccttgggtcacatcaaacgccggtacccgcaggtcgt
gacccgccttatccacctactgagccagaaaattctagggaatttgcagcagctgcaaggacccttcccagcaggctctgggttg
ggtgtgcccccacactcggaactcaccaacccagccagcaacctggcaactgtggcaatcctgcctgtgtgtgctgaggtcccc
atggtggccttcacgctggagctgcagcacgccctgcaggccatcggtccgacgctactccttaacagtgacatcatccgggca
cgcctggggggcctccgcactggatagcatccaagagttccggctgtcagggtggctggcccagcaggaggatgcacaccgta
tcgtactctaccagacggacgcctcgctgacgccctggaccgtgcgctgcctgcgacaggccgactgcatcctcattgtgggcc
tgggggaccaggagcctaccctcggccagctggagcagatgctggagaacacggctgtgcgcgcccttaagcagctagtcct
gctccaccgagaggagggtgcgggccccacgcgcaccgtggagtggctaaatatgcgcagctggtgctcggggcacctgca
cctgcgctgtccgcgccgcctcttttcgcgccgcagccctgccaagctgcatgagctctacgagaaggttttctccaggcgcgc
ggaccggcacagcgacttctcccgcttggcgagggtgctcacggggaacaccattgcccttgtgctaggcgggggcggggc
caggggctgctcgcacatcggagtactaaaggcattagaggaggcgggggtccccgtggacctggtgggcggcacgtccatt
ggctctttcatcggagcgttgtacgcggaggagcgcagcgccagccgcacgaagcagcgggcccgggagtgggccaagag
catgacttcggtgctggaacctgtgttggacctcacgtacccagtcacctccatgttcactgggtctgcctttaaccgcagcatcca
tcgggtcttccaggataagcagattgaggacctgtggctgccttacttcaacgtgaccacagatatcaccgcctcagccatgcga
gtccacaaagatggctccctgtggcggtacgtgcgcgccagcatgacgctgtcgggctacctgcccccgctgtgcgaccccaa
ggacgggcacctactcatggatggcggctacatcaacaatctgccagcggacatcgcccgcagcatgggtgccaaaacggtc
atcgccattgacgtggggagccaggatgagacggacctcagcacctacggggacagcctgtccggctggtggctgctgtgga
agcggctgaatccctgggctgacaaggtaaaggttccagacatggctgaaatccagtcccgcctggcctacgtgtcctgtgtgc
ggcagctagaggttgtcaagtccagctcctactgcgagtacctgcgcccgcccatcgactgcttcaagaccatggactttggga
agttcgaccagatctatgatgtgggctaccagtacgggaaggcggtgtttggaggctggagccgtggcaacgtcattgagaaaa
tgctcacagaccggcggtctacagaccttaatgagagccgccgtgcagacgtgcttgccttcccaagctctggcttcactgactt
ggcagagattgtgtcccggattgagcccccacgagctatgtctctgatggctgtgctgacggagaggagtcagattgtctgaca
gagtatgaggaggacgccggacccgactgctcgagggatgaagggggtcccccgagggcgcaagtcccagcactgcctc
cgagatggaggaggagaagtcgattctccggcaacgacgctgtctgccccaggagccgcccggctcagccacagatgcctg
aggacctcgacaggggtcacccccctccctcccacccctggactgggctgggggtggccccgtgggggtagctcactcccccct
cctgctgctatgcctgtgacccccgcggcccacacactggactgacctgccctgagcggggatgcagtgttgcactgatgactt
gaccagcccctcccccaataaactcgcctcttggaaaaaaaaaaaaaaaaaaaaaaaaaaaaaaaaaaaaaaaaaaaaa
aaa

Differential equations:

$$\frac{\partial^2 S_1}{\partial x^2} - \frac{S_1}{\lambda_1^2} = 0 \qquad \frac{\partial^2 S_2}{\partial x^2} - \frac{S_2}{\lambda_2^2} + \frac{S_1}{\lambda_1^2} = 0$$

$$\frac{\partial^2 S_3}{\partial x^2} - \frac{S_3}{\lambda_3^2} = 0 \qquad \frac{\partial^2 Q_4}{\partial x^2} + \frac{S_2}{\lambda_3^2} + \frac{S_3}{\lambda_3^2} = 0$$

Where:

$$\lambda_1 = \left(\frac{D_f K_1}{k_1 E_1}\right)^{\frac{1}{2}} \qquad \lambda_2 = \left(\frac{D_f K_2}{k_2 E_2}\right)^{\frac{1}{2}} \qquad \lambda_3 = \left(\frac{D_f K_3}{k_3 E_3}\right)^{\frac{1}{2}}$$

Figure 14

<u>Boundary conditions</u>:

1) Applied potential is sufficiently negative that:

$$[Q_4]_{x=0} = 0$$

2) Since phenyl valerate and phenol are electro-inactive:

$$[\frac{\partial S_1}{\partial x}]_{x=0} = 0, [\frac{\partial S_2}{\partial x}]_{x=0} = 0$$

3) Phenyl valerate is present in the bulk:

$$[S_1]_{x=\infty} = S_1(\infty), [S_2]_{x=\infty} = 0, [S_3]_{x=\infty} = 0, [Q_4]_{x=\infty} = 0$$

4) Assuming that at steady state, flux of phenyl valerate, catechol, phenol and quinone is same across the boundary between the enzyme layer and phosphate buffer.

$$D_f\left[\frac{\partial S_1}{\partial x}\right]_{x=L} = \frac{D_e}{k_p\delta}\left[k_p S_1(\infty) - [S_1]_{x=L}\right]$$

$$D_f\left[\frac{\partial S_2}{\partial x}\right]_{x=L} = -\frac{D_e}{k_p\delta}[S_2]_{x=L}$$

$$D_f\left[\frac{\partial S_3}{\partial x}\right]_{x=L} = -\frac{D_e}{k_p\delta}[S_3]_{x=L}$$

$$D_f\left[\frac{\partial Q_4}{\partial x}\right]_{x=L} = -\frac{D_e}{k_p\delta}[Q_4]_{x=L}$$

5) From law of conservation of mass, for any x inside the enzyme layer:

$$[Q_4] + [S_1] + [S_2] + [S_3] = S_1(\infty)$$

6) $$\frac{J}{nFD_f A} = [\frac{\partial S_3}{\partial x}]_{x=0} = -[\frac{\partial Q_4}{\partial x}]_{x=0}$$

Where $\frac{J}{A}$ denotes current density.

Figure 15

Solutions:

Phenyl valerate concentration:

$$S_1 = \frac{k_p S_1(\infty)}{\frac{P_m \theta_1}{m_e}\sinh\theta_1 + \cosh\theta_1}\cosh\left(\frac{x}{\lambda_1}\right)$$

Phenol concentration:

$$S_2 = \frac{k_p S_1(\infty)}{\frac{P_m \theta_1}{m_e}\sinh\theta_1 + \cosh\theta_1}\left(\frac{\theta_1^2}{\theta_2^2 - \theta_1^2}\right)\left[\cosh\left(\frac{x}{\lambda_1}\right) - \left(\frac{\frac{P_m \theta_1}{m_e}\sinh\theta_1 + \cosh\theta_1}{\frac{P_m \theta_2}{m_e}\sinh\theta_2 + \cosh\theta_2}\right)\cosh\frac{x}{\lambda_2}\right]$$

Catechol concentration:

$$S_3 = k_p S_1(\infty)\left[\frac{1}{\frac{P_m\theta_1}{m_e}\sinh\theta_1 + \cosh\theta_1} - \frac{1}{\frac{P_m\theta_2}{m_e}\sinh\theta_2 + \cosh\theta_2}\left(\frac{\theta_1^2}{\theta_2^2 - \theta_1^2}\right)\left(1 - \frac{\frac{P_m\theta_1}{m_e}\sinh\theta_1 + \cosh\theta_1}{\frac{P_m\theta_2}{m_e}\sinh\theta_2 + \cosh\theta_2}\right)\right]\left[\cosh\frac{x}{\lambda_3} - \frac{\frac{P_m\theta_3}{m_e}\sinh\theta_3 + \cosh\theta_3}{\frac{P_m\theta_3}{m_e}\cosh\theta_3 + \sinh\theta_3}\sinh\frac{x}{\lambda_3}\right]$$

Quinone concentration:

$$Q_4 = S_1(\infty) - S_1 - S_2 - S_3$$

$S_1(\infty)$: Concentration of phenyl valerate in bulk.

Current:

$$\frac{I}{A} = 2FP_m\theta_3 S_1(\infty)\left[\frac{1}{\frac{P_m\theta_1}{m_e}\sinh\theta_1 + \cosh\theta_1} - \frac{1}{\frac{P_m\theta_2}{m_e}\sinh\theta_2 + \cosh\theta_2}\left(\frac{\theta_1^2}{\theta_2^2 - \theta_1^2}\right)\left(1 - \frac{\frac{P_m\theta_1}{m_e}\sinh\theta_1 + \cosh\theta_1}{\frac{P_m\theta_2}{m_e}\sinh\theta_2 + \cosh\theta_2}\right)\right]\left[\frac{\frac{P_m\theta_3}{m_e}\sinh\theta_3 + \cosh\theta_3}{\frac{P_m\theta_3}{m_e}\cosh\theta_3 + \sinh\theta_3}\right]$$

Where:

$$m_e = \frac{D_e}{\ldots} \qquad \lambda_1 = \left(\frac{D_f K_1 S}{k_1 E_1}\right)^{\frac{1}{2}}$$

$$P_m = \frac{k_e D_f}{\lambda_2} \qquad \lambda_2 = \left(\frac{D_f K_2}{k_2 E_2}\right)^{\frac{1}{2}}$$

$$\theta_1 = \frac{L}{\lambda_1}, \theta_2 = \frac{L}{\lambda_2}, \theta_3 = \frac{L}{\lambda_3} \qquad \lambda_3 = \left(\frac{D_f K_3}{k_3 E_3}\right)^{\frac{1}{2}}$$

$S_1(\infty)$: Concentration of phenyl valerate in bulk.

NANOSTRUCTURED BIOSENSOR CONTAINING NEUROPATHY TARGET ESTERASE ACTIVITY

CROSS-REFERENCE TO RELATED PATENT DOCUMENTS

This application claims the benefit of priority to U.S. Provisional Patent Application Ser. No. 60/930,465, filed on May 16, 2007, which is herein incorporated by reference in its entirety.

This invention was made with government support from the United States National Science Foundation grant number CTS-0609164 and the United States Army (DAAD19-02-1-0388). The United States Government has certain rights in the invention.

FIELD OF THE INVENTION

The present invention provides compositions, devices and methods for detecting esterase activity. The present invention also provides devices and methods of detecting esterase inhibitors, for example, organophosphates. In particular, the present invention provides a biosensor comprising Neuropathy Target Esterase (NTE) polypeptides. Further, the present invention relates to medicine, industrial chemistry, agriculture, and homeland security.

BACKGROUND OF THE INVENTION

Widespread and long-term use of organophosphate (OP) compounds in industry and agriculture has made these hazardous compounds a part of environment, placing the health of human population at risk. This risk is the result of the capability of certain OP compounds to bind to and alter activity of Neuropathy Target Esterase (NTE), a membrane-bound esterase enzyme. Irreversible binding of OP compounds to NTE results in a debilitating neural disease known as (OP)-induced delayed neuropathy (OPIDN). Therefore, in addition to environmental exposure, compounds that inhibit esterase activity, and in particular NTE activity may be exploited in wars and by terrorists who might use compounds that cause OPIDN as chemical weapons against humans and animals.

Further, NTE has recently been implicated in well-known neurological diseases. Such diseases include motor-neuron diseases that occur spontaneously, without exposure to OP compounds, for example, amyotrophic lateral sclerosis (ALS), also known as Lou Gehrig's disease.

Because NTE plays a central role in both chemically induced and spontaneously occurring neurological diseases, there is a critical need for sensors with which to measure its esterase activity.

SUMMARY OF THE INVENTION

The present invention provides compositions, devices and methods for detecting esterase activity. The present invention also provides devices and methods of detecting esterase inhibitors, for example, organophosphates. In particular, the present invention provides a biosensor comprising Neuropathy Target Esterase (NTE) polypeptides. Further, the present invention relates to medicine, industrial chemistry, agriculture, and homeland security.

Advantages of using the biosensor of the present inventions include economical production in combination with real-time measurements (within several seconds), a continuous measurement of the proteins' activity combined with high sensitivity, in particular for detecting the presence of Neuropathy Target Esterase (NTE) inhibitors, such as organophosphates in a sample.

The present invention relates in general to measuring esterase activity, including esterase proteins and nucleic acids encoding these proteins and active fragments thereof. In a preferred embodiment, the present inventions relate to NTE proteins and nucleic acids encoding NTE proteins and enzymatically active fragments thereof. The present invention further provides assays for the detection of NTE polymorphisms and mutations associated with disease states, as well as methods of screening for therapeutic agents, ligands, and modulators of NTE proteins.

Thus, in some embodiments, the inventions provide a device, comprising: a linker attached to an electrode, said linker positioned between said electrode and an enzyme immobilizing layer, said layer interacting with an oxidase and an esterase. In some embodiments, the enzyme immobilizing layer comprises a plurality of ammonium ions. In some embodiments, the enzyme immobilizing layer comprises poly-L-lysine. In some embodiments, the linker comprises thioctic acid. In some embodiments, the esterase is a neuropathy target esterase. In some embodiments, the oxidase is a tyrosinase. In some embodiments, the electrode is an amperometric electrode.

The inventions further provide, a device, comprising: a linker attached to an electrode, said linker positioned between said electrode and a first enzyme immobilizing layer, said first layer interacting with an oxidase, said oxidase positioned between said first enzyme immobilizing layer and a second enzyme immobilizing layer, said second layer interacting with an esterase. In some embodiments, the first and second enzyme immobilizing layers comprises a plurality of ammonium ions. In some embodiments, the first and second layers comprises poly-L-lysine. In some embodiments, the linker comprises thioctic acid. In some embodiments, the oxidase is a tyrosinase. In some embodiments, the esterase is a neuropathy target esterase. In some embodiments, the electrode is an amperometric electrode.

In some embodiments, the inventions provide a method, comprising, a) providing, i) a device, comprising: a linker attached to an electrode, said linker positioned between said electrode and an enzyme immobilizing layer, said layer interacting with an oxidase and an esterase; ii) a substrate, and b) contacting said device with said substrate; and c) measuring enzyme activity. In some embodiments, the substrate is an esterase substrate. In some embodiments, the substrate is in solution. In some embodiments, the enzyme activity measured in step c) is esterase activity. In some embodiments, the substrate is phenyl valerate. In some embodiments, the enzyme activity measured in step c) is measured in real-time.

In some embodiments, the invention provides a device comprising a purified oxidase polypeptide, a purified esterase polypeptide, and an electrode, wherein said oxidase polypeptide is attached to the electrode. In preferred embodiments, the esterase polypeptide is attached to the electrode. It is not intended that the present invention be limited by the type of attachment. In general, the type of attachment allows for catalytic activity of the oxidase and catalytic activity of the esterase polypeptides. Preferred embodiments of the present invention comprise biological molecules such as proteins, enzymes, amino acids, synthetic polymers, etc. attached to or associated with the electrode. A biological material is "attached" to an electrode when it is associated with the electrode through a chemical or physical interaction or charge interaction. In some preferred embodiments, the attachment is through a covalent bond. However, attachments need not be covalent or direct. In some embodiments, biological molecules are attached to an electrode through a spacer molecule, linker group, an enzyme immobilizing compound or enzyme immobilizing molecule, cross-linking compound, and the like for providing a linker layer. Such “sensor-coupling” or “spacer” or “linker” or “bridge” molecules are molecules that have a first portion that attaches to the biological material and a second portion that attaches to the solid support of the electrode. Thus, when attached to the electrode, the spacer molecule separates the electrode and the biological materials, but is attached to both. In some embodiments, biological molecules are attached to an electrode through layers of spacer molecules, linker groups, enzyme immobilizing compounds, cross-linking compounds, and the like for providing an enzyme immobilizing layer. Preferable attachment chemistries, such as those provided for linker and enzyme attachments of the present inventions, preserve the activity of the biological molecule and do not produce background activity. Suitable chemistries include, but are not limited to, amide, urethane, carbonyl, thioester, disulfide, organosilicon, and the like. It is not intended that the present invention be limited by the type of electrode. In general, the type of electrode of use in the present inventions is capable of participating in redox reactions resulting from the catalytic activity of the attached enzymes. In a preferred embodiment, an electrode is capable of accepting electrons produced by the catalytic activity of the attached enzymes. It is not intended that the present invention be limited by the oxidase polypeptide. Oxidase polypeptides include but are not limited to a catechol oxidase (E.C. 1.10.3.1), a tryosinase (E.C. 1.10.3.1), a phenol oxidase (E.C. 1.10.3.1), a polyphenol oxidase (E.C. 1.10.3.1), a tryosinase (E.C. 1.10.3.1), a laccase (E. C. 1.10.3.2), a peroxidase (EC 1.11.1.7), and a horseradish peroxidase (HRP). It is not intended that the present invention be limited by the esterase polypeptide. Esterase polypeptides include but are not limited to a recombinant human neuropathy target esterase, acetylcholinesterase, and butyrylcholine esterase. In some embodiments, the neuropathy target esterase includes but is not limited to a SEQ ID NO:02, a SEQ ID NO:04, and an amino acid sequence comprising residues 727-1216 of a full-length neuropathy target esterase. In preferred embodiments, said neuropathy target esterase enzyme comprises a neuropathy target esterase activity domain. In some embodiments, electrodes include, but are not limited to, amperometric electrodes, tyrosinase electrodes, electrodes comprising electron conducting material, electrodes comprising electron conducting material wherein the electron conducting material is located on the surface of the electrode, and the like. In preferred embodiments, the electrode is an amperometric electrode. It is not intended that the present invention be limited by the amperometric electrode. Amperometric electrodes include but are not limited to a stationary electrode and a rotating disk electrode. In some embodiments, the amperometric electrode further comprises, a layer of a sensor-coupling molecule, wherein said molecule bridges an inorganic surface of the amperometric electrode to an enzyme immobilizing compound, a bilayer of an enzyme immobilizing compound and the oxidase polypeptide, a layer of an enzyme immobilizing compound for attaching an esterase enzyme, and a layer of the esterase polypeptide. It is not intended that the present invention be limited by the sensor-coupling molecule. In preferred embodiments, said sensor-coupling molecule is thioctic acid. It is not intended that the present invention be limited by the enzyme immobilizing compound. The enzyme immobilizing compound includes but is not limited to a covalent bond forming compound, a cross-linking compound, and an entrapment compound. In preferred embodiments, the enzyme immobilizing compound comprising the enzyme immobilizing layer, includes but is not limited to a poly-L-lysine, polyacrylic acid, glutaraldehyde, and polyacrylamide. In preferred embodiments, the enzyme immobilizing compound is a poly-L-lysine. It is not intended that the present invention be limited by the inorganic surface. The inorganic surface includes but is not limited to a layer of an electron conducting material. It is not intended that the present invention be limited by the electron conducting material. The electron conducting material includes but is not limited to a layer of gold, carbon, and indium tin oxide, et cetera. In preferred embodiments, the electron conducting material is gold. In some embodiments, the electron conducting molecule is located on the surface of the amperometric electrode.

In some embodiments, the invention provides an expression vector comprising a human neuropathy target esterase nucleic acid sequence encoding a full-length human neuropathy target esterase polypeptide operably linked to a prokaryotic regulatory element. It is not intended that the present invention be limited by the expression vector. Expression vectors include, but are not limited to, prokaryote and eukaryote expression vectors. In preferred embodiments, said expression vector is a prokaryote expression vector. In some embodiments, said expression vector is an *Escherichia coli* expression vector. It is not intended that the present invention be limited by the length of the nucleic acid sequence encoding a human neuropathy target esterase polypeptide. Human neuropathy target esterase nucleic acids include, but are not limited to, a full-length human neuropathy target esterase coding sequence and a fragment of human neuropathy target esterase coding sequence. In some embodiments, said nucleic acid sequence comprises SEQ ID NO:01. In some embodiments, said nucleic acid sequence comprises SEQ ID NO:03. In some embodiments, said nucleic acid sequence comprises SEQ ID NO:05. In some embodiments, said nucleic acid sequence is greater than 1470 nucleic acid sequences. In some embodiments, said nucleic acid sequence ranges from 1470-3981 nucleic acid sequences. It is not intended that the present invention be limited by the length of the human neuropathy target esterase polypeptide sequence. Human neuropathy target esterase polypeptides include, but are not limited to, a full-length human neuropathy target esterase polypeptide sequence and a fragment of human neuropathy target esterase polypeptide. In some embodiments, said polypeptide comprises SEQ ID NO:04. In some embodiments, said polypeptide comprises SEQ ID NO:02. In some embodiments, said neuropathy target esterase polypeptide is greater than 489 amino acids in length. In some embodiments, said neuropathy target esterase polypeptide ranges from 490-1327 amino acids in length. In some embodiments, said polypeptide comprises a neuropathy target esterase domain. In some embodiments, said neuropathy target esterase polypeptide has esterase activity. It is not intended that the present invention be limited by the type of neuropathy target esterase activity Esterase activity includes, but is not limited to, hydrolysis of an ester bond, serine esterase activity, phenyl valerate hydrolase activity, and the like. In some embodiments, said prokaryotic regulatory elements are expression elements. It is not intended that the present invention be limited by the prokaryotic regulatory elements. Prokaryotic regulatory elements include, but are not limited to, promoters, operators, ribosome binding sites, termination sites, et cetera. In a preferred embodiment, said expression vector further comprises a host cell. It is not intended that the present invention be limited by the type of host cell. Host cells include, but are not limited to, prokaryote and eukaryote host cells. In a preferred embodiment, said host cell is an *Escherichia coli*.

In some embodiments, the invention relates to a device for measuring neuropathy target esterase activity comprising a tyrosinase electrode displaying active recombinant purified neuropathy target esterase enzyme. In one embodiment, said active recombinant purified neuropathy target esterase enzyme is capable of hydrolyzing an esterase bond. In some embodiments, said active recombinant purified neuropathy target esterase enzyme is capable of hydrolyzing phenyl valerate. In one embodiment, said active recombinant purified neuropathy target esterase enzyme is a full-length esterase enzyme. In other embodiments, said active recombinant purified neuropathy target esterase enzyme is a fragment of esterase enzyme.

In some embodiments, the invention relates to a device for measuring esterase activity, comprising, an amperometric electrode, wherein said amperometric electrode further comprises an esterase biosensor interface. In a preferred embodiment, an esterase biosensor interface comprises attached layers of organic molecules.

In some embodiments, the invention relates to a device for measuring esterase activity, comprising, an amperometric electrode, wherein said amperometric electrode further comprises layers of organic molecules. In a preferred embodiment, said layers of organic molecules are attached layers. In a preferred embodiment, said layers of organic molecules comprise at least one layer of a sensor-coupling molecule, at least two layers of an enzyme immobilizing compound, at least one layer of a tyrosinase enzyme, and at least one layer of an esterase enzyme. In one embodiment, said amperometric electrode further comprises an inorganic molecular surface. In a preferred embodiment, said layers of organic molecules are attached to each other and to the inorganic molecular surface. In preferred embodiments, said inorganic surface molecules comprise an electron conducting material. It is not intended that the present invention be limited by the type of electron conducting material. Indeed, the electron conducting material includes but is not limited to gold, carbon, indium tin oxide, et cetera. It is not intended that the present invention be limited by the type of sensor-coupling molecule. In general, the sensor-coupling molecule is capable of attaching an inorganic surface to an organic molecule. Indeed, sensor-coupling or linker molecules include but are not limited to thioctic acid, thioctic acid derivatives, organosilicon compounds, silanes, and the like. In one embodiment, said electrode comprises at least five organic layers. In one embodiment, said organic layer is at least 0.0001 nanometer in thickness. In one embodiment, said layer is at least 0.001 nanometer in thickness. In one embodiment, said layer is at least 0.01 nanometer in thickness. In one embodiment, said layer is at least 0.1 nanometer in thickness. In one embodiment, said layer ranges from 0.0001 nanometer to 1,000 nanometers in thickness. Accordingly in some embodiments, said layer is 0.0001 nanometer, 0.001 nanometer, 0.01 nanometer, 0.1 nanometer (or any amount between 0.0001 nanometer and 1,000 nanometers) in thickness. In some embodiments, said layer comprises a bilayer. In one embodiment, said bilayer is at least 0.001 nanometer in thickness. In one embodiment, said bilayer is at least 0.01 nanometer in thickness. In one embodiment, said bilayer is at least 0.1 nanometer in thickness. In one embodiment, said bilayer ranges from 0.001 nanometer to 2,000 nanometers in thickness. Accordingly in some embodiments, said layer is 0.001 nanometer, 0.01 nanometer, 0.1 nanometer (or any amount between 0.001 nanometer and 2,000 nanometers) in thickness. In one embodiment, said bilayer consists of a layer of an enzyme immobilizing compound and a layer of enzyme. In one embodiment, said enzyme is a tyrosinase enzyme. In one embodiment, said enzyme is an esterase enzyme. In a further embodiment, said electrode comprises at least one bilayer, wherein said bilayer consists of a layer of an enzyme immobilizing compound and a layer of tyrosinase enzyme. In a further embodiment, said electrode comprises at least two bilayers, wherein said bilayer consists of a layer of an enzyme immobilizing compound and a layer of tyrosinase enzyme. In a further embodiment, said electrode comprises at least three bilayers, wherein said bilayer consists of a layer of an enzyme immobilizing compound and a layer of tyrosinase enzyme and at least one additional layer of an enzyme immobilizing compound. In a preferred embodiment, said electrode comprises at least three bilayers, wherein said bilayer consists of a layer of an enzyme immobilizing compound and a layer of tyrosinase enzyme, at least one additional layer of an enzyme immobilizing compound, and at least one layer of esterase enzyme. It is not intended that the present invention be limited by the type of enzyme immobilizing compound. In general, an enzyme immobilizing compound indirectly attaches an enzyme to the electrode. Indeed, enzyme immobilizing compounds include but are not limited to covalent bond forming compounds, cross-linking compounds, entrapment compounds, and the like. In one embodiment, said enzyme immobilizing compound is a poly-L-lysine. In one embodiment, said enzyme immobilizing compound is a polyacrylic acid. In one embodiment, said enzyme immobilizing compound is a glutaraldehyde. In one embodiment, said enzyme immobilizing compound is a polyacrylamide. In one embodiment, the esterase enzyme is a full-length polypeptide. In one embodiment, the esterase enzyme is fragment of the full-length polypeptide. It is not intended that the present invention be limited by the type of esterase enzyme. Indeed, the esterase enzyme includes but is not limited to a neuropathy target esterase, a acetylcholinesterase, a butyrylcholine esterase, and the like.

In preferred embodiments, said esterase is a neuropathy target esterase enzyme. In some embodiments, said neuropathy target esterase enzyme comprises a neuropathy target esterase domain. In some embodiments, said neuropathy target esterase domain comprises amino acids 727-1216 or 733-1216. In some embodiments, said neuropathy target esterase domain is capable of esterase activity.

In some embodiments, the invention relates to a method of providing an esterase biosensor, comprising, a) providing, i) an amperometric electrode, wherein said electrode comprises an inorganic surface, ii) a solution of a sensor-coupling molecule, wherein said molecule is capable of attaching an inorganic surface to an organic molecule, iii) a solution of an enzyme immobilizing compound, iv) a solution of a tyrosinase enzyme polypeptide, and v) a solution of an esterase enzyme polypeptide; and b) incubating the electrode in a solution of a sensor-coupling molecule, c) incubating the electrode in a solution of an enzyme immobilizing compound, d) incubating the electrode in a solution of a tyrosinase enzyme, e) incubating the electrode in a solution of an enzyme immobilizing compound, and f) incubating the electrode in a solution of an esterase enzyme. In one embodiment, steps c) and d) are repeated at least one time. In one embodiment, steps c) and d) are repeated at least three times. In one embodiment, the sensor-coupling molecule is thioctic acid. In one embodiment, the enzyme immobilizing compound is poly-L-lysine (PLL). In one embodiment, the esterase enzyme polypeptide is a neuropathy esterase enzyme polypeptide. In one embodiment, the esterase enzyme polypeptide is an acetylcholinesterase enzyme polypeptide.

In one embodiment, the esterase enzyme polypeptide is a butyrylcholinesterase enzyme polypeptide. It is not intended that the present invention be limited by the type of incubating. In general, the type of incubating is intended to allow a layer of a molecule, a compound, or a polypeptide to attach to the surface of the electrode. Indeed, the incubating includes but is not limited to dipping, immersing, plunging, and the like, of the electrode into a solution for a specified amount of time.

In some embodiments, the invention relates to a method of providing an esterase biosensor, comprising, a) providing, i) an amperometric electrode, wherein said electrode comprises an inorganic surface, ii) a sensor-coupling molecule, wherein said molecule is capable of attaching an inorganic surface to an organic molecule, iii) an enzyme immobilizing compound, iv) a tyrosinase enzyme polypeptide, and v) an esterase enzyme polypeptide; and b) coating the electrode surface with a sensor-coupling molecule, c) layering the enzyme immobilizing compound on top of the sensor-coupling molecule, d) layering the tyrosinase enzyme on top of the enzyme immobilizing compound, e) layering the enzyme immobilizing compound on top of tyrosinase enzyme, f) layering the esterase enzyme on top of the enzyme immobilizing compound. It is not intended that the present invention be limited by the type of coating. In general, the type of coating is intended to attach an organic molecule to the inorganic surface of the electrode. In one embodiment, the coating is attaching a sensor-coupling molecule to the inorganic surface of the electrode. In one embodiment, the coating is incubating the electrode in a solution of sensor-coupling molecule. In one embodiment, the sensor-coupling molecule is thioctic acid. In one embodiment, the electrode is incubated in a 5 mM solution of thioctic acid in ethanol. It is not meant to limit the incubation time for coating electrodes with molecules. Incubation time of electrodes in solutions of coating molecules include but are not limited to a few seconds, a few minutes, 30 minutes, 40 minutes, 45 minutes, up to 1 hour or more. In a preferred embodiment, the electrode is incubated in a 5 mM solution of thioctic acid in ethanol for 30 minutes. It is not intended that the present invention be limited by the type of layering. In general, the type of layering is intended to attach a molecule to the electrode. In one embodiment, the layering is incubating the electrode in a solution of enzyme. In one embodiment, the layering includes but is not limited to dipping, immersing, plunging, and the like, of the electrode into a solution for a specified amount of time. Indeed, layering includes but is not limited to attaching an enzyme-immobilizing molecule to a sensor-coupling molecule and attaching an enzyme to an enzyme-immobilizing molecule. In one embodiment, the layering is incubating the electrode in a solution of sensor-coupling molecule. In one embodiment, the enzyme-immobilizing compound is poly-L-lysine (PLL). In one embodiment, the electrode is incubated in poly-L-lysine solution for 45 minutes. In one embodiment, an enzyme-immobilizing compound is in between the sensor-coupling molecule and tyrosinase. In one embodiment, an enzyme-immobilizing compound is in between tyrosinase and an esterase. In one embodiment, steps c) and d) are repeated at least one time. In one embodiment, steps c) and d) are repeated at least three times. In one embodiment, the esterase enzyme polypeptide is a neuropathy esterase enzyme polypeptide. In one embodiment, the esterase enzyme polypeptide is an acetylcholinesterase enzyme polypeptide. In one embodiment, the esterase enzyme polypeptide is a butyrylcholinesterase enzyme polypeptide.

In some embodiments, the invention provides a method for real-time measuring of esterase activity, comprising, a) providing, i) a device, comprising an amperometric electrode, wherein said amperometric electrode further comprises, a layer of a sensor-coupling molecule, wherein said molecule bridges an inorganic surface of the amperometric electrode to an enzyme immobilizing compound, a bilayer of an enzyme immobilizing compound and an oxidase enzyme, a layer of an enzyme immobilizing compound for attaching an esterase enzyme, and a layer of esterase enzyme, wherein said esterase is a neuropathy target esterase enzyme; ii) a solution of esterase substrate, wherein the esterase substrate is phenyl valerate; b) contacting the electrode with the solution of esterase substrate; and c) measuring neuropathy target esterase enzyme activity in real-time. It is not intended that the present invention be limited by the esterase enzyme. Esterase enzymes include but are not limited to a recombinant human neuropathy target esterase, acetylcholinesterase, and butyrylcholine esterase. In preferred embodiments, said neuropathy target esterase enzyme comprises a neuropathy target esterase activity domain. In some embodiments, said neuropathy target esterase enzyme has esterase activity. In some embodiments, said neuropathy target esterase enzyme is a full-length sequence. In some embodiments, said neuropathy target esterase enzyme is a fragment. In some embodiments, the neuropathy target esterase includes but is not limited to a SEQ ID NO:02, a SEQ ID NO:04, and an amino acid sequence comprising residues 727-1216 of a full-length neuropathy target esterase. In some embodiments, said method for real-time measuring further provides a test sample. In some embodiments, said esterase substrate is added to the test sample. In some embodiments, said esterase substrate is phenyl valerate. In some embodiments, the electrode is a stationary electrode. In some embodiments, the electrode is a rotating disk electrode. In some embodiments, said measuring is an amperometric measurement. In preferred embodiments, the measuring step comprises amplification. In some embodiments, said measuring is proportional to the activity of the esterase. In some embodiments, said method for real-time measuring further comprises an esterase inhibitor, wherein said inhibitor decreases esterase activity. In some embodiments, said decrease in esterase activity is proportional to the concentration of inhibitor. In some embodiments, the method further comprises contacting the electrode with the esterase inhibitor. It is not intended that the present invention be limited by the esterase inhibitor. In some embodiments, the esterase inhibitor includes but is not limited to phenylmethylsulfonyl fluoride, a neurotoxic organophosphate compound, an organophosphate, a carbamate pesticide, and a nerve gas. In some embodiments, said inhibitor is selected from the group consisting of phenylmethylsulfonyl fluoride, Mipafox, organophosphate, and a carbamate pesticide.

In some embodiments, the invention provides a method for detecting a functional alteration of a neuropathy target esterase polypeptide in a subject, comprising: a) providing, i) a subject, ii) a neuropathy target esterase polypeptide from the subject, wherein said polypeptide comprises a neuropathy target esterase domain, and iii) a device, comprising an amperometric electrode, wherein said amperometric electrode further comprises, a layer of a sensor-coupling molecule, wherein said sensor-coupling molecule bridges an inorganic surface of the amperometric electrode to an enzyme immobilizing compound, a bilayer of an enzyme immobilizing compound and an oxidase enzyme, a layer of an enzyme immobilizing compound for attaching a neuropathy target esterase enzyme, and a layer of neuropathy target esterase polypeptide from the subject; and b) measuring the activity of the subject's neuropathy target esterase polypeptide. In some embodiments, the method further comprises providing an electrode comprising a fully functional neuropathy target esterase polypeptide a step after step b) of c) comparing the subject's neuropathy target esterase activity to the activity of fully functional neuropathy target esterase polypeptide. In some embodiments, the method further comprises d) determining whether there is a comparative increase or decrease in esterase activity of the subject's neuropathy target esterase polypeptide compared to the activity of a fully-functional neuropathy target esterase polypeptide. In certain embodiments, the methods further comprise a step after step c), d) determining whether there is a comparative increase or decrease in esterase activity of the subject's neuropathy target esterase polypeptide compared to the activity of a fully-functional neuropathy target esterase polypeptide. It is not meant to limit the type of functional alteration of a neuropathy target esterase polypeptide. Indeed, functional alterations include but are not limited to a decrease in function and an increase in function. In some embodiments, said functional alteration results from a genetic mutation. In some embodiments, said neuropathy target esterase polypeptide from a subject is isolated from a subject's cell or plasma. In some embodiments, said neuropathy target esterase polypeptide from a subject is selected from a group consisting of a translated nucleic acid, tissue, cell, and plasma. In some embodiments, said increase or decrease in esterase activity is indicative of a motor neuron disorder. In some embodiments, the subject is at risk of developing a motor neuron disorder. In some embodiments, said motor neuron disorder. It is not meant to limits the motor neuron disorder. The motor neuron disorder includes but is not limited to amyotrophic lateral sclerosis, autosomal recessive spastic paraplegia, hereditary spastic paraplegia, primary lateral sclerosis, progressive pseudobulbar palsy, progressive muscular atrophy, progressive bulbar palsy, and postpolio syndrome. In some embodiments, said decrease in esterase activity is indicative of a subject's in vivo exposure to an esterase inhibitor.

In some embodiments, the invention provides a method for increasing the sensitivity of biosensors of the present inventions.

DESCRIPTION OF THE FIGURES

FIGS. 3A-3F show-exemplary diagrams and data for immobilization of enzyme, exemplified by tyrosinase, as in FIG. 3 which shows a schematic diagram of a molecular architecture of an electrode assembled with methods used to provide an exemplary NEST biosensor, with the exception that the final NEST layer was not deposited; FIG. 3B shows an exemplary layering (fabrication) of multilayers using consecutive and alternating adsorption of a polyanion followed by a polycation providing a flexible structure of a polyelectrolyte multilayer (PEM) film while avoiding forming a crystalline structure; FIG. 3C shows an exemplary schematic of enzyme reactions in the absence of NEST; FIG. 3D shows a current time response on an electrode coated with tyrosinase without NEST activity in the presence of a phenyl valerate solution; FIG. 3E shows a current time response of a phenol sensor to the addition of aliquots of 4 μM phenol in 0.1 M phosphate buffer, pH 7.0 at an applied potential of −0.1 V (vs Ag/AgCl); FIG. 3F is a calibration plot of FIG. 3E.

FIG. 4A shows an exemplary molecular architecture of a NEST biosensor of the present inventions with 3.5 layers, such as formed on a non-rotating (stationary) electrode. FIG. 4B shows an exemplary bi-enzyme electrode of the present inventions with 3 layers, such as formed on a rotating disk electrode wherein the enzymes consist of NEST and tyrosinase. FIG. 4C shows an exemplary front view of a Rotating Disk Electrode rotator, including motor, speed control, mount for electrode, and rotating disk, and FIG. 4D an exemplary side view of a Rotating Disk Electrode rotator including a mounted Rotating Disk Electrode with a biosensor, a rotating disk, and demonstrating a support arm for mounting the motor and rotating disk. In FIGS. 4A and 4B: the lower rectangle represents the surface of an electrode, the linker molecule is represented by a schematic chemical structure of thiotic acid, ammonium ions are represented by $NH_2$ and $NH_3^+$, whereas the curvy line represents an enzyme immobilizing layer of Poly-L-lysine, an oxidase is represented by a dark curvy open structure, and an esterase is represented by a dark oval, whereas NEST represent a recombinant esterase domain of NTE.

FIG. 8F shows an exemplary response of a biosensor after addition of 8 μM of an ester form of phenyl valerate, followed by 10 of an NTE inhibitor phenylmethylsulfonyl fluoride (PMSF); FIG. 8G shows an exemplary current time response of a NEST biosensor after the addition of 8 μM phenyl valerate followed by the addition of 10 μM of NEST inhibitor PMSF, in 0.1 M phosphate buffer, pH 7.0; FIG. 8H shows an exemplary response of a biosensor after addition of 8 μM of an ester form of phenyl valerate, followed by 100 μM of an NTE inhibitor PMSF; FIG. 8I shows an exemplary current time response of NEST biosensor after the addition of 8 μM phenyl valerate followed by the addition of 100 μM of NEST inhibitor PMSF, in 0.1 M phosphate buffer, pH 7.0; FIG. 8J shows an exemplary response of a biosensor after addition of 8 μM of an ester form of phenyl valerate, followed by 1 mM of an NTE inhibitor PMSF; and FIG. 8K shows an exemplary current time response of NEST biosensor after the addition of 8 μM phenyl valerate followed by the addition of 1000 μM of NEST inhibitor PMSF, in 0.1 M phosphate buffer, pH 7.0.

FIGS. 12A-12E show exemplary sequences for NTE and NEST.

FIG. 14 shows exemplary boundary condition equations relating to the present inventions.

FIG. 15 shows exemplary solution equations relating to the present inventions.

(B) versus the square root of rotation rate for electrode A; (C) shows the Cathodic sensitivity, $S_{ph}{}^{c}$, in the presence of phenol as a function of rotation rate; and (D) shows the Cathodic sensitivity, $S_{pv}{}^{c}$, in the presence of phenyl valerate as a function of rotation rate.

Figure 17A:
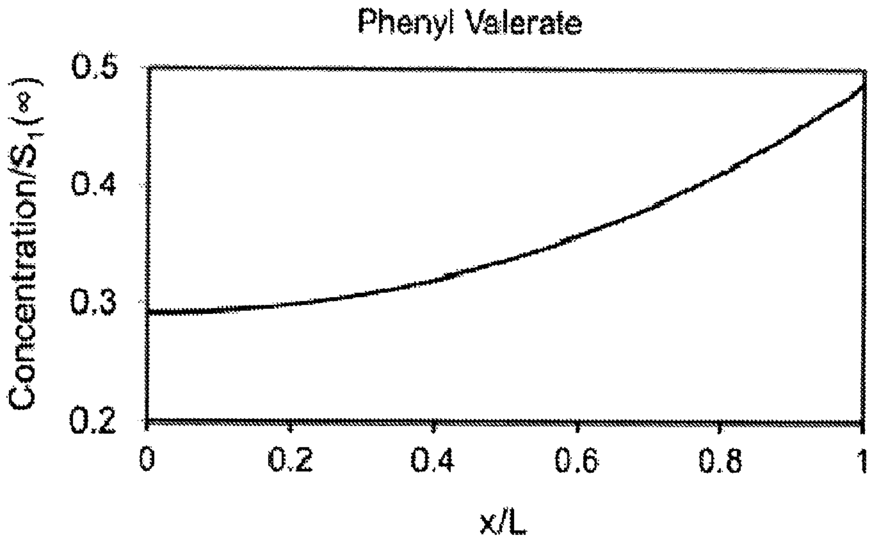
Figure 17B:
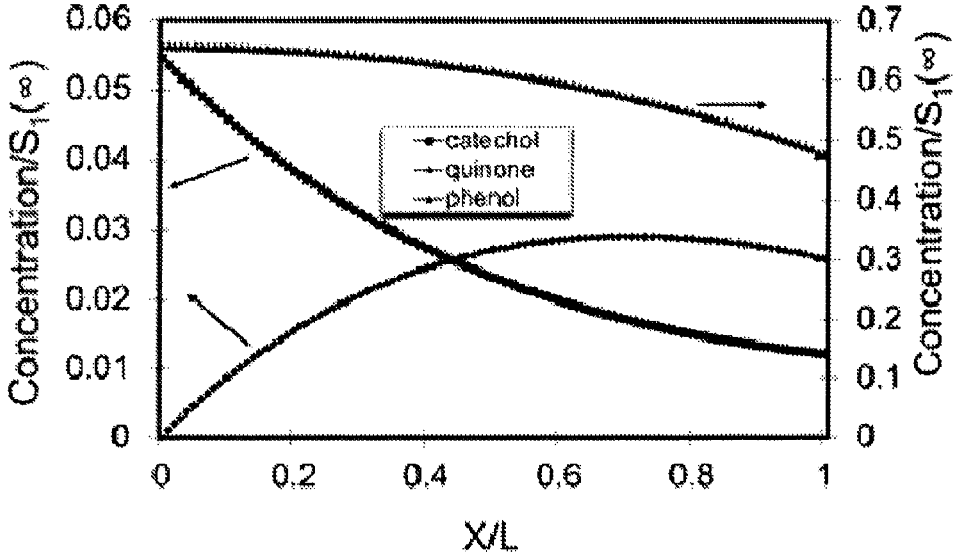
Figure 17C:
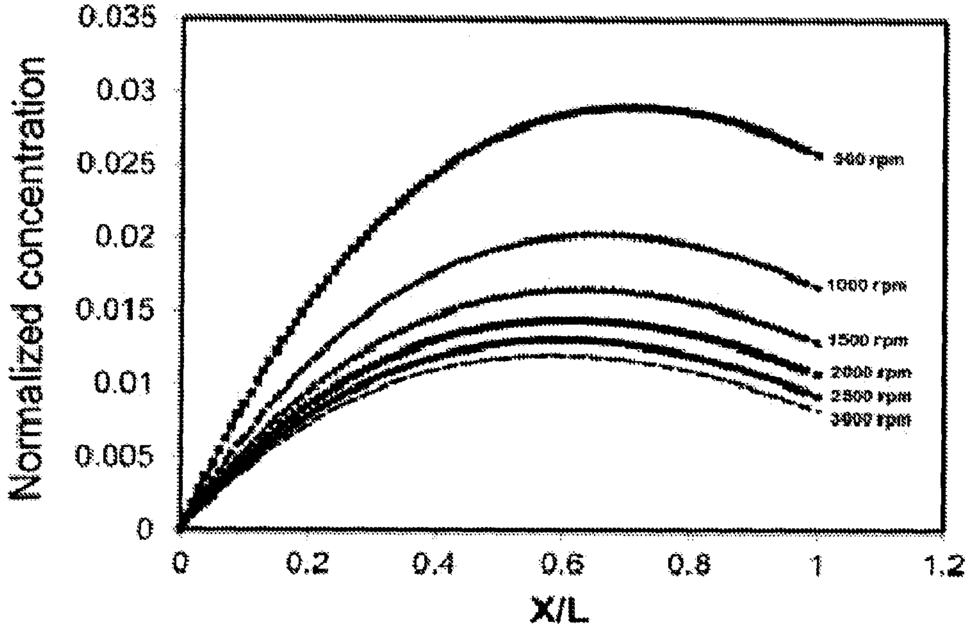
Figure 17D:
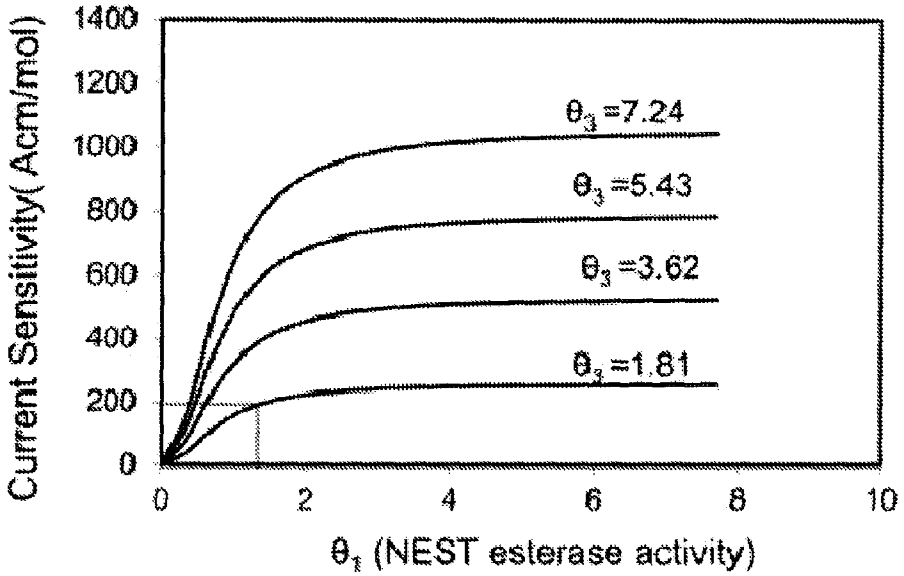

FIGS. 17A-17D show an exemplary concentration profile of phenyl valerate in FIG. 17A; an exemplary concentration profile of phenol, catechol and o-quinone normalized to phenyl valerate bulk concentration ($S_1(\infty)$) as a function of relative position (x/L) within the bi-enzyme interface in FIG. 17B; a Concentration profile of o-quinone normalized to phenyl valerate bulk concentration ($S_1(\infty)$) at various rotation rates in FIG. 17C; and the Current sensitivity, $S_{pv}{}^{c}$, as a function of amount of NEST esterase activity ($\theta_1$) and tyrosinase's catecholase activity ($\theta_3$) in FIG. 17D.

FIG. 18 shows an exemplary signal amplification in bi-enzyme electrode due to the recycling of catechol. For simulation, the following values of these parameters were used $P_m$=0.0091 cm/s, $D_e$=2.2×10$^{-5}$ cm$^2$/s, ω=500 rpm.

DEFINITIONS

To facilitate an understanding of the present invention, a number of terms and phrases are defined below:

The use of the article "a" or "an" is intended to include one or more.

As used in this application, the singular form "a," "an," and "the" include plural references unless the context clearly dictates otherwise. For example, the term "a biosensor" includes a plurality of biosensors, such as a variety of esterase biosensors.

As used herein, the term "Enzyme Commission number" or "E.C. number" or "EC number" or "E.C." or "EC" refers to a numerical classification scheme for enzymes. Each EC number refers to a specific enzyme-catalyzed reaction under one number and a generic name, however each number may include one enzyme or several different enzymes.

As used herein, the term "enzyme" refers to a molecule that acts as a catalyst for a chemical reaction, such that a substrate is converted into a product.

As used herein, the term "chemical reaction" refers to a reaction involving chemical reactants, such as organic compounds.

As used herein, "substrate" or "reactant" refers to a substance that is acted upon by an enzyme during a chemical reaction, such as NTE and NEST enzymes acting upon a phenyl valerate substrate to form a phenol product.

As used herein, "product" refers to a substance that forms as a result of chemical reaction.

As used herein, "solvent" refers to a component of a solution that dissolves a solute.

As used herein, the term "esterase" or "esterase enzyme" refers to an enzyme, such as a protein, that when functional may catalyze the hydrolysis of an ester or a synthetic substrate comprising an ester group. In other words, an esterase refers to a hydrolase enzyme that when functional may split an ester into an acid and an alcohol in a chemical reaction with water, also referred to as E.C. 3.1 an enzyme that acts on an ester bond, and includes such enzymes as carboxylic ester hydrolases (EC 3.1.1); lysophospholipase (EC 3.1.1.5); acetyl esterase (EC 3.1.1.6); acetylcholinesterase (EC 3.1.1.7); and cholinesterase (EC 3.1.1.8).

As used herein, "neuropathy target esterase" or "NTE" or "neurotoxic esterase" or "2-lysophosphatidylcholine acylhydrolase" refers to a lysophospholipase enzyme molecule designated EC 3.1.1.5, such that a NTE molecule is a nucleic acid sequence or a protein sequence. The term "neuropathy target esterase" also refers to a molecule with any one of the following names: lecithinase B; lysolecithinase; phospholipase B; lysophosphatidase; lecitholipase; phosphatidase B; lysophosphatidylcholine hydrolase; lysophospholipase A1; lysophopholipase L2; lysophospholipaseDtransacylase; NTE-LysoPLA; and NTE-lysophospholipase.

Figure 1:
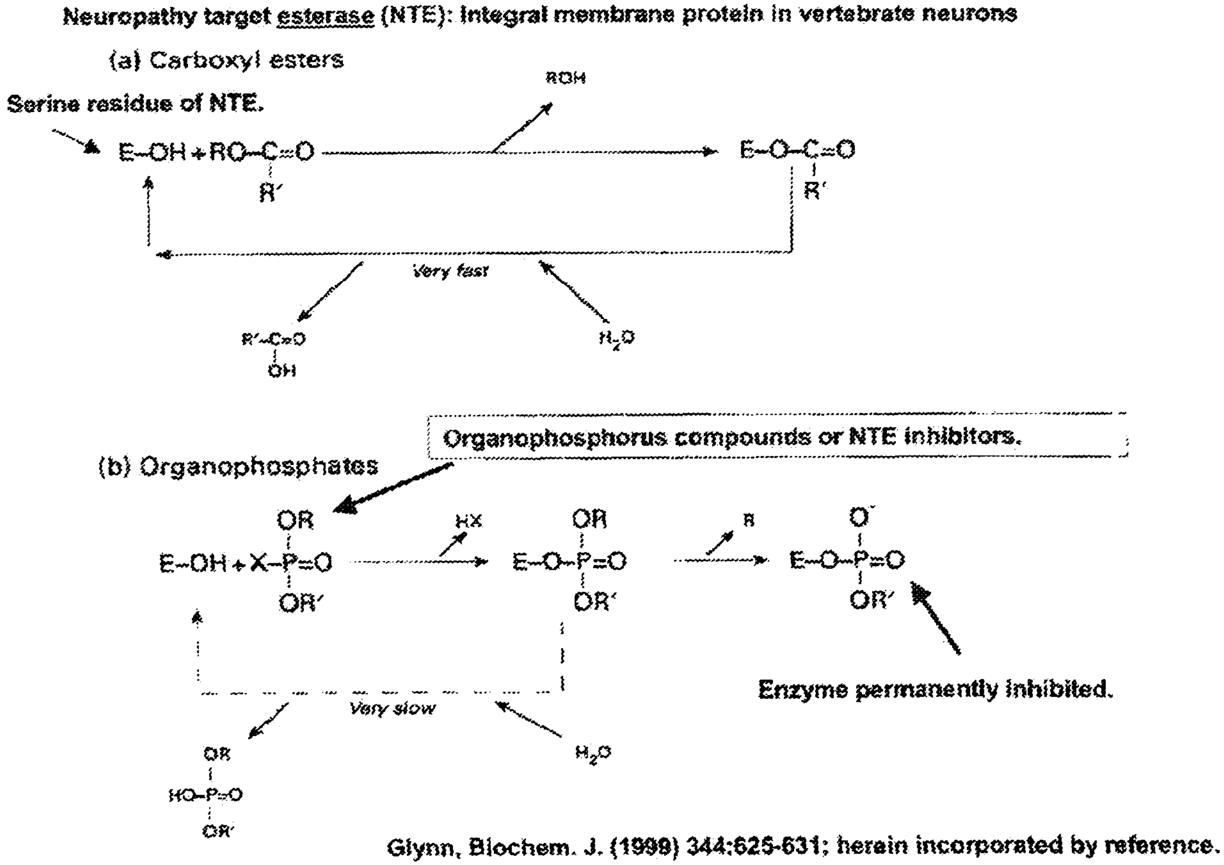
FIG. 1 (Glynn (1999) Biochem. J. 344:625-631, herein incorporated by reference) shows an exemplary schematic diagram of where carboxyl esters (A) and organophosphates and other target neuropathy target esterase (NTE) inhibitors (B) target neuropathy target esterase (NTE) as an integral membrane protein in vertebrate neurons.
Figure 2A:
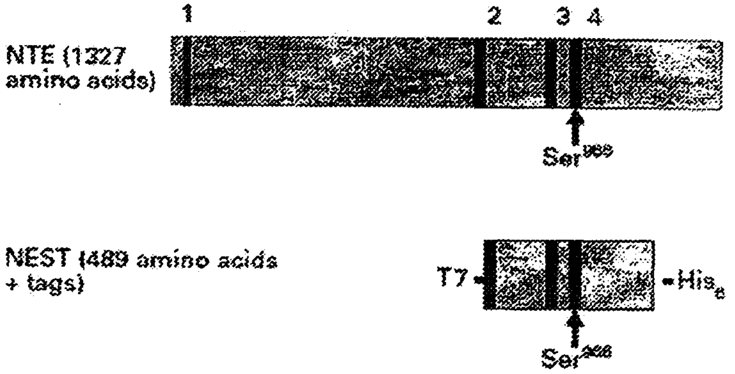
FIGS. 2A-2B show an exemplary schematic diagram (FIG. 2A) of a full-length and expressed recombinant esterase domain of NTE (NEST) of the present invention comprising amino acid residues 727-1216 of NTE with a molecular mass of approximately 47 kDa and an exemplary preliminary purification (FIG. 2B) of recombinant human NTE protein expressed in *E. coli* and concentrated isolated recombinant human NTE protein.

As used herein, "esterase activity domain" or "recombinant esterase domain of NTE" or "NEST" refers to a portion of an NTE molecule comprising a catalytic domain of NTE that in it's wild-type form demonstrates esterase activity, such as serine esterase activity, phenyl valerate hydrolase activity, etc., see, for example, FIG. 2A.

As used herein, "Neuropathy target esterase" or "NEST" when used in reference to a protein or a DNA sequence of the present inventions also refers to a protein sequence or a nucleic acid sequence, respectively, encoding a NTE enzyme of the present inventions. Thus the terms NTE and NEST refer to both nucleic acid sequences and proteins that are identical to a wild-type NTE or a portion thereof, and those that are derived from wild type NTE (e.g., variants of NTE polypeptides of the present invention, such as NEST) or mutants of NTE demonstrating altered esterase activity or chimeric genes constructed with portions of NEST coding regions.

As used herein, the term "tyrosinase enzyme" or "tyrosinase" in reference to a protein, refers to a tyrosinase protein (monophenol monooxygenase) (EC 1.14.18.1) that catalyses the oxidation of phenols (such as phenol, catechol, and the like) or in reference to a nucleic acid refers to a nucleic acid sequence that encodes a tyrosinase protein. Tyrosinase also refers to a molecule with a systemic name of monophenol, L-dopa: oxygen oxidoreductase in addition to a molecule with any one of the following names: phenolase; monophenol oxidase; cresolase; catechol oxidase; polyphenolase; pyrocatechol oxidase; dopa oxidase; chlorogenic oxidase; catecholase; polyphenol oxidase; monophenolase; o-diphenol oxidase; chlorogenic acid oxidase; diphenol oxidase; o-diphenolase; tyrosine-dopa oxidase; o-diphenol:oxygen oxidoreductase; polyaromatic oxidase; monophenol monooxidase; o-diphenol oxidoreductase; monophenol dihydroxyphenylalanine:oxygen oxidoreductase; N-acetyl-6-hydroxytryptophan oxidase; monophenol, dihydroxy-L-phenylalanine oxygen oxidoreductase; o-diphenol:$O_2$ oxidoreductase; phenol oxidase, and the like.

As used herein, "alkaline phosphatase" or "alkaline phosphomonoesterase" or "phosphomonoesterase" or "EC 3.1.3.1" refers to an enzyme for catalyzing a reaction comprising a phosphate monoester and $H_2O$ to form substrates of an alcohol and a phosphate.

The term "wild-type" refers to a gene or gene product, such as a protein, that has the characteristics of that gene or gene product when isolated from a naturally occurring source. A wild-type gene is that which is most frequently observed in a population and is thus arbitrarily designed the "normal" or "wild-type" form of the gene. For the purposes of the present inventions, the normal or wild-type gene codes for a fully functional wild-type gene product, such as an enzyme.

The term "naturally-occurring" as used herein as applied to an object, such as a protein or nucleic acid, refers to the fact that the object can be found in nature. For example, a polypeptide or polynucleotide sequence that is present in an organism (including bacteria) that can be isolated from a source in nature and which has not been intentionally modified by man in the laboratory is a naturally occurring sequence. In contrast, the terms "modified," "mutant," "polymorphism," and "variant" refer to a gene or gene product that displays modifications in sequence and/or functional properties (i.e., altered characteristics) when compared to the wild-type gene or gene product, for example, a varient may be naturally occurring or man-made.

As used herein, the term "ester" refers to an organic compound comprising a functional group —COOR, wherein R is a substitution group, for example an alkyl group. Examples of esters include thioesters (—CSOR) and a product of a condensation reaction (esterification reaction) in which a molecule of an acid united with a molecule of alcohol with the elimination of a molecule of water, and the like. Such an esterification reaction forms an "ester bond."

As used herein, the term "alkyl group" or grammatical equivalents herein is meant a straight or branched chain alkyl group, with straight chain alkyl groups being preferred.

As used herein, "esterase activity" refers to a relative capability of an esterase to catalyze an esterase reaction, such as hydrolysis of an ester bond, for example, the capability of an NTE to catalyze an ester bond or ester-type bond, such as found in a serine ester or phenyl valerate, respectively, and the like. For the purposes of the present inventions, when a protein or enzyme catalyzes a reaction, that protein or enzyme is considered "active." For the purpose of the present inventions, esterase activity in reference to "measuring esterase activity," such as measuring neuropathy target esterase activity refers to obtaining a quantitative value of esterase activity, for example, an amperometric measurement, such that a quantitative value is proportional to the activity of the esterase enzyme.

As used herein, "altering" and grammatical equivalents as used herein in reference to the level of any substance and/or phenomenon, such as voltage, refers to an increase and/or decrease in the quantity of the substance and/or phenomenon, regardless of whether the quantity is determined objectively, and/or subjectively. On the other hand, "altering" in reference to layers refers to changing the compound used from one layer to the next layer.

As used herein, "polycation" refers to a positively charged molecule.

As used herein, "polyanion" refers to negatively charged molecule.

As used herein, "activator" or "mediator" in reference to an enzyme refers to a molecule other than a substrate, that interacts with an enzyme in such a manner as to increase the activity of the enzyme, for example, a protein or a chemical substance, such as 1-methoxyphenazine methosulfate (Sokolovskaya, et al., (2005) Biotechnology Letters, 27 (16): 1211-1218, herein incorporated by reference).

As used herein, "increase" or "elevate" or "raise" and grammatical equivalents when used in reference to the level of a substance and/or phenomenon, such as current, in a first sample or a base-line sample relative to a second sample, wherein the first sample and the second sample may be the same sample or a different sample, refers to a quantity of the substance and/or phenomenon in the second sample that is higher than in the first sample by any amount that may also be statistically significant using any art-accepted statistical method of analysis, for example, an enzyme in a first sample may be less active than an enzyme in a second sample under essentially the same test conditions. In another embodiment, the quantity of substance and/or phenomenon in the second sample is at least 1% higher than the quantity of the same substance and/or phenomenon in a first sample. In another embodiment, the quantity of substance and/or phenomenon in the second sample is at least 10% higher than the quantity of the same substance and/or phenomenon in a first sample. In another embodiment, the quantity of the substance and/or phenomenon in the second sample is at least 20% higher than the quantity of the same substance and/or phenomenon in a first sample. In another embodiment, the quantity of the substance and/or phenomenon in the second sample is at least 23% higher than the quantity of the same substance and/or phenomenon in a first sample. In yet another embodiment, the quantity of the substance and/or phenomenon in the second sample is at least 70% higher than the quantity of the same substance and/or phenomenon in a first sample. In yet another embodiment, the quantity of the substance and/or phenomenon in the second sample is at least 72% higher than the quantity of the same substance and/or phenomenon in a first sample. In a further embodiment, the quantity of the substance and/or phenomenon in the second sample is at least 75% higher than the quantity of the same substance and/or phenomenon in a first sample. In yet another embodiment, the quantity of the substance and/or phenomenon in the second sample is at least 90% higher or more than the quantity of the same substance and/or phenomenon in a first sample.

Figure 8:
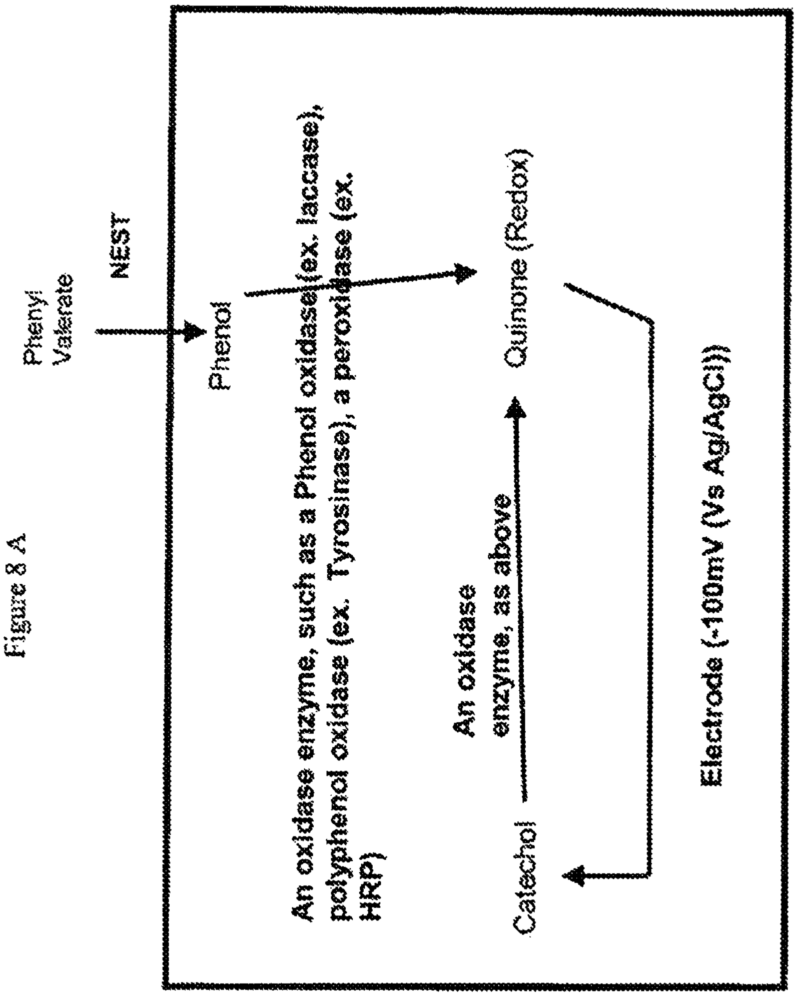
FIGS. 8A-8K show exemplary examples of schematic of enzyme reactions in FIG. 8A; a current time response of the NEST biosensor to the addition of aliquots of 8 μM catechol in 0.1 M phosphate buffer, pH 7.0 at an applied potential of −0.1 V (vs Ag/AgCl) in FIG. 8B, and in FIG. 8C a calibration plot of the data in FIG. 8B; a current time vs. response of a NEST biosensor after the addition of aliquots of 4 μM phenyl valerate, in 0.1 M phosphate buffer, pH 7.0, at an applied potential of −0.1 V vs. Ag/AgCl reference electrode in FIG. 8D, and a calibration plot for FIG. 8D in FIG. 8E.
Figure 8B:
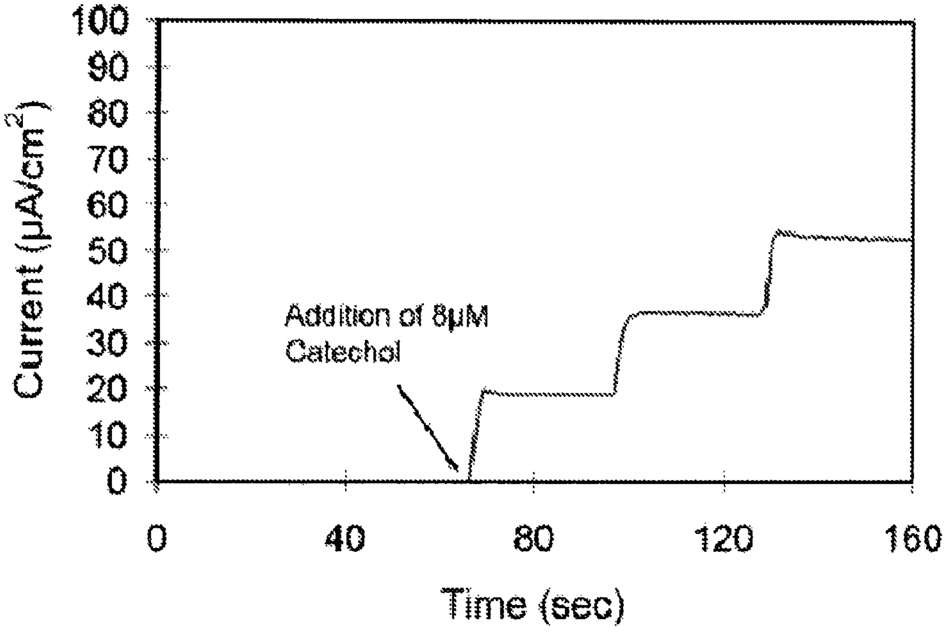
Figure 8C:
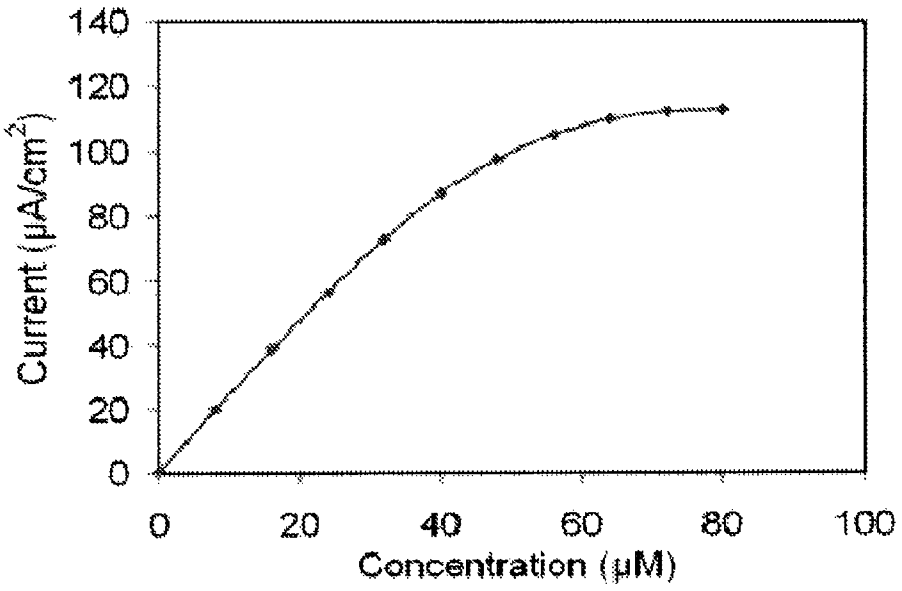
Figure 8D:
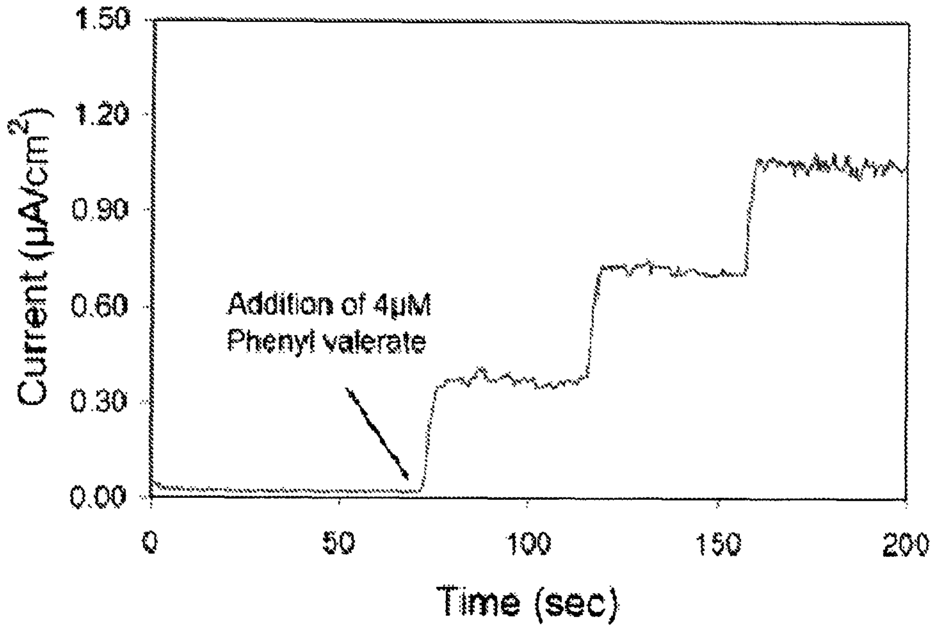

As used herein, "increase" and grammatical equivalents in reference to an activity, for example, "increase in esterase activity" or "increase in catalytic activity" or "increase in enzyme activity" refers to a higher amount of activity in a second sample compared to a first sample or baseline sample, for example, when NTE activity in a first sample is measured prior to and then in the presence of an NTE substrate in a second sample, such that the measured esterase activity of NTE in the presence of a substrate is higher than the activity of the NTE without the substrate, sec, for example, FIG. 8D. Another example is a comparison of NTE activity of a biosensor comprising a mutant NTE compared to a biosensor comprising a wild-type NTE enzyme, wherein the mutation increases the esterase activity of NTE when compared to the esterase activity of the wild-type enzyme. Another example of increasing esterase activity refers to a first measurement of a substance and/or phenomenon in a sample relative to a second measurement of the same sample, for example, a first current measurement of a sample relative to a second current measurement of the same sample after the addition of a substrate, wherein the quantity of the substance and/or phenomenon in the second measurement is higher than the first measurement by any amount that is determined as significant, for example, increased by at least 1 $\mu A/cm^2$, 2 $\mu A/cm^2$, 10 $\mu A/cm^2$, or 20 $\mu A/cm^2$, etc., or increased by at least 0.1 μA, 0.2 μA, 0.3 μA, 0.4 μA, etc., and the like. Additionally, "increase" and grammatical equivalents in reference to a quantity, such as a measurement demonstrating an increase in activity of the substance and/or phenomenon refers to any quantity that demonstrates a statistically significant increase over another using any art-accepted statistical method of analysis.

As used herein, "inhibitor" in reference to an enzyme refers to a molecule or a chemical substance that interacts with an enzyme in such a manner as to decrease the activity of the enzyme, for example, an inhibitor of NTE or NEST refers to phenylmethylsulfonyl fluoride (PMSF), Mipafox, organophosphate, carbamate pesticide, and the like.

As used herein, "decrease," "reduce," "inhibit," "diminish," "suppress," and grammatical equivalents when used in reference to the level of a substance and/or phenomenon, such as current, in a first sample or base line sample relative to a second sample, wherein the first sample and the second sample may be the same sample or a different sample, refers to a quantity of the substance and/or phenomenon in the second sample that is lower than in the first sample by any amount that may also be statistically significant using any art-accepted statistical method of analysis, for example, an enzyme in a second sample may be less active than an enzyme in a first sample under essentially the same test conditions. In another embodiment, the quantity of substance and/or phenomenon in the second sample is at least 1% lower than the quantity of the same substance and/or phenomenon in a first sample. In another embodiment, the quantity of substance and/or phenomenon in the second sample is at least 10% lower than the quantity of the same substance and/or phenomenon in a first sample. In another embodiment, the quantity of the substance and/or phenomenon in the second sample is at least 20% lower than the quantity of the same substance and/or phenomenon in a first sample. In another embodiment, the quantity of the substance and/or phenomenon in the second sample is at least 23% lower than the quantity of the same substance and/or phenomenon in a first sample. In yet another embodiment, the quantity of the substance and/or phenomenon in the second sample is at least 70% lower than the quantity of the same substance and/or phenomenon in a first sample. In yet another embodiment, the quantity of the substance and/or phenomenon in the second sample is at least 72% lower than the quantity of the same substance and/or phenomenon in a first sample. In a further embodiment, the quantity of the substance and/or phenomenon in the second sample is at least 75% lower than the quantity of the same substance and/or phenomenon in a first sample. In yet another embodiment, the quantity of the substance and/or phenomenon in the second sample is at least 90% lower or more than the quantity of the same substance and/or phenomenon in a first sample.

As used herein, "inhibit," or "decrease," and grammatical equivalents in reference to an activity, for example, "inhibiting esterase activity" or "decreasing in esterase activity" or "decrease in esterase activity" or "decrease in catalytic activity" or "decrease in enzyme activity" refers to a lower amount of activity in a second sample compared to a first sample or baseline sample, for example, when NTE activity is measured prior to and then in the presence of an NTE inhibitor, such that the measured activity in the presence of an inhibitor is less than the activity of the NTE without the inhibitor, see, for example, FIG. 8F-8K. Another example is a comparison of NTE activity of a biosensor comprising a mutant NTE compared to a biosensor comprising a wild-type NTE enzyme, wherein the mutation decreases the esterase activity of NTE when compared to the esterase activity of the wild-type enzyme. Another example of decreasing esterase activity refers to a first measurement of a substance and/or phenomenon in a sample relative to a second measurement of the sample after the addition of a substance, such as a first current measurement of a sample relative to a second current measurement of a sample after the addition of an inhibitor, wherein the quantity of the substance and/or phenomenon in the second measurement is lower than the first measurement by any amount that is determined as significant, for example, decreased by at least 1 $\mu A/cm^2$, 2 $\mu A/cm^2$, 10 $\mu A/cm^2$, 20 $\mu A/cm^2$, etc., or decreased by at least 0.1 μA, 0.2 μA, 0.3 μA, 0.4 μA, etc., and the like. Alternatively, "decrease" and grammatical equivalents in reference to the quantity, such as a measurement of activity, of the substance and/or phenomenon refers to any quantity that is statistically significant using any art-accepted statistical method of analysis. Additionally, "decrease" and grammatical equivalents in reference to a quantity, such as a measurement demonstrating a decrease in activity of the substance and/or phenomenon refers to any quantity that demonstrates a statistically significant decrease over another using any art-accepted statistical method of analysis.

As used herein, the term "cholinesterase" refers to a protein or a gene encoding a protein, or fragments thereof, that can catalyze the hydrolysis of acetylcholine into choline and acetic acid, in addition to hydrolysis reactions of choline esters and the like, designated EC 3.1.1.8. Cholinesterase also refers to a molecule with a systemic name of acylcholine acylhydrolase, in addition to a molecule with any one of the following names: pseudocholinesterase; butyrylcholine esterase; non-specific cholinesterase; choline esterase II; benzoylcholinesterase; choline esterase; butyrylcholinesterase; propionylcholinesterase; anticholineesterase; butyrylcholinesterase; BtChoEase, butylcholinesterase, BuChE, and the like. For the purposes of the present inventions, cholinesterase in reference to a human, such as the term "human cholinesterase" also encompasses the terms "true cholinesterase" and "pseudocholinesterase." The term cholinesterase also refers to mutants and variants of a cholinesterase enzyme or gene encoding a cholinesterase enzyme.

As used herein, the term "acetylcholinesterase" or "AchE" refers to a protein that catalyzes the hydrolysis of acetic esters, such as serine esters, acetic esters in acetylcholine, and catalyzes transacetylations, also designated EC 3.1.1.7. Acetylcholinesterase also refers to a molecule with a systemic name of acetylcholine acetylhydrolase, true cholinesterase; choline esterase I; cholinesterase; acetylthiocholinesterase; acetylcholine hydrolase; acetyl β-methylcholinesterase; AcCholE, and the like.

As used herein, the terms "butyrylcholinesterase" or "BChE" or "BuChE" or "pseudocholinesterase" or "plasma cholinesterase" or "liver cholinesterase" refers to an enzyme, also designated EC 3.1.1.8, that catalyze the hydrolysis of the neurotransmitter acetylcholine into choline and acetic acid. As used herein, the terms "butylcholinesterase" and "butyrylcholinesterase" are used interchangeably.

As used herein, acetylcholinesterase reactivity overlaps with butyrylcholinesterase such that while both catalyze substrates acetylcholine and butyrylcholine under essentially the same conditions, wherein the former hydrolyses acetylcholine faster than the latter, while the latter hydrolyses butyrylcholine faster than the former.

As used herein, the term "neuropathic" refers to a diseased condition of the nervous system induced in vivo or in vitro.

As used herein, the term "cholinesterase inhibitor" or "anticholinesterase" or "anticholinesterase agent" or "anticholinesterase" refers to a chemical or compound that is known to or shown to reduce the activity of a cholinesterase, such as a pesticide, nerve agent, neurotoxin, and the like. A cholinesterase inhibitor may directly reduce the activity of a cholinesterase, for example, organophosphate, organophosphate pesticide, chlorinated derivatives of nicotine, imidacloprid, fipronil, etc., or indirectly reduce the activity of a cholinesterase, for example, some non-organophosphates, glyphosate, fosetyl aluminium, carbamate, carbamate insecticide, such as aldicarb (Temik™); bendiocarb (Ficam™); bufencarb; carbaryl (Sevin™); carbofuran (Furadan™); formetanate (Carzol™); methiocarb (Mesurol™); methomyl (Lannate™, Nudrin™); oxamyl (Vydate™); pinmicarb (Pirimor™); and propoxur (Baygon™), et cetera.

As used herein, the term "neuropathic" in reference to "organophosphorus" or "organophosphate" refers to that organophosphate's effect on the nervous system, for example, an organophosphate may have a neuropathic effect on the nervous system by inhibiting NTE activity, for example, di-isopropyl-uorophosphate, DFP. Alternatively "non-neuropathic" in reference to an organophosphate refers to an effect that does not directly involve the nervous system. As used herein, a chemical that is considered a non-neuropathic compound may have a role in inhibiting NTE activity, for example, paraoxon, OPs, carbamates (CAs), sulfonyl fluorides.

As used herein, the term "organophosphate" or "OP" in reference to a compound as in an "organophosphorus compound" or "organophosphate compound" or "OP compound" refers to an organic compound comprising phosphorus, examples of organophosphates include, but are not limited to, a derivative of a phosphoric compound, for example, an ester of phosphoric acid, pyrophosphoric acid, and similar acids, and the like, Azinphos methyl, carbamate, carbophenothion, Chlorpyrifos, ciodrin, coumaphos, dimefox, Diazinon, disulfoton, dimethoate, dichlorvos, dioxathion, donepezil, also known as E2020, Edrophonium, ethyl p-nitrophenyl thionobenzenephosphonate, hexaethyl tetraphosphate, Mipafox, Methyl parathion, malathion, metrifonate, phorate, ronnel, ruelene, Phosmet, supona, Tacrine, also known as tetrahydroaminoacridine (THA), tetraethyl pyrophosphate, octamethylpyrophosphoramide, parathion, trichlorfon, paraoxon, potasan, schradan, sevin, dimeton, and chemical warfare agents (for example, satin, soman, tabun, cyclohexyl methylphosphonofluoridate, O-ethyl S-diisopropylaminomethyl methylphosphonothiolate), physostigmine, neostigmine; pyridostigmine, ambenonium, emarcarium, rivastigmine, Phenanthrine derivatives; galantamine, Piperidines, et cetera. Organophosphates are found in insecticides, herbicides, nerve gases, solvents, plasticizers, extreme pressure additives, et cetera. Common OPs found in environmental samples include examples such as acephate (Orthene); Aspon; azinphos-methyl (Guthion); carbofuran (Furadan, F formulation); carbophenothion (Trithion); chlorfenvinphos (Birlane); chlorpyrifos (Dursban, Lorsban); coumaphos (Co-Ral); crotoxyphos (Ciodrin, Ciovap); crufomate (Ruelene); demeton (Systox); diazinon (Spectracide); dichlorvos (DDVP, Vapona); dicrotophos (Bidrin); dimethoate (Cygon, De-Fend); dioxathion (Delnav); disulfoton (Di-Syston); EPN; ethion; ethoprop (Mocap); famphur fenamiphos (Nemacur); fenitrothion (Sumithion); fensulfothion (Dasanit); fenthion (Baytex, Tiguvon); fonofos (Dyfonate); isofenfos (Oftanol, Amaze); malathion (Cythion); methamidophos (Monitor); methidathion (Supracide); methyl parathion; mevinphos (Phosdrin); monocrotophos (Azodrin); naled (Dibrom); oxydemeton-methyl (Meta systox-R); parathion (Niran, Phoskil); phorate (Thimet); phosalone (Zolonc); phosmet (Imidan, Prolate); phosphamidon (Dimecron); temephos (Abate); tetraethyl pyrophosphate, TEPP; terbufos (Counter); tetrachlorvinphos (Rabon, Ravap); and trichlorfon (Dylox, Neguvon).

As used herein, the term "chemical warfare" refers to use or intended use of a substance in a military operation in order to kill or injure or incapacitate a person or population. Examples of chemicals that have been or may be used in chemical warfare include, but are not limited to, agents capable of irreversibly binding with cholinesterase, for an example, sarin.

As used herein, the term "organophosphate toxicity symptom" or "organophosphate symptom" or "organophosphate toxicity clinical symptom" or "chemical warfare symptom" refers to a symptom in a subject exposed to an organophosphate or neuropathic chemical, for example, such a symptom may include any one of excess salivation, lacrimation, abdominal pain, vomiting, intestinal hypermotility, diarrhea, bronchoconstriction, an increase in bronchial secretion, involuntary irregular, violent muscle contractions, weakness of voluntary muscles, respiratory failure, weight loss, muscular weakness, pulmonary edema, asphyxia, gastroenteritis, seizure, kidney degeneration, liver degeneration, et cetera.

As used herein, the term "neurotoxin" refers to a substance or "toxin" that causes damage to a nerve or nerve tissue, for example, a snake venom, nerve gas, Sarin, VX, OP compounds, and the like.

As used herein, the term "venom" refers to a toxin secreted by an organism. The term "venom" in reference to snake refers to any poison secreted by a snake.

As used herein, the term "sarin" or "GB" or "O-Isopropyl methylphosphonofluoridate" or "methylphosphonofluoridic acid" or "1-methylethyl ester" "or" $C_4H_{10}FO_2P$" refers to a synthetic compound that inhibits the activity of a cholinesterase.

As used herein, the term "nerve agent" refers to a compound that affects a neuronal cell, for example, sarin, soman, tabun, VX, and the like.

As used herein, the term" "SLUD" or "SLUDGE" refers to a mnemonic that lists symptoms of organophosphate poisoning in a subject that includes any one of Salivation, Lacrimation, Urination, Defecation, Gastrointestinal upset, Emesis, et cetera.

As used herein, the terms "subject" or "patient" refers to any animal, such as a mammal like a dog, cat, bird, livestock, and preferably a human. Specific examples of "subjects" and "patients" include, but are not limited to, individuals not exposed to an esterase inhibitor, individuals exposed to an esterase inhibitor, individuals with functional esterase enzyme activity, individuals with altered esterase enzyme activity, individuals without a motor neuron disorder, individuals with a motor neuron disorder, and individuals with motor neuron disorder-related characteristics or symptoms.

As used herein, the term "motor neuron disorder" refers to disorders of the motor nerves of the brain and/or spinal chord, including, but not limited to progressive deterioration of the motor nerves in the spinal chord and/or brain. Examples of motor neuron disorders include, but are not limited to, amyotrophic lateral sclerosis, hereditary spastic paraplegia (HSP), primary lateral sclerosis, progressive pseudobulbar palsy, progressive muscular atrophy, progressive bulbar palsy, and postpolio syndrome.

As used herein, the phrase "symptoms of motor neuron disorder" and "characteristics of motor neuron disorder" include, but are not limited to, lower extremity weakness, bladder disturbance, impaired position sense in the legs, and neurologic deficits, such as a decrease in the function of the brain, spinal cord, muscles, and/or nerves, for example, inability to speak, decreased sensation, loss of balance, weakness, cognitive dysfunction, visual changes, abnormal reflexes, and problems walking.

As used herein, the term "instructions for using said kit for said detecting the presence or absence of a variant NTE nucleic acid or polypeptide in said biological sample" includes instructions for using the reagents contained in the kit for the detection of variant and wild type NTE nucleic acids or polypeptides.

The term "gene" refers to a nucleic acid (e.g., DNA) sequence that comprises coding sequences necessary for the production of a polypeptide, RNA (e.g., including but not limited to, mRNA, tRNA and rRNA) or precursor (e.g., NTE). The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both eDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "NTE gene" or "NTE genes" refers to the full-length NTE nucleic acid sequence (e.g., SEQ ID NO:3). However, it is also intended that the term encompass fragments of the NTE sequences, mutants of the NTE sequences, as well as other domains within the full-length NTE nucleic acid sequences (e.g., SEQ ID NO:1). Furthermore, the term "NTE nucleic acid sequence" or "NTE polynucleic acid sequence" or "NTE nucleotide sequence" or "NTE polynucleotide sequence" encompasses DNA sequences, cDNA sequences, RNA (e.g., mRNA) sequences, and associated regulatory sequences.

Where "amino acid sequence" is recited herein to refer to an amino acid sequence of a naturally occurring protein molecule, the term "amino acid sequence" and like terms, such as "polypeptide" or "protein" are not meant to limit the amino acid sequence to the complete, native amino acid sequence associated with the recited protein molecule and includes a portion or fragment thereof.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," mean a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the terms "complementary" or "complementarity" are used in reference to polynucleotides (i.e., a sequence of nucleotides) related by the base-pairing rules. For example, for the sequence 5'-A-G-T-3', is complementary to the sequence 3'-T-C-A-5'. Complementarity may be "partial," in which some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Complementarity can include the formation of base pairs between any type of nucleotides, including non-natural bases, modified bases, synthetic bases and the like.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, the term "genetic variation information" or "genetic variant information" refers to the presence or absence of one or more variant nucleic acid sequences (e.g., polymorphism or mutations) in a given allele of a particular gene (e.g., a NTE gene of the present invention).

As used herein, the term "detection assay" refers to an assay for detecting the presence or absence of variant nucleic acid sequences (e.g., polymorphisms or mutations) in a given allele of a particular gene (e.g., a NTE gene). Examples of suitable detection assays include, but are not limited to, those described below in the Examples.

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (for example, in the presence of nucleic acids and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target" refers to a nucleic acid sequence or protein or substance to be detected or characterized.

As used herein, the term "amplification reagents" refers to those reagents (deoxyribonucleotide triphosphates, buffer, etc.) needed for amplification except for primers, nucleic acid template, and the amplification enzyme. Typically, amplification reagents along with other reaction components are placed and contained in a reaction vessel (for example, a test tube, microwell, etc.).

As used herein, the term "amplification" in reference to a signal refers to "signal amplification" comprising measuring enzyme activity as an electrical current generated by the electrode in proportion to the amount of o-quinone generated.

As used herein, the terms "restriction endonucleases" and "restriction enzymes" refer to bacterial enzymes, each of which cut double-stranded DNA at or near a specific nucleotide sequence.

The term "purified" refers to molecules, either nucleic or amino acid sequences that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

As used herein, the term "purified" or "to purify" also refers to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample. For example, recombinant NEST polypeptides are expressed in bacterial host cells and the polypeptides are purified by the removal of host cell proteins; the percent of these recombinant polypeptides is thereby increased in the sample, see Examples.

As used herein, "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucletide" is therefore a substantially purified polynucleotide. An "isolated polypolypeptide" is therefore a substantially purified polypolypeptide.

As used herein, "host cell" refers to any cell capable of replicating and/or transcribing and/or translating a heterologous gene, such as an *E. coli* cell of the present inventions. A "host cell" further includes an individual cell or cell culture which can be or has been a recipient for vector(s) or for incorporation of nucleic acid molecules and/or proteins. Host cells include progeny of a single host cell, and the progeny may not necessarily be completely identical (in morphology or in genomic of total DNA complement) to the original parent cell due to natural, accidental, or deliberate mutation. In some embodiments, a host cell is any microorganism. A host cell includes cells transfected in vivo with a polynucleic acid(s) of this invention.

The term "transfection" refers to the introduction of foreign DNA into a cell. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, bacterial infection, viral infection, for example, phage virus infection, biolistics (i.e., particle bombardment), and the like. The terms "transfect" and "transform" (and grammatical equivalents, such as "transfected" and "transformed") are used interchangeably herein.

The term "stable transfection" or "stably transfected" refers to the introduction and integration of foreign DNA into the genome of the transfected cell.

The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes.

The term "transient transfectant" refers to cells that have taken up foreign DNA but have failed to integrate this DNA.

As used herein, "recombinant protein" or "recombinant polypeptide" refers to a protein molecule that is expressed from a recombinant DNA molecule.

As used herein, the term "recombinant DNA molecule" refers to a DNA molecule that is comprised of segments of DNA joined together by means of molecular biological techniques, such as joining a cDNA with an expression vector.

As used herein, "portion" when in reference to a protein (as in "a portion of a given protein") refers to fragments of that protein. The fragments may range in size from four amino acid residues to the entire amino acid sequence minus one amino acid.

As used herein, "nucleic acid sequence" as used herein refers to an oligonucleotide, nucleotide or polynucleotide, and fragments or portions thereof, and to DNA or RNA of genomic or synthetic origin that may be single- or double-stranded, and represent the sense or antisense strand. Similarly, "amino acid sequence" as used herein refers to peptide or protein sequence.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Those vectors that include a prokaryotic replicon can also include a prokaryotic promoter region capable of directing the expression of a NTE or NEST gene in a host cell, such as *E. coli*. An example of an *Escherichia coli* expression vector used herein is a pET21b vector (Novagen). Eukaryotic cells are known to utilize promoters, enhancers, termination and polyadenylation signals.

The term "prokaryotic replicon" as used herein refers to a DNA sequence having the ability to direct autonomous replication and maintenance of the recombinant DNA molecule extrachromosomally in a prokaryotic host cell transformed therewith. Such replicons are well known in the art.

As used herein, the term "regulatory element" or "transcriptional regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, et cetera.

The term "regulatory region" refers to a gene's 5' transcribed but untranslated regions, located immediately downstream from the promoter and ending just prior to the translational start of the gene, and may also be found in untranslated regions between the translational start and a 3' end in addition to the untranslated region downstream of the 3' end, for example, enhancing regions or elements.

The terms "promoter element," "promoter," or "promoter sequence" refer to a DNA sequence that is located at the 5' end (i.e. precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA. Promoter sequences compatible with bacterial hosts are typically provided in plasmid vectors containing one or more convenient restriction sites for insertion of a contemplated DNA segment. Typical of such vector plasmids are pET21b vector (Novagen), pUC8, pUC9, and pBR329 available from Biorad Laboratories, (Richmond, Calif.) and pPL and pKK223-3 available from Pharmacia (Piscataway, N.J.).

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987, herein incorporated by reference).

The term "promoter region" refers to the region immediately upstream of the coding region of a DNA polymer, and is typically between about 500 bp and 4 kb in length, and is preferably about 1 to 1.5 kb in length.

In addition to a promoter sequence, the expression cassette and the expression vector should also contain a transcription termination region downstream of the structural gene to provide for efficient termination. The termination region may be obtained from the same gene as the promoter sequence or may be obtained from different genes.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The terms "prokaryote" and "prokaryotic" are used in it's broadest sense. A prokaryote includes, but is not limited to, any organism without a distinct nucleus. Examples of prokaryotes include but are not limited to bacteria, blue-green algae, archaebacteria, actinomycetes and mycoplasma.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are gram negative or gram positive. "Gram negative" and "gram positive" refer to staining patterns with the Gram-staining process that is well known in the art. (See e.g., Finegold and Martin, Diagnostic Microbiology, 6th Ed., C V Mosby St. Louis, pp. 13-15 [1982], herein incorporated by reference). "Gram positive bacteria" are bacteria that retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red.

As used herein the term "microorganism" refers to a microscopic organism and taxonomically related macroscopic organisms within the categories of algae, bacteria, fungi (including lichens), protozoa, viruses, and subviral agents.

As used herein, the term "attach" or "attached" in reference to attaching molecules to each other and attaching molecules to the surface of a device refers to the adherence of one molecule to another molecule or the adherence of molecules to an inorganic surface. For the purposes of the present inventions attaching a molecule to an electrode may occur directly or indirectly, for example, a sensor-coupling molecule may be attached directly to an inorganic surface of an electrode whereas an enzyme may be attached indirectly to an electrode by attaching the enzyme to other molecules that in tum are attached to the electrode. Attachment of molecules to each other and molecules to inorganic surfaces may be accomplished by a variety of methods, such as by forming covalent bonds, entrapment, and the like.

As used herein, "enzyme immobilizing" in reference to a compound or agent or carrier or molecule refers to a substance that attaches an enzyme to a biosensor of the present inventions. Examples of an enzyme immobilizing compound includes any covalent bond forming compound, such as a cross-linking compound (e.g., via glutaraldehyde), an entrapment compound, a sensor-coupling molecule, and the like.

As used herein, "covalently attached" refers to the attachment of at least two moieties by at least one bond, for example, a sigma bond, a pi bond, a coordination bond, and the like.

As used herein, the term "covalent bond forming compound" refers to a molecule forming a chemical bond that results in the sharing of one or more pairs of electrons (e.g. amide bonds), such as a cross-linking compound a linker molecule, a spacer molecule, an entrapment compound, a sensor-coupling molecule, and the like.

As used herein, the term "entrapment" in reference to a compound refers to a substance that attaches a protein to a biosensor interface or holds a protein, such as a polymer matrix, for example polyacrylamide, polyelectrolytes, polystyrene, and et cetera.

As used herein, the term "displaying" in reference to an enzyme, such as a neuropathy target esterase enzyme, refers to a variety of techniques used to interpret the presence of that enzyme. Displaying includes, but is not limited to, ellipsometry measurements, Faradaic impedance spectra, current versus time response in the presence of a substrate, current versus time response in the presence of a substrate and an inhibitor, voltammetry, table, chart, et cetera.

As used herein, the term "biosensor interface" in reference to an electrode refers to the area encompassing the organic portion of a biosensor in contact with the inorganic electrode surface. A biosensor interface in reference to an organic portion of a biosensor refers to the area where the organic portion is in contact with a test sample.

As used herein, the term "biomimetic interface" refers to a structure that mimics a cell membrane, also referred to as an artificial cell membrane. The term "biomimetic interface" in reference to nanostructured refers to a structure comprised of at least one layer whose thickness is measured in nanometers.

As used herein, "sensor-coupling" in reference to any one of a compound or agent or carrier or molecule or coating refers to a substance that acts to bridge organic and inorganic molecules, also referred to as a "spacer molecule" for bridging organic and inorganic surfaces. Such sensor-coupling molecules form stable bonds, such as covalent bonds, between organic and inorganic molecules, examples of coupling molecules include, thioctic acid, thioctic acid derivatives such as 2-aminoethyl-D-mannopyranoside; 2-aminoethyl-1,3-D-mannopyranosyl(-1,6-D-mannopyranosyl)-D-mannopyranoside, thiourea, 3-mercaptopropionic acid, and the like, organosilicon compounds, silanes such as amino, epoxy, acrylate, methacrylate, mercapto, vinyl silanes, such as 3-Acryloxypropyl)trimethoxysilane, N-(2-Aminoethyl)-3-aminopropyltrimethoxysilane, 3-Aminopropyltriethoxysilane, 3-Aminopropyltrimethoxysilane, 3-Isocyanatopropyltriethoxysilane, 3-Glycidoxypropyl)trimethoxysilane, 3-Mere aptopropyltrimethoxysilane, 3-Methacryloxypropyltrimethoxysilane, Vinyltrimethoxysilane (Gelest, Inc.) silanes and the like. For the purposes of the present inventions, a sensor-coupling molecule attaches an organic enzyme to an inorganic electrode surface.

As used herein, "biosensor" refers to a general designation that encompasses a sensor wherein a binding ligand, for example an enzyme, is attached to an electrode. A biosensor in reference to a measuring device refers to a biological interface (for example, an enzyme, cell layer, etc.) coupled to a transducer (for example, a gold electrode, an oxygen-type electrode, a carbon composite electrode, a tyrosinase electrode, (for example, Sokolovskaya et al., Biotechnol Lett. 2005 August; 27 (16):1211-8; Makhaeva et al, J Toxicol Environ Health A. 2003 Apr. 11; 66 (7):599-610; herein incorporated by reference in their entirety), etc.). For the purposes of the present inventions, "biosensor" in reference to an electrode, refers to an analytical device for converting a biological response into an electrical signal, for example, amperometric, calorimetric, potentiometric, optical, piezo-electric, et cetera. In one preferred embodiment, the electrical signal is amperometric.

As used herein, the term "amperometric" refers to the measurement of an electric current flowing under an applied potential difference between two electrodes in contact with an electrolyte. Amperometric in reference to an electrochemical analysis refers to a detected or measured current that in turn is proportional to the concentration of the species generating the current. Amperometric in reference to an electrode, such as "amperometric electrode" or "amperometric biosensor" refers to an electrode wherein electron transfer occurs at the surface of an electrode and generates a current, for example, a "working electrode" or "electrode" of the present inventions. In other words, a current is measured at a chosen applied voltage of a sensing electrode with respect to a reference electrode for obtaining analytical information from the current-concentration relationship at that applied voltage potential. In one example, the current obtained or measured depends on the concentration of an analyte, for example, phenol, such that the analyte would cause an oxidation/reduction of an electro-active species at the surface of a sensing electrode, for example, a current is generated by a redox reaction on the surface of a tyrosinase electrode in proportion to the concentration of phenol produced by the tyrosinase enzyme.

As used herein, "amperometric detection" in reference to a method refers to applying a potential (as compared to a separate reference electrode) between the electrode containing the compositions of the present invention and an auxiliary (counter) electrode in the test sample.

As used herein, "analytical information" refers to measurements obtained from a current-concentration relationship at a specified applied voltage potential.

As used herein, the term "oxidation-reduction" or "oxidation/reduction" or "redox" or "re-dox" in reference to a reaction involving the transfer of electrons between molecules, such that molecules may gain or loose electrons and be referred to as "electroactive species."

As used herein, the term "oxidation" refers to the loss of electrons. Conversely, "reduction" refers to the gain of electrons.

As used herein, the term "oxidizing agent" or "oxidant" refers to a substance that is affecting oxidation by accepting electrons from another substance.

As used herein, the term "reducing agent" or reductant" refers to a substance that is affecting reduction by donating electrons to another substance.

As used herein, the term "cathode" in reference to an electrode refers to an electrode receiving electrons or an electrode comprising a substance for receiving electrons.

As used herein, the term "anode" in reference to an electrode refers to an electrode loosing electrons or an electrode comprising a substance for loosing electrons.

As used herein, "electrolyte" refers to a liquid or any form of moisture that provides a path for ion flow, such as a solution that is capable of conducting an electric current, for example, a phosphate buffer solution.

As used herein, the term "polysalt" refers to a polymer whose repeating unit bears an electrolyte group, for example, a polyacid, a polybase, a polysalt, a polyampholyte, a polylysine, a polyacrylic acid, and the like.

As used herein, the term "polyelectrolyte" refers to a polymer whose repeating unit bears an electrolyte group, for example, As used herein, "electrode" refers to a composition that when connected to an electronic device, is able to sense a current or charge and convert it to a signal. Preferred electrode compositions are known in the art and include, but are not limited to electrodes comprising certain metals and their oxides, including gold; copper; silver; lead; zinc; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$), ruthenium oxides; carbon (including glassy carbon electrodes, graphite and carbon paste) and a nonmetal substance, such as a composite material, for example, a carbon composite, et cetera. For the purposes of the present inventions, the term "working electrode" refers to an electrode that serves as a transducer responding to an excitation signal, such as an electrode of the present inventions. For the purposes of the present inventions, the term "reference electrode" refers to an electrode used to measure the relative potential of a different electrode, such as a "silver/silver chloride" or "Ag/AgCl" reference electrode. In some embodiments, a working electrode comprises a reference electrode, for example, a combination electrode.

As used herein, "counter electrode" or "auxiliary electrode" refers to an electrode used to make a connection to the electrolyte so that a current can be applied to the working electrode. The counter electrode is usually made of an inert material, such as a noble metal, for example, a metal or alloy, such as gold or graphite.

As used herein, "Clark oxygen electrode" or "Clark-type oxygen electrode" or "Clark electrode" refers to an amperometric electrode that generates a current based upon the amount of oxygen that diffuses into the electrode. For example, a two-electrode electrochemical cell with the working electrode (typically positioned at the end of a tubular structure) separated from the test solution by a thin membrane permeable to oxygen. The oxygen diffusing through the membrane is reduced at the electrode surface with the current produced proportional to the concentration of the dissolved oxygen in the test solution.

As used herein, "electrode potential" refers to a measured potential between an electrode and a reference electrode in contact with an electrolyte. As used herein, the phrase "insulation layer" is intended to encompass any non-conductive material.

As used herein, the term "ampere" or "amp" or "A" refers to a measure of electric current: 1 A=1 coulomb/second.

As used herein, the term "Coulomb" or "C" refers to a measure of electrical charge, for example, 1 C is an amount of charge equal to that of about $6.24\times10^{18}$ electrons.

As used herein, the term "current" refers to a unit of measure as a function of a voltage potential applied to an electrode, for example, a certain imposed voltage of the sensing electrode with respect to the reference electrode. Current also refers to a unit of measure as a function of time at an applied voltage potential, for example, a one-ampere current is a flow of 1 C of charge per second.

As used herein, "voltage" or "volt" or "V" refers to the difference of electrical potential between two points of an electrical or electronic circuit, measured as a unit of electrical potential difference or volt.

As used herein, "voltammetry" refers to an electrochemical measuring technique used for electrochemical analysis or for the determination of the kinetics and mechanism of electrode reactions. "Voltammetry" also refers to family of techniques with a common characteristic where a potential of the working electrode is controlled (for example, with a potentiostat) and the current flowing through the electrode is measured, for example, potential step voltammetry, linear sweep voltammetry, cyclic voltammetry, AC voltammetry, and the like.

As used herein, "ellipsometry" refers to a technique involving an ellipsometer measuring device, for example, a technique used to measure the optical constants and thickness of organic layers on a surface as shown herein.

As used herein, "ellipsometer" refers to a device for measuring changes in the polarization state of light when it is reflected from a sample.

As used herein, "potential step voltammetry" refers to a measurement technique involving an applied voltage that is instantaneously jumped from one value (V1) to another value (V2).

As used herein, "resistance" or "Ohm" or "Ω-ohm" refers to a unit of resistance, such that one ohm is the electrical resistance between two points of a conductor, for example, when a constant potential difference of 1 volt is applied to each of the two points it produces a current of 1 ampere in the conductor.

As used herein, "nanostructured" refers to a device having at least one surface or coating of which the physical and chemical properties or features are in the nanometer range or smaller (for example, $<10^{-9}$ meters).

As used herein, "response time" refers to a time it takes for the sensor's output to reach its final value. A measure of how quickly the sensor will respond to changes in the environment. In general, this parameter is a measure of the speed of the sensor and must be compared with the speed of the process.

As used herein, "sensitivity" refers to an amount of change in a sensor's output in response to a change at a sensor's input over the sensor's entire range. Provides an indication of a sensor's ability to detect changes. For some sensors, the sensitivity is defined as the input parameter change required to produce a standardized output change.

As used herein, “signal-to-noise-ratio” refers to a ratio of the output signal with an input signal to the output signal with no input signal.

As used herein, “sample” or “test sample” is used in its broadest sense. On the one hand, a sample is meant to include a liquid or solid or gas. On the other hand, a sample is meant to include both biological and environmental samples. A biological sample may be obtained from an animal, including human, fluid or tissue, food products and ingredients such as dairy items, vegetables, meat and meat by-products, and waste, further including but not limited to, body fluids such as blood, tissue, cells, cerebrospinal fluid (CSF), as well as proteins and nucleic acid sequences. An environmental sample includes any environmental material such as surface matter, soil, water, and industrial samples, as well as samples obtained from food and dairy processing instruments, apparatus, equipment, disposable, and non-disposable items. These examples are not to be construed as limiting the sample types applicable to the present invention.

Whether biological or environmental, a sample suspected of containing an esterase or esterase inhibitor or esterase activator, the sample may first be subjected to an enrichment means to create a concentrated sample. For example, “enrichment means” or “enrichment treatment,” in reference to an esterase, the present invention contemplates (i) conventional techniques for isolating a particular protein or nucleic acid sequence of interest away from other proteins or chemicals, and (ii) novel techniques for isolating a particular protein or nucleic acid sequence away from other proteins or nucleic acid sequences. It is not intended that the present invention be limited only to one enrichment step or type of enrichment means. For example, it is within the scope of the present invention, following subjecting a sample to a conventional enrichment means, to subject the resultant preparation to further purification such that a purified protein of interest is produced. This purified protein may then be analyzed by compositions and methods of the present inventions.

DETAILED DESCRIPTION OF THE INVENTION

The present invention provides compositions, devices and methods for detecting esterase activity. The present invention also provides devices and methods of detecting esterase inhibitors, for example, organophosphates. In particular, the present invention provides a biosensor comprising Neuropathy Target Esterase (NTE) polypeptides. Further, the present invention relates to medicine, industrial chemistry, agriculture, and homeland security.

Neuropathy Target Esterase (NTE) is an enzyme found in vivo as a membrane bound esterase. Alterations in NTE activity are associated with or implicated with motor neuron disease, for example, described below. Recently, mutations in NTE were linked with debilitating neurological diseases such as Lou Gehrig’s disease. Rainier et al, “Neuropathy target esterase gene mutations cause motor neuron disease,” was presented at the 2005 American Society of Human Genetics meeting, Oct. 25-29, 2005 in Salt Lake City, Utah; and Rainier et al, (2008) Am J Hum Genet, 82:1-6; all of which are herein incorporated by reference.

Neuropathy Target Esterase activity can also be altered by exposure to organophosphorus (OP) compounds. Binding of certain OP compounds to NTE is believed to cause (OP)-induced delayed neuropathy (OPIDN), a type of paralysis for which there is no effective treatment. Symptoms of OIPDN include paralysis of the lower limbs beginning one to three weeks after exposure to a neuropathic OP compound. Recovery from this disease is usually poor and there is no specific treatment. However, the capacity of OPs to inhibit NTE and cause OPIDP does not necessarily correlate with their capacity to inhibit acetylcholinesterase (Definition of Organophosphate (OPs) and Their Toxicology, Welcome to the Pesticides Safety Directorate (PSD) website, 2006, on the world wide web at pesticides.gov.uk/approvals.asp?id=507).

Acetylcholinesterase is naturally found in vivo in nerve tissue, red blood cells, and brain, while pseudocholinesterase is naturally found in vivo in plasma, liver and brain. In humans, anticholinesterase OPs have broadly similar actions to those seen in other species, as described in “Definition of Organophosphate (OPs) and Their Toxicology,” 2006, Pesticides Safety Directorate (PSD), on the world wide web at pesticides.gov.uk/home.asp; herein incorporated by reference. For example, acetylcholinesterase inhibition causes acute effects in humans and other mammals. Symptoms in humans which generally occur when acetylcholinesterase activity has been reduced by about 50%, may include: headache, exhaustion and mental confusion together with blurred vision, sweating, salivation, chest tightness, muscle twitching and abdominal cramps. The severity of effects depends on the degree of acetylcholinesterase inhibition. Severe effects include muscle paralysis leading to severe difficulty in breathing thus requiring respiratory support of the patient, convulsions and unconsciousness. Recovery depends on elimination of the OP product from the body and return of acetylcholinesterase activity.

On the other hand, anticholinesterase exposure is not always harmful. Indeed, anticholinesterases are used for beneficial purposes in anesthesia and in the treatment of human diseases such as myasthenia gravis, glaucoma and Alzheimer’s disease.

Thus compositions and methods for measuring NTE and NEST activity, in addition to other cholinesterases, are needed for disease research and for detecting NTE inhibitors. Further, these compositions and methods are also needed or determining the presence and effects of chemical and biowarfare agents that target NTE.

The inventors provide as described herein, a nanostructured biosensor comprising esterase activity of NTE. An exemplary biosensor demonstrated a response time on the order of seconds and showed a dose-dependent decrease in sensor output in response to increasing concentrations of known NTE inhibitors. Potential applications of the biosensor include studying the fundamental reaction kinetics of NTE, screening OP compounds for effects on NTE activity, screening test samples for effects on NTE activity, screening environmental samples for effects on NTE activity, and investigating the effect of NTE mutations on NTE esterase activity.

A general description of electrodes and biosensors for measuring esterase activity are provided below for comparing to the compositions and methods of the present inventions. In order to overcome previous limitations of devices and methods for measuring NTE activity, the present invention provides devices and methods for rapid and sensitive measurements of the esterase activity of NTE or fragments of NTE that contain its esterase domain (e.g., NEST). Further, the devices and methods of the present invention overcome previous limitations by providing rapid and sensitive measurements of the reduction of the esterase activity caused by inhibitory compounds of esterase activity.

Tyrosinase is a copper-containing oxidase (Coche-Guerente, et al. (2001) Analytical Chemistry, 73:3206-3218; Forzani, et al. (2000) Analytical Chemistry, 72:5300-5307; all of which are herein incorporated by reference), which possesses two different activities, as illustrated in reaction (1).

$$\text{phenol} \longrightarrow \text{catechol} \longrightarrow \text{o-quinone} + H_2O \quad (1)$$

The first step is referred to as the enzyme's hydroxylase activity (also known as cresolase activity) where phenol is hydroxylated by the aid of molecular oxygen to produce catechol. In the second step, known as the catecholase activity, the enzyme oxidizes catechol to o-quinone and is simultaneously oxidized by oxygen to its original form, with the production of water. The reaction product, o-quinone, is electrochemically active and can be reduced back to the catechol form at low applied potentials, as illustrated in reaction (2).

$$o\text{-quinone}+2H^{+}+2e^{-}\rightarrow\text{catechol} \quad (2)$$

These characteristics of tyrosinase were exploited by us to fabricate a NEST biosensor, capable of measuring the NEST's esterase activity and its inhibition, by co-immobilizing NEST and tyrosinase on a gold electrode using layer-by-layer assembly approach.

I. Human NTE and NEST.

The term "Neuropathy target esterase" or "NTE" refers to a membrane-bound esterase found in neurons of vertebrates (Glynn (1999) Biochemical Journal, 344:625-631; L1, et al., (2003) Journal of Biological Chemistry, 278:8820-8825; Atkins, et al., (2000) The Journal of Biological Chemistry, 275:24477-24483; Kropp, et al., (2004) Biochemistry, 43:3716-3722; Makhaeva, et al., (2003) Journal of Toxicology and Environmental Health-Part A, 66:599-610; and van Tienhoven, et al., (2002) Journal of Biological Chemistry, 277:20942-20948; all of which are herein incorporated by reference). NTE was shown to be necessary for embryonic development in mice and believed to be involved in cell-signaling pathways and lipid trafficking (Glynn (1999) Biochemical Journal, 344:625-631). Further, NTE has serine esterase activity and hydrolyzes ester, peptide, and amide bonds.

Functionally, a nucleophilic serine residue (active site) of NTE attacks the carbonyl carbon atom of the substrate, forming a covalent acyl-enzyme intermediate that is subsequently hydrolyzed. One consequence of this reaction mechanism is that the esterase activity of NTE was susceptible to covalent inhibition by organophosphorus esters (OPs) that causes formation of an analogous phosphyl-enzyme intermediate. Irreversible binding of some OP compounds to the active serine site results in a debilitating neural disease known as (OP)-induced delayed neuropathy (OPIDN) (Glynn (1999) Biochemical Journal, 344:625-631). Symptoms of OIPDN include flaccid paralysis of the lower limbs that becomes evident two to three weeks after exposure to neuropathic OPs. Recovery from this disease is usually poor, and there is no specific treatment.

Expression of full-length human NTE is problematic. However a full-length human Neuropathy target esterase (NTE) and mutants thereof, were expressed in COS cells (European Collection of Cell Cultures, ECACC number 87021302; African green monkey kidney cells) (Li, et al., (2003) J. Biol. Chem. 278 (10):8820-8825; herein incorporated by reference).

Thus because NTE is difficult to produce for research purposes, research to study its esterase activity is typically done using a fragment of the NTE protein that contains the esterase activity domain polypeptide that is more easily produced than a full-length NTE. One such esterase activity domain polypeptide fragment is known as NEST (Atkins, et al. (2000), Journal of Biological Chemistry, 275:24477-24483; Kropp, et al. (2004) J. Biochemistry, 43:3716-3722; Forshaw, et al. (2001) Journal of Neurochemistry, 79:400-406; all of which are herein incorporated by reference) reacts with esters and inhibitors in a manner very similar to NTE.

Widespread and long-term use of OP compounds in industry and agriculture has resulted in a global distribution of these hazardous compounds throughout our environment posing a current health risk to humans and animals. Further, additional NTE poisons are present in our environment including neuropathic compounds from abandoned stockpiles, previous use of these compounds as chemical weapons, potential development and use as chemical weapons that pose additional health risks to animals and humans. Thus, in addition to its role in chemically induced sickness and death, NTE was also implicated in causing well-known motor-neuron diseases that don't require exposure to OP compounds. Recently, it was reported that gene mutations in NTE may lead to neurological disorders, for example, a mutation in an NTE gene linked to a disease phenotype was shown for amyotrophic lateral sclerosis (ALS), also known as Lou Gehrig's disease (Richardson, "Neuropathy target esterase gene mutations cause Motor neuron disease," presented at the 2005 American Society of Human Genetics meeting, Oct. 25-29, 2005, in Salt Lake City, Utah).

Specifically, the present invention provides screening methods for identifying modulators, i.e., candidate or test compounds or agents (e.g., chemicals, proteins, peptides, peptidomimetics, peptoids, small molecules or other drugs) which bind to a NTE of the present invention, that have an inhibitory (or stimulatory) effect on, for example, NTE activity. Compounds thus identified can be used to modulate the activity of target gene products (e.g., NTE proteins) either directly or indirectly in a therapeutic protocol, to elaborate the biological function of the target gene product, or to identify compounds that disrupt normal target protein interactions. Compounds, that would stimulate the activity of a variant NTE or mimic the activity of a non-functional variant are contemplated as being particularly useful in the treatment of neurological disorders (e.g., Hereditary spastic paraplegia (HSP) also called familial spastic paraparesis (FSP). In one embodiment, the invention provides assays for screening candidate or test compounds that are substrates of a NTE protein or NEST polypeptide or a biologically active portion thereof, or any esterase molecule of the present inventions. In another embodiment, the invention provides assays for screening candidate or test compounds that bind to or modulate the activity of a NTE protein or polypeptide or a biologically active portion thereof, or any esterase molecule of the present inventions.

Esterases and test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., (1994) J. Med. Chem. 37: 2678-85; herein incorporated by reference); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145; herein incorporated by reference).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994]; all of which are herein incorporated by reference.

II. Tyrosinase Electrodes for Measuring Esterase Activity.

There are numerous published descriptions of electrodes comprising tyrosinase. The following examples of these types of publications are not meant to be an exhaustive listing but provided merely as examples of tyrosinase based electrodes and esterase measuring devices. For example, a bi-enzyme tyrosinase electrode for measuring esterase catalytic activity was disclosed, see, for example, Sapelnikova, et al., (2003) Anal Bioanal Chem. 376 (7):1098-1103; herein incorporated by reference, as constructed using screen-printed electrode fabrication for combining several enzyme electrodes, such as bi-enzyme electrodes of tyrosinase and horseradish peroxidase (HRP) or cholinesterase-modified electrodes. These electrodes were disclosed as elements of amperometric devices combined on the same array for use in liquid batch mode and in a flow-injection system in further combination with hydrogen peroxide (co-substrate for the HRP-modified electrode) and acetylthiocholine chloride (co-substrate for cholinesterase).

A two-enzyme nanobiosensor/electrode was disclosed in Intl. Patent Publication No. WO 2005/074467 and U.S. Patent Appln. No. 20050244811; all of which are herein incorporated by reference, wherein the electrodes further comprised carbon nanotube paste, gold, conducting polymers, biological enzymes, such as tyrosinase, choline oxidase, nanoparticles and other nanoscale materials as sensor elements (working electrodes), a reference electrode (for example, a screen printed Ag/AgCl paste) and a counter electrode (gold) built in a three electrode electrochemical system. This sensor was disclosed for use in applications for metabolic monitoring potential chemical biological warfare agents (PCB's such as organophosphates, DMMP, malathion, ethion, parathion, paraozon and others), in both gases and liquid.

Biosensors were described using an enzyme, acetylcholinesterase or butyrylcholinesterase, fixed onto the surface of the transducer for detecting inhibition of acyl cholinesterases (acetylcholinesterase or butyrylcholinesterase) by organophosphorus compounds or on inhibition of enzymes phosphatases (acid or alkaline) or on direct detection of organophosphorus compounds by organophosphorus hydrolase (for example, Jaffrezic-Renault, (2001) Sensors 1:60-74; herein incorporated by reference). The fabrication and use of a biosensor/electrode for detecting a wide range of chemicals, such as organophosphate, wherein a set of enzymes or fusion proteins is immobilized (such as in a carbon-based matrix, a polymer based matrix, and the like) onto a substrate or surface of a chip or an isolated protein is added to a cross-linked gelatin, a conductive polymer, or a microcrystalline cellulose gel deposited on the surface of a platinum or palladium electrode, including a Clark electrode. For example, after purification of the biosensor polypeptides, such as an acetyl choline esterase, a polypeptide is added to a composite consisting of an immobilization matrix, buffer, necessary electrolytes, and a redox mediator such as an oxidoreductase enzyme EC 1.14.18.1 monophenol monooxygenase [tyrosinase] then the mixture can then be directly applied to an electrode surface and dried (for example, Intl. Patent Publication No. WO0210750; herein incorporated by reference).

A method for the preparation of fast response potentiometric acetylcholine (ACh) biosensors based on pH detection, using acetylcholinesterase (AChE) immobilized on the antimony disk electrode surface. The fast response of the ACh biosensor resulted in a considerable decrease of the real analysis time of the inhibitor, an organophosphorus type insecticide; trichlorfon. After each inhibition measurement cycle the biosensor was reactivated in pyridin-2-aldoxime methiodide for prolonged lifetime (for example, Gyurcsányi, et al., (1999) Electroanalysis, 11 (10-11):712-718 [abstract]); herein incorporated by reference.

A biosensor chip was described with a first electrode and a second, of which at least one electrode is made from gold or coated with a gold layer of nanometer thickness, of which at least one electrode comprises an immobilized ligand, such as an enzyme, for example, tyrosinase or alkaline phosphatase, and a probe molecule and/or a holding area for holding ligands, such as enzymes. Further, the first electrode and the second electrode being designed in such a manner that a reduction/oxidation recycling operation can take place at these electrodes generating a current of which an electric current can be detected and can be differentiated according to time (for example, U.S. Patent Appln. No. 20040014054; herein incorporated by reference).

During the development of the present inventions, other types of enzymes, specifically oxidases and the like, comprising enzymatic activity capable of use in a recycling mechanism of the present inventions were contemplated. In particular, oxidases such as horse radish peroxidase and laccase enzymes for use with a substrate, such as phenyl valerate and the like, were contemplated.

III. Measuring Neuropathy Target Esterase (NTE) and NEST Activity.

Neuropathy Target Esterase plays a central role in both chemically induced and spontaneously occurring neurological diseases. Therefore, methods for measuring NTE activity and inhibitor substances are of tremendous scientific and commercial importance. Previous methods for measuring NTE esterase activity involved two separate steps wherein the first step provides a test solution comprising an esterase, such as NTE, while the second step comprising a measuring device, such as a tyrosinase electrode, wherein the tyrosinase electrode does not comprise an esterase, such as NTE.

In the first step, at least two solutions are added together to form a test solution without an inhibitor solution or an additional test sample, wherein the first solution that contained a substrate, such as phenyl valerate, was brought into contact with a second solution comprising NEST or NTE protein. The NTE of the second solution may be a homogenate of tissue or purified NTE. For measuring esterase activity in a sample, a sample is added to the test solution, and further, when specific NTE inhibition was tested, an additional solution comprising an inhibitor was added to the test solution. Thus at least two solutions are added together for base-line sampling, wherein at least one solution comprises NTE for measuring NTE activity. Further, for environmental sampling, at least three solutions must be added together, wherein at least one solution comprises NTE. This method allowed the esterase enzyme in solution to react with the artificial substrate phenyl valerate to form phenol.

In the second step, the concentration of phenol in the mixed test solution was determined using a detection device, either colormetrically using a spectrometer or electrochemically using an electrode. Colormetric detection was done in the presence of 4-amino antipyrine (Makhaeva, et al., 2003, Journal of Toxicology and Environmental Health-Part A, 66:599-610); Kayyali, et al. (1991) Journal of Analytical Toxicology, 15:86-89; all of which are herein incorporated by reference), wherein the enzyme reaction was stopped, for example, by adding 2 mL of sodium dodecyl sulfate (1-2 percent W/V) in buffer containing 4-aminoantipyrine (otherwise known as 4-aminophenazone) (0.25 percent) followed by spectrometric absorbance measurements. Electrochemical measurements of activity were made in the presence of a tyrosinase enzyme (for example, Sigolaeva, et al. (2001) Analytical Biochemistry, 290:1-9; Sokolovskaya, et al. (2005) Biotechnology Letters, 27:1211-1218; all of which are herein incorporated by reference). When tyrosinase was used for electrochemical measurements, tyrosinase, attached to an electrode, wherein an esterase was not attached to the electrode, converted the phenol to catechol and then to an o-quinone that was measured electrochemically at the surface of an electrode (Makhaeva, et al. (2003) Journal of Toxicology and Environmental Health-Part A, 66:599-610; herein incorporated by reference). The current generated by the electrode was in proportion to the amount of o-quinone present, thus giving an indirect measurement of the amount of NTE esterase activity present in the mixed test solution. For example, the current increased as the amount of o-quinone increased. When esterase inhibition was tested, this procedure was repeated both in the absence and presence of a known or putative inhibitor (e.g. an OP compound). The reduced signal that followed the addition of a known esterase inhibitor confirmed inhibition of esterase activity. This method has the disadvantages of being relatively slow by requiring the preparation and mixing of numerous test solutions subsequently followed by an electrochemical measurement of esterase activity. Further, these methods require a large supply of NTE in order to provide test solutions comprising NTE. These limitations render this method unsuitable for important applications, such as high throughput screening of compounds for NTE inhibition and continuous on-line environmental monitoring of samples in order to detect chemical warfare agents that target NTE.

A. Examples of Electrodes for Measuring NTE Activity.

The following publications are provided merely as examples of electrodes capable of measuring NTE activity. A biosensor and methods to analyze Neuropathy target esterase (NTE) and its inhibitors were described in Sigolaeva, et al., (1999), Chemico-Biologycal Interactions, 119-120:559-65; herein incorporated by reference. This method is based on the combination of NTE enzymatic hydrolysis of phenyl valerate (PV) with phenol detection by the Clark-type oxygen electrode modified by immobilized tyrosinase, wherein the NTE providing hydrolysis activity was free in solution. In a different publication, a tyrosinase carbon-paste electrode for amperometric detection of neuropathy target esterase (NTE) activity was used for measuring NTE activity in solution by catalytic hydrolysis of a substrate, phenyl valerate, also in solution, where the electrode operated in a flow-injection mode that required 2 to 3 minutes per analysis (Makhaeva, et al., 2003, J Toxicol Environ Health A, 66 (7):599-610; herein incorporated by reference).

Methods are described for fabrication of a functional nanostructured biomimetic interface, comprising expressing recombinant cell membrane proteins, and further comprising embedding recombinant cell membrane proteins into biomimetic interfaces (Kohli, et al., Biomimetic Interfaces for Characterizing Membrane Proteins, November $4^{th}$, The 2005 American Institute of Chemical Engineers Annual Meeting (Cincinnati, Ohio) Cincinnati, Ohio, Biomaterials (08b) #594-Biomimetic Interfaces (08B03) abstract 594b; herein incorporated by reference). Further described were application of these interfaces to study medically relevant membrane proteins such as Neuropathy Target Esterase (NTE) for high-throughput drug screening systems and novel biosensors. Also described was the expression of recombinant membrane proteins that are embedded into biomimetic interfaces and fabrication of functional and nanostructured biomimetic interfaces to study the medically relevant membrane proteins such as Neuropathy Target Esterase (NTE) (Poster 35: Authors: Kohli, et al., Biomimetic Interfaces for Pharmaceutical Applications, 2006; herein incorporated by reference).

Finally, a combination electrode wherein an ultra-small tip, internal referenced, amperometric microbiosensor used an immobilized biological interface to measure the concentration of an analyte in a specimen, such as choline, for detecting exposure to organophosphorus pesticides and other compounds with similar toxicological behavior, with a response time of one minute was described (U.S. Pat. No. 5,611,900 to Worden et al.; herein incorporated by reference in its entirety).

B. NTE Biosensors of the Present Invention.

In the present invention, unlike the previous electrodes and sensors, a nanostructured biosensor interface is provided that comprises NTE enzymatic activity. However, production of full-length NTE protein for research purposes has been reported as being inefficient and uneconomical. Thus, the majority of published research on NTE activity involves using a fragment of the NTE protein that comprises NTE enzymatic activity that can be more efficiently produced. One such fragment, known as NEST, reacts with esters and inhibitors in a manner very similar to NTE. In some embodiments, the present invention provides a nanostructured biosensor comprising the NTE catalytic domain NEST.

In some embodiments, the biosensor is fabricated by co-immobilizing NEST protein and tyrosinase enzyme on an electrode using layer by layer assembly approach by Decher (Decher (1997) Science 5330:1232-1237; all of which are herein incorporated by reference). Surprisingly, this is the first time NEST has been immobilized in an active conformation on an electrode. The biosensor of the present invention is the first continuous, electrochemical biosensor for real-time, rapid measurement of NEST (or NTE) esterase activity. Thus, in one embodiment, the enzymatic activity of NTE is provided by a NEST protein attached to an amperometric electrode. In other embodiments, the enzymatic activity of NTE is provided by a NEST protein attached to a tyrosinase electrode.

In some embodiments, the present invention provides biosensors comprising full-length NTE. In some embodiments, the biosensors of the present invention are used for measuring NEST esterase activity using full-length NTE in place of NEST.

Thus, in some embodiments, biosensors comprising NTE are immersed in solutions comprising phenyl valerate for measuring enzymatic activity. In some embodiments, a self-contained NTE biosensor of the present invention is able to both rapidly measure NTE activity and simultaneously enable recording the loss of such activity in the presence of a known NTE inhibitor PMSF.

In some embodiments, the invention provides an exemplary biosensor formed by using a layer-by-layer assembly approach for immobilizing a layer of NEST protein molecules on top of previously applied layers of a polyelectrolyte, poly-L-lysine, and a tyrosinase protein enzyme. This biosensor demonstrated a response time on the order of seconds and showed a dose-dependent decrease in sensor output in response to known NTE or NEST inhibitors. Applications of the biosensor include, but are not limited to, studying the fundamental reaction kinetics of NTE mutants, screening OP compounds for NTE inhibition, and investigating the effect of NTE mutations on NTE esterase activity.

In some embodiments, biosensors of the present invention are assembled using a nanostructured tyrosinase electrode. In some embodiments, the biosensors of the present invention further incorporate electrochemical impedance spectroscopy (EIS), potential step voltammetry and ellipsometry for developing biosensors of the present inventions.

Applications of the biosensors of the present invention include, but are not limited to, detecting the presence of chemical weapons that target NTE, screening industrial and agricultural OP compounds for NTE inhibition, studying the fundamental reaction kinetics of NTE, and investigating the effect of NTE mutations found in ALS patients on NTE's enzymatic properties.

In some embodiments, the present invention provides methods comprising the following steps for measuring NTE activity using a biosensor of the present invention: (1) functional NTE reacts (hydrolyzes) phenyl valerate to form phenol, (2) the tyrosinase reacts with (oxidizes) phenol to from catechol and then tyrosinase further catalyzes the formation of o-quinone in a manner proportional to the amount of catechol, (3) the remaining elements of the electrode on which the interface is immobilized reacts (reduces) o-quinone back to catechol, wherein this last step is contemplated as the recycling and amplification step, and (4) an electrical current generated by the electrode in the presence of and proportional to the amount of o-quinone. It is further contemplated that the reductions in step (3) provides a continuous signal that increases in response to an increase in NTE esterase activity.

C. Esterase Biosensors of the Present Invention.

The methods of the present invention are also adaptable for providing additional types of esterase biosensors. Specifically, in some embodiments, the substrates and methods described herein are used to immobilize and measure the activity of other esterases such as acetylcholinesterase and butyrylcholinesterase. In some preferred embodiments, a phenyl valerate substrate provides the highest level of NEST and butyrylcholinesterase sensitivity for measuring esterase activity. In other embodiments, phenyl acetate showed the highest sensitivity in combination with acetylcholinesterase esterase activity.

The compositions and methods described herein for the NTE biosensor can also be extended to measure the activity of other medically relevant esterases such as acetylcholinesterase (AChE) and butyrylcholinesterase (BChE). AChE, also known as Red Blood Cell (RBC) cholinesterase or erythrocyte cholinesterase was found primarily in the blood and neural synapses (Davis, et al. (1997) Anaesthesia 52:244-260; Herz, et al. (1973) Pediatric Research 1973, 7:204-214; Hsieh, et al. (2001) J. Neurotoxicology 2001, 22:423-427; and Lejus, et al. (1998) Annales Francaises D Anesthesie Et De Reanimation, 17:1122-1135; all of which are herein incorporated by reference). BChE, also known as plasma cholinesterase or pseudocholinesterase, was found primarily in the liver (Lejus, et al. (1998) Annales Francaises D Anesthesie Et De Reanimation, 17:1122-1135; Darvesh, et al. (2003) Nature Reviews Neuroscience, 4:131-138; all of which are herein incorporated by reference). Both of these enzymes hydrolyze the neurotransmitter acetylcholine into choline and acetic acid, a reaction necessary to allow a cholinergic neuron to return to its resting state after activation, but they differ in their respective preferences for substrates. The former hydrolyzes acetylcholine more quickly and the latter hydrolyzes butyrylcholine more quickly. Cholinesterase inhibitors are potent neurotoxins or biological warfare agents against humans because exposure to them may cause any one of excessive salivation and eye watering in low doses, followed by muscle spasms and ultimately death. Commonly known acetylcholinesterase inhibitors include are snake venom and sarin.

Figure 13:
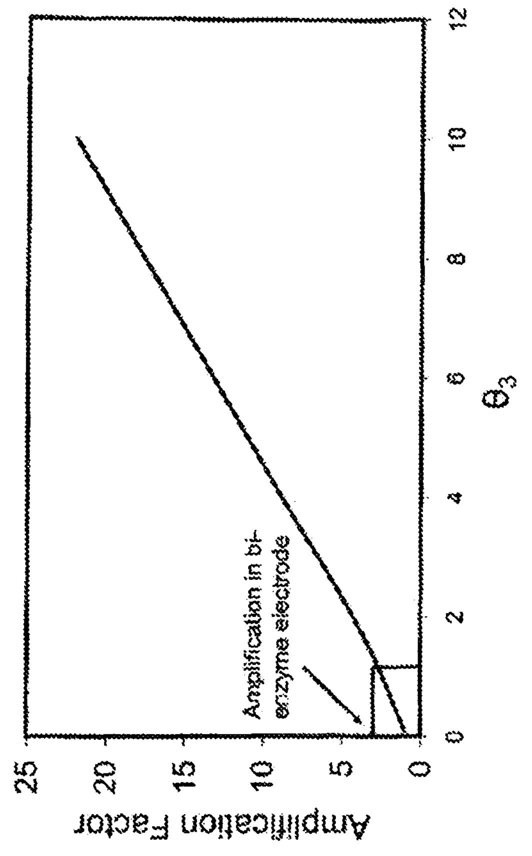
FIG. 13 shows exemplary differential equations relating to the present inventions.

D. Significance of NEST Biosensor:

The compositions and methods of the present inventions offer several advantages over previously known sensors and electrodes for measuring esterase activity. The first advantage of using electrodes of the present invention comprising NTE enzymes, is the reduction of the number of steps required for measuring NTE activity to one step, consisting of immersing the biosensor interface comprising an esterase into a test solution containing a substrate, such as phenyl valerate, rather than a two step method of adding a substance comprising esterase to a substrate in solution and then immersing a tyrosinase electrode into a solution of both esterase and substrate. Because the NTE esterase activity is co-immobilized with tyrosinase on the sensor interface rather than in solution where it is not attached to the tyrosinase electrode, the presence of phenyl valerate triggered a cascade of reactions that resulted in an electrical signal. Second, the electrodes comprise nanometer-scale thickness of enzyme layers on the sensing interface of the electrode, which provides for a very short diffusion path that provides a more rapid response time that in total was less than 10 seconds. Third, the biosensor is useful for continuous, real-time measurements of NTE esterase activity due to the rapid response time. Fourth, the biosensor is designed to achieve signal amplification, thus increasing the sensitivity of the sensor. The inventors contemplate that the signal amplification arose from a recycle mechanism that allowed catechol and o-quinone to accumulate at the biosensor interface. Because the biosensor's signal increased with increased o-quinone concentration, this recycling mechanism results in a higher signal for a given amount of NTE activity than achieved without recycling capabilities. Fifth, mathematical models have been developed for this biosensor that facilitate optimization of the biosensor's performance characteristics. Sixth, the biosensor' interface is generated by flexible, layer-by-layer, molecular self-assembly methods that allowed for adding improvements predicted by theoretical mathematical models (FIGS. 13-15) that were rapidly reduced to practice and verified in experimental systems such as those described herein. For example, the spatial orientations and proportions of the two enzymes could be readily controlled to optimize biosensor response. Seventh, the molecular self-assembly methods allow the biosensor interface to be assembled on electrodes inside microfluidic channels, thus enabling the production of high-density biosensor arrays for high-throughput applications.

Finally, the inventors contemplated further increasing the sensitivity of their electrode by increasing the flow of fluid comprising substrate over the electrode surface. Two methods of increasing fluid flow are 1) mounting the electrode on a rotating disk to rotate the electrode in the fluid in other words a "rotating disk electrode" wherein a "rotating disk electrode" also refers to an electrode capable of being mechanically rotated and 2) accelerating fluid flow over the electrode surface by using jets of fluid or other means of moving fluid. Thus in some embodiments, the inventors provided biosensors comprising rotating disk electrodes in place of nonrotating electrodes, also referred to as "stationary electrodes."

Thus, biosensors of the present invention provide devices with unique advantages over previously described sensors. In summary, compositions and methods for measuring of esterase activity utilize a solution comprising of an esterase substrate for triggering an electrical signal, esterase enzymes and thus their activity were co-immobilized with tyrosinase on the sensor interface rather than provided in solution. Further advantages are provided by biosensor interfaces comprising organic layers on the order of nanometer-scale thickness in the sensing interface thus providing a short diffusion path that allowed a rapid response time (less than 10 seconds) and continuous real-time measurements of esterase activity when contacted with an esterase substrate. Biosensors of the present invention further demonstrate signal amplification thus providing high sensitivity of esterase activity. Furthermore, because the biosensor interface is generated by flexible layer-by-layer molecular self-assembly methods the inventors contemplate assembling these electrodes inside microfluidic channels, thus enabling the production of high-density biosensor arrays consisting of various esterases for high-throughput applications.

These combinations of desirable properties makes this esterase interface well suited for important and necessary applications, including studying the kinetic properties of esterases such as NTE (or NEST) protein, high-throughput screening of NTE compounds (or NEST) for inhibition and continuous, on-line, environmental monitoring to detect chemical warfare agents that target NEST (or NTE) and other esterases.

IV. NTE and Susceptibility to Organophosphate Toxicity.

Individuals with altered NTE expression may have increased or decreased susceptibility to organophosphate toxicity. As an example, both chemically and genetically induced NTE deficiency, for example, a decrease in NTE, a decrease in NTE activity by inhibiting NTE with the compound ethyl octylphosphonofluoridate (EOPF), caused increased sensitivity to organophosphate toxicity and increased resulting neurotoxic symptoms such as motor activity (see, Winrow et al., (2003) 33 (4) Nature Genetics 477-485; herein incorporated by reference).

Therefore, the present invention provides methods for screening individuals for susceptibility to organophosphate toxicity. In some embodiments, the methods comprise screening an individual for increased susceptibility to organophosphate toxicity. In some embodiments, the methods comprise screening an individual subject for susceptibility to organophosphate toxicity comprising functional and genetic testing of the subject's NTE. In one embodiment, the methods comprise screening an individual subject for exposure to an organophosphate. In one embodiment, the methods comprise screening an individual subject for exposure to a neurotoxic compound. In preferred embodiments, the subject's NTE is tested functionally using devices and methods of the present inventions. In other embodiments, a subject's NTE is screened by a combination of functional and genetic testing of the individual's NTE.

The present invention further provides compositions and methods for studying kinetic properties of NTE activity, high-throughput screening of compounds for NTE inhibition, and continuous on-line environmental monitoring in order to detect chemical warfare agents that target NTE.

In some embodiments, the present invention provides biosensors for studying the kinetic properties of the NTE esterase activity, high-throughput screening of compounds for NTE inhibition, and continuous, on-line, environmental monitoring to detect chemical warfare agents that target NTE. In some embodiments, the biosensors are used for detection of NTE, inhibitors and neuropathic compounds that age NTE and thereby cause OPIDN, improving signal-to-noise ratio and sensitivity, demonstrating that the sensor works for full-length NTE, and assembling biosensor analysis for high-throughput measurements of multiple samples.

V. Methods of Identifying Individuals at Risk for Developing Motor Neuron Disorders.

NTE is an integral membrane protein present in the majority of neurons and in some non-neural-cell types of vertebrates, such as red blood cells. NTE is involved in a cell-signaling pathway controlling interactions between neurons and accessory glial cells in the developing nervous system. NTE has serine esterase activity in vivo and efficiently catalyses the hydrolysis of phenyl valerate (PV) in vitro. By sequence analysis NTE is related neither to the major serine esterase family, which included acetylcholinesterase, nor to any other known serine hydrolases. NTE comprises at least two functional domains: an N-terminal putative regulatory domain and a C-terminal effector domain which contains the esterase activity and is, in part, conserved in proteins found in bacteria, yeast, nematodes and insects. NTE's effector domain contains three predicted transmembrane segments, with the active-site serine residue at the center of one of these segments. The isolated recombinant domain shows PV hydrolase activity when incorporated into phospholipid liposomes.

In preferred embodiments, the present invention provides a method of diagnosing motor neuron disorders comprising a subject's NTE enzyme.

In other embodiments, the present invention provides a method genetic sequencing of a subject's NTE gene sequence. In other embodiments, the present invention provides a method of diagnosing motor neuron disorders through enzymatic testing of a subject's NTE enzyme. In other preferred embodiments, the risk of developing a motor neuron disorder may be ascertained through genetic testing of a subject's NTE gene sequence. In some embodiments, the risk of developing a motor neuron disorder may be ascertained through enzymatic testing of a subject's NTE enzyme.

There are numerous motor neuron disorders that may be linked to alterations in esterase activity. Thus, subjects with motor neuron disorders would benefit from methods comprising biosensors of the present inventions for measuring NTE esterase activity. For example, motor neuron disorders, such as delayed neuropathy, as found in patients with swelling of lower limbs or paralysis; motor neuron diseases, as found in patients with neurological disorders where motor neurons are destroyed as in amyotrophic lateral sclerosis or Lou Gehrig's disease, wherein muscle weakness is progressive and eventually fatal; are contemplated as subjects who would benefit and inhibition are of scientific importance. Subjects with motor neuron disorders such as those listed below, would benefit from methods comprising biosensors of the present inventions including but not limited to amyotrophic Lateral Sclerosis (ALS or Lou Gehrig's disease), autosomal recessive spastic paraplegia, hereditary spastic paraplegia, primary lateral sclerosis, progressive pseudobulbar palsy, progressive muscular atrophy, progressive bulbar palsy, and postpolio syndrome.

Symptoms characteristic for a specific type of motor neuron disorder vary according to the part of the nervous system most affected by the disease. Moreover motor neuron disorders typically involve progressive deterioration of the motor nerves in the spinal cord or brain, causing muscle weakness that can progress to paralysis. Clinical aspects of motor neuron disorders involve debilitating symptoms commonly resulting in death. Clinical features of these disorders that would signal diagnostic concerns include detecting onset by signs of progressive motor neuron involvement. However, nerve conduction velocities for many of these disorders appear normal until later in the progression of disease. Electromyography is the most useful test, showing fibrillations, positive waves, fasciculations, and giant motor units, even in unaffected limbs, however such tests are not useful for predicting genetic or somatic susceptibility. Thus methods of identifying individuals at risk for developing motor neuron disorders, especially prior to onset of disease symptoms, are needed and my be met by compositions and methods comprising biosensors of the present inventions described herein.

In summary, biosensors were developed for continuous measurements of NEST activity. The biosensors were fabricated by layer-by-layer assembly approach to co-immobilize NEST and tyrosinase on a gold electrode for providing real-time measurements of esterase activity. Ellipsometry and EIS provided evidence for the sequential assembly of the multiple layers that make up the interface. Constant potential voltammetry allowed NEST enzyme activity to be measured with a rapid response time (<10 s). The biosensor gave dose-dependent response to known non-neuropathic (PMSF) and neuropathic (Mipafox) NEST inhibitors. The same interface can also be used to immobilize and measure the activity of other medically relevant esterases such as acetylcholinesterase and butyrylcholinesterase.

Further, a theoretical method for bi-enzyme electrodes, capable of rotation, with substrate recycling was developed for use in designing electrodes with increased sensitivity for a set concentration of esterase, in particular a NTE. The method was validated by studying the response of bi-enzyme rotating disk electrode consisting of two enzymes, NEST and tyrosinase, to phenyl valerate, phenol and catechol under varying rotating speeds. The validated model assisted in determining and quantifying the influence of important parameters such as mass transport in the bulk and enzyme layer, partition coefficients, enzyme kinetics and catechol recycling on the sensitivity of the sensor. This information is contemplated for use in optimizing the metrological characteristics of bi-enzyme electrodes. As a result of using this method for achieving even higher signal amplification, the inventors contemplate further methods for increasing a oxidase (for example, tyrosinase, laccase, horse radish peroxidase an the like, for loading tyrosinase loading on the electrode surface interface. Also contemplated is using these types of interfaces as a sensor for detecting NEST inhibitors such as organophosphorous compounds.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); mm (millimeters); nm (nanometers); μ (micrometer); U (units); V (volts); sec (seconds); min(s) (minute/minutes); hr(s) (hour/hours); PCR (polymerase chain reaction); RT-PCR (reverse transcription PCR); hertz (Hz); W (watts). In addition, Thioctic acid, poly-L-lysine (PLL) (molecular weight approximately 15,000), tyrosinase (Tyr), sodium phosphate (monobasic and dibasic), ethylenediaminetetraacetic acid (EDTA), sodium chloride, 3-[(3-cholamidopropyl)dimethylammonio]-1-propanesulfonate (CHAPS) and isopropyl thiogalactoside (IPTG), acetylcholinesterase, and butyrylcholinesterase were obtained from Sigma (St. Louis, Mo.), ultrapure water (18.2 M·Ω) was supplied by a Nanopure-UV four-stage purifier (Barnstead International, Dubuque, Iowa) where the purifier was equipped with a UV source and a final 0.2 μm filter.

The proteins used in these EXAMPLES were produced in Michigan State University's (MSU) Protein Expression Lab. The biosensor's interface as described herein, was developed at MSU's Center for Nanostructured & Biomimetic Interfaces (CNBI).

In the following examples, the inventors describe the construction and use of a functional biosensor that detected NTE esterase activity and detected inhibition of esterase activity by a compound known to inhibit NTE (e.g., PMSF) (see, Kohli, et al., 2007, Anal. Chem. 79, 5196-5203 and Kohli, et al., 2006, AIChE Annual Meeting, Nov. 12-17, 2006, San Francisco Hilton, San Francisco, Calif.; all of which are herein incorporated by reference in their entirety.

Example I

This example provides general Materials and Methods used for construction of and testing both types of electrodes stationary (nonrotating) and electrodes capable of being rotated for providing a biosensor of the present inventions, unless otherwise noted.

Materials:

thioctic acid, poly-L-lysine (PLL) (molecular weight approximately 15,000), tyrosinase (Tyr), sodium phosphate (monobasic and dibasic), ethylenediaminetetraacetic acid (EDTA), sodium chloride, 3-[(3-cholamidopropyl)dimethylammonio]-1-propanesulfonate (CHAPS) and isopropyl thiogalactoside (IPTG), acetylcholinesterase, and butyrylcholinesterase were obtained from Sigma (St. Louis, Mo.). Ultrapure water (18.2 M·Ω) was supplied by a Nanopure-UV four-stage purifier (Barnstead International, Dubuque, Iowa); the purifier was equipped with a UV source and a final 0.2 μm filter. Mipafox was supplied by *Oryza* Labs.

Vectors:

The *E. coli* BL21(DE3) pLysS strain and pET21b vector were purchased from Novagen. Nickel-nitrilotriacetic acid-agarose was purchased from QIAGEN Inc. Polymerase chain reactions were carried out using Pfu polymerase and the NTE cDNA clone D16 as a template (see, Atkins, et al. (2000), Journal of Biological Chemistry, 275:24477-24483; herein incorporated by reference). Polymerase chain reaction products corresponding to amino acids 727-1216 and 733-1216 were subcloned into the pET21b vector where DNA sequences were verified to be present using DNA sequencing methods well known in the art.

Figure 2B:
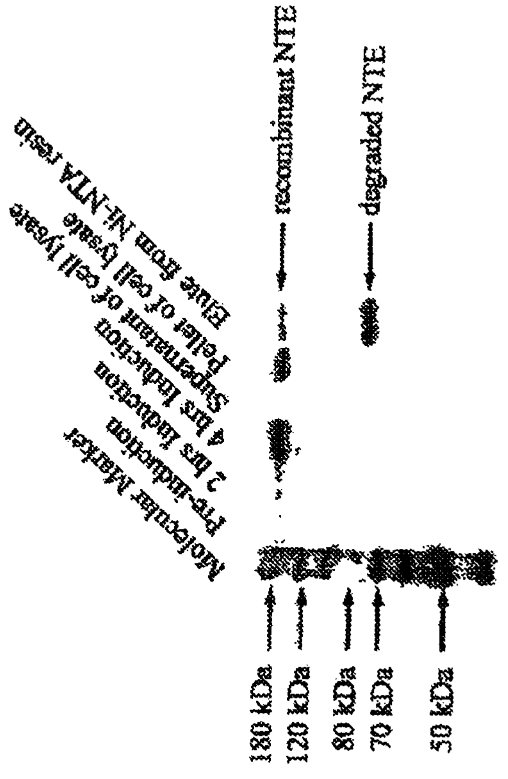

NEST Expression and Purification:

NEST was expressed in and purified from *E. coli* according to published procedures, briefly described herein (Atkins, et al. (2000), Journal of Biological Chemistry, 275:24477-24483; herein incorporated by reference). Briefly, a DNA fragment encoding NEST (for example, SEQ ID NO: 1, see, for example, FIG. 2A.) was cloned into a pET-21b vector and the resulting expression vector was transformed into *E. coli* BL21(DE3). An overnight culture of transformed *E. coli* was inoculated with M9 media containing ampicillin and grown in a fermentor device. IPTG was added to the resulting cell culture after a day to induce the expression of NEST. The resulting cells were collected 4 h after induction by centrifugation and subjected to protein expression techniques. Briefly, 5 g of cell paste was suspended in 30 ml of PEN buffer (50 mM sodium phosphate/0.3 M NaCl/0.5 mM EDTA, pH 7.8) containing 2% CHAPS and tip sonicated four times. The cell lysate was centrifuged at 12000 rpm for 30 min at 4° C., the supernatant was collected, and about 7 mL of supernatant was added to a mini column (volume 10 mL) containing 3 mL of Ni-NTA resin. The mini-column was rotated at room temperature for 20 min, centrifuged at 2000 rpm for 20 sec and then the top solution was drawn off. The histidine tagged NEST was eluted from the Ni-NTA resin using 10 mL of PEN buffer (50 mM sodium phosphate, pH 7.8, 300 mM NaCl, and 0.5 mM EDTA) containing 0.3% CHAPS and 0.3 M imidazole. Protein purity was determined using SDS PAGE (FIG. 2B) and protein concentration was determined using BioRad DC protein assay kit. For long-term storage, 25% glycerol was added to the protein solution, which was then stored at −20° C. Detergent was used both for solubilization of NEST from lysates of *E. coli* and during purification procedures. If catalytic activity of purified NEST was lost in detergent extracts, it was restored when purified NEST was incorporated into dioleoylphosphatidylcholine liposomes.

Preparation of Phenyl Valerate Solution:

15 mg of phenyl valerate was dissolved in 1 mL of dimethylformamide (DMF), and 15 mL of water containing 0.03% Triton was added slowly under vigorous stirring. For potential step voltammetry experiments, small aliquots of the resulting phenyl valerate micellar solution (5.286 mM) were added to a phosphate buffer to obtain the desired concentrations.

Preparation of Piranha Solution:

Piranha cleaning solution, also referred to as piranha etch, was a hot mixture of sulphuric acid ($H_2SO_4$) and hydrogen peroxide ($H_2O_2$), used to clean organic residue off of substrates such as the base electrodes of the present inventions prior to the layering of the biosensor components. Piranha solution is a 3:1 concentrated sulphuric acid to hydrogen peroxide solution (such as a 30% hydrogen peroxide stock solution). Alternatively, other concentrations of acids can be used, such as a 4:1 up to a 7:1 mixture of concentrated sulphuric acid to hydrogen peroxide solution, including a closely related mixture, referred to as "base piranha" that is a 3:1 mixture of ammonium hydroxide ($NH_4OH$) with hydrogen peroxide. A dipping bath was made with sulphuric acid, to which was added the peroxide solution. The electrodes were slowly immersed into the solution and cleaned from 10 to 40 minutes, after which time the electrode was removed from the solution and rinsed with a large amount of deionized water.

Poly-L-Lysine (PLL) Solution:

PLL solution was prepared by adding 12 mg of PLL to 50 mL of 20 mM phosphate buffer (pH 8.5).

Figure 4A:
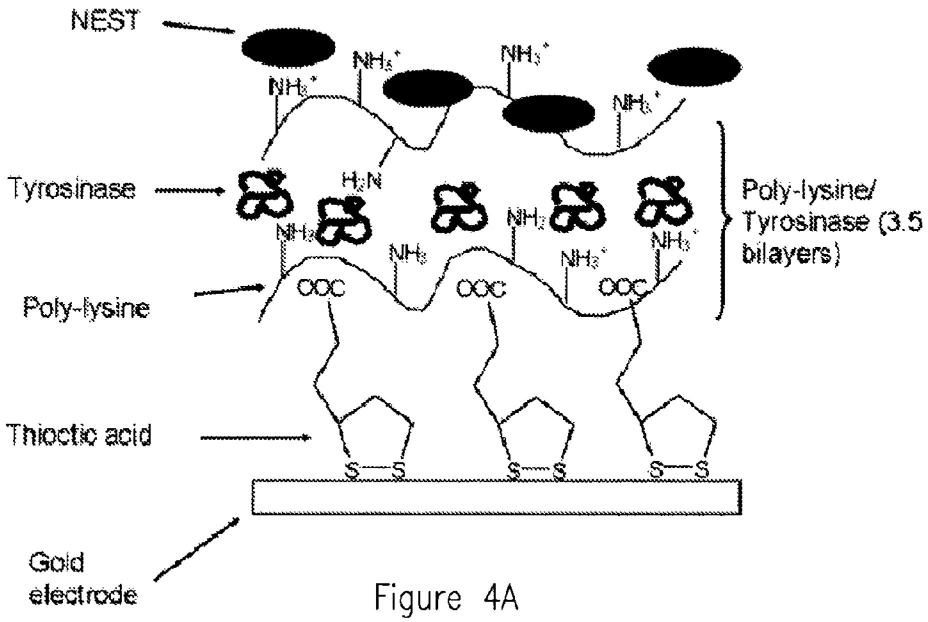
FIGS. 4A-4D show an exemplary molecular architecture of a bi-enzyme electrode provided using the layering methods described herein and shown in FIG. 3.

Preparation of Gold Electrode for Use as a NEST Biosensor:

The molecular architecture of a NEST biosensor interface is shown schematically in FIG. 4A and B. In order to assemble an exemplary NEST biosensor, gold electrodes were cleaned in Piranha solution, as described, supra, then electrodes were dipped in 5 mM solution of thioctic acid in ethanol for 30 minutes. The electrodes were washed with ethanol, dried under nitrogen and dipped in PLL solution for 45 minutes. The electrodes were then rinsed with water and dipped in an aqueous solution of Tyrosinase (0.2 mg/ml) for 1 hour. The last two steps were repeated 3.5 times to create 3.5 PLL-Tyr bilayers with PLL as the topmost layer. The electrodes were washed with water and dipped in a solution of NEST protein (0.1 mg/ml) in 100 mM phosphate buffer, pH (7.0) for 1 hour. The electrodes were then washed with water, dried under nitrogen and dipped in phosphate buffer (0.1 M, pH 7.0) for testing.

Preparation of Gold Electrode for Measuring the Activity of Acetylcholinesterase and Butyrylcholinesterase:

Acetylcholinesterase and butyrylcholinesterase were immobilized on separate tyrosinase electrodes by the same procedure used for assembling the NEST biosensor described herein, with the exception that the NEST solution was replaced by a solution of either acetylcholinesterase and butyrylcholinesterase, such that the final dipping was done in 0.1 mg/mL phosphate buffer solution (pH 7.0) of acetylcholinesterase or butyrylcholinesterase.

Figure 5:
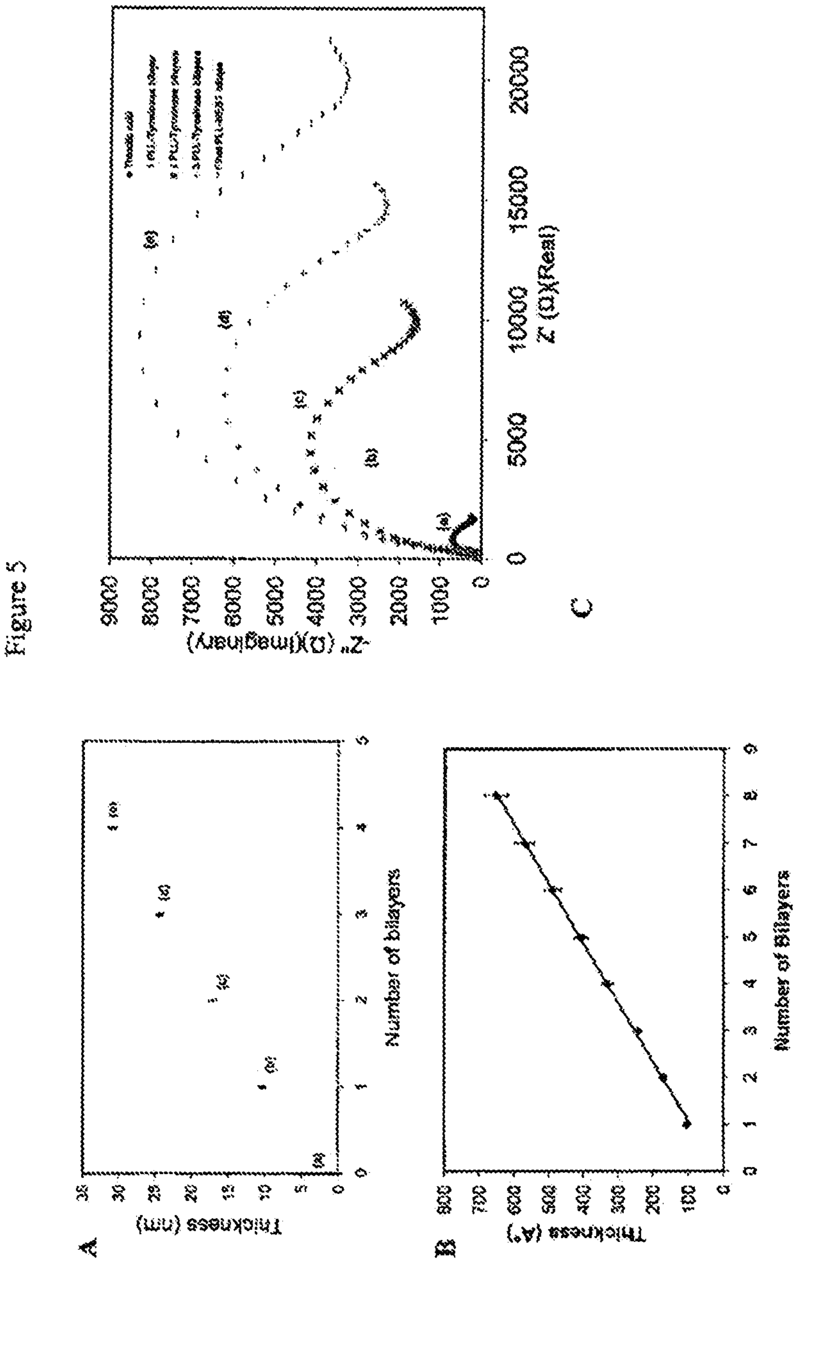
FIG. 5 shows exemplary ellipsometry measurements for determining the number of bilayers on the surface of a biosensor of the present inventions: specifically (A) shows exemplary ellipsometric thickness of deposited layers after the successive addition of the following layers: thioctic acid (point a), PLL (polycation)-Tyr first bilayer (point b), PLL-Tyr second bilayer (point c), PLL-Tyr third bilayer (point d), and a PLL and NEST final bilayer (point e), (B) shows exemplary ellipsometric thickness of deposited layers and (C) shows an exemplary Faradaic impedance spectra obtained on a bare gold electrode following the successive addition of the following layers: thioctic acid (curve a), PLL-Tyr first bilayer (curve b), PLL-Tyr second bilayer (curve c), PLLTyr third bilayer (curve d), and PLL and NEST final bilayer (curve e). Impedance measurements were made in 0.1 M phosphate buffer, pH 7.0, in the presence of 1:1 10 mM $[Fe(CN_6)]^{3-/4-}$. Geometric area of the electrode=0.16 $cm^2$.

Electrochemical Impedance Spectroscopy (EIS):

Electrochemical impedance spectroscopy results were obtained using a CHI 660B electrochemical analyzer (CH instruments, Austin, Tex.) for obtaining measurements of the thickness of each layer formed after dipping the gold working electrode in [Fe(CN)6]3−/4− (1:1), 1 mM, in phosphate buffer, pH 7.0. The impedance spectrum was obtained by sweeping an applied potential of 10 mV from 0.1 Hz to 104 Hz, superimposed on a DC offset equivalent to open circuit potential. The impedance spectra were fitted using Z-view software (Version 2.1b, Scribner Associates, Southern Pines, N.C.). See, FIG. 5.

Ellipsometry:

Ellipsometric measurements were obtained with rotating analyzer ellipsometer (model M-44; J.A. Woollan Co. Inc., Lincoln, Nebr.) using WVASE32 software. The thickness values for dried films were determined using 44 wavelengths between 414.0 nm and 736.1 nanometers. The angle of incidence was 75° for all experiments. Refractive indices of films containing PLL and proteins was estimated to be constant values of n=1.5 and k=0. These optical constants compared well with those values determined by ellipsometry for actual 4 bilayer films of poly-L-lysine and tyrosinase without an esterase. See, FIG. 5.

Potential Step Voltammetry and Other Measurements:

The electrodes (sensors) were maintained at a potential of −100 mV (vs. Ag/AgCl reference electrode) using a BAS CV-50W electrochemical analyzer. The esterase activity of NEST biosensor was monitored by measuring the output current for a variety of phenyl valerate concentrations, under conditions of stirred solutions. The NEST protein converts phenyl valerate to phenol, which gets converted to o-quinone by tyrosinase. The o-quinone gets reduced at the electrode's surface, resulting in the generation of current. The electroreduction of o-quinone produces catechol that again gets converted to o-quinone by tyrosinase, thus amplifying the signal. See, FIG. 5.

Esterase activity was measured using a known quantity of phenyl valerate added to the phosphate buffer (pH 7.0), under stirred conditions. After the stabilization of current, a known amount of NEST inhibitor was added, and the resulting decrease in current was measured.

Example II

Expression of Full-Length NTE and NEST.

Moreover, based on the preliminary date described below, the inventor's believe this is the first demonstration of heterologous expression of a full-length, fully active NTE protein. In order to obtain this full-length functional protein, cDNA for the full-length human NTE was subcloned into plasmid pTrcHis2/TOPO (Invitrogen) to yield plasmid pTrcHis2/hNTE, which was then transformed into an *E. coli* Rosetta (DE3) expression host. The cells were grown on LB medium in shake flask to an OD600 of 1.0, and NTE expression was induced with 0.5 mM IPTG. The resulting Western blot (FIG. 2B) shows a band consistent with full-length NTE expression.

Detergent-solubilized putative NTE was affinity-purified using Ni-NTA resin and checked for phenyl valerate esterase activity. A negative control was provided using the Ni-NTA resin eluent from the cell lysate of *E. coli* Rosetta (DE3) cell containing pTrisHis2/LacZ vector induced with 0.5 mM IPTG. The phenyl valerate esterase activity for the negative control was only 0.18% that for an NTE eluent. The expression of a recombinant protein having the correct molecular weight and phenyl valerate esterase activity provides strong evidence of active human NTE expression in *E. coli*. The inventors also report a scaled up expression of human NTE in a 10-L fermentor, using the protocol described herein for providing NEST proteins.

Moreover, based on the preliminary data described below, the inventor's believe that this is the first demonstration of expressing a heterologous full-length, active NTE protein. The cDNA for the full-length-human NTE was subcloned into plasmid pTrcHis2/TOPO (Invitrogen) to yield plasmid pTrcHis2/hNTE, which was transformed into *E. coli* Rosetta (DE3) expression host. The cells were grown on LB medium in shake flask to an OD600 of 1.0, and NTE expression was induced with 0.5 mM IPTG. The resulting Western blot (FIG. 2B) shows a band consistent with full-length NTE expression. Detergent-solubilized, putative NTE was affinity purified using Ni-NTA resin and checked for phenyl valerate esterase activity. The negative control was the Ni-NTA resin eluent from the cell lysate of *E. coli* Rosetta (DE3) cell containing pTrisHis2/LacZ vector induced with 0.5 mM IPTG. The phenyl valerate esterase activity for the negative control was 0.18% that for NTE eluent. The expression of a recombinant protein having the correct molecular weight and phenyl valerate esterase activity provides strong evidence of active human NTE expression in *E. coli*. The expression of this protein was scaled up for higher yields in a 10-L fermentor, using the protocol successfully used for the expression of NEST proteins.

Example III

Preparation of Gold Electrode for NEST Biosensor.

Figure 3A:
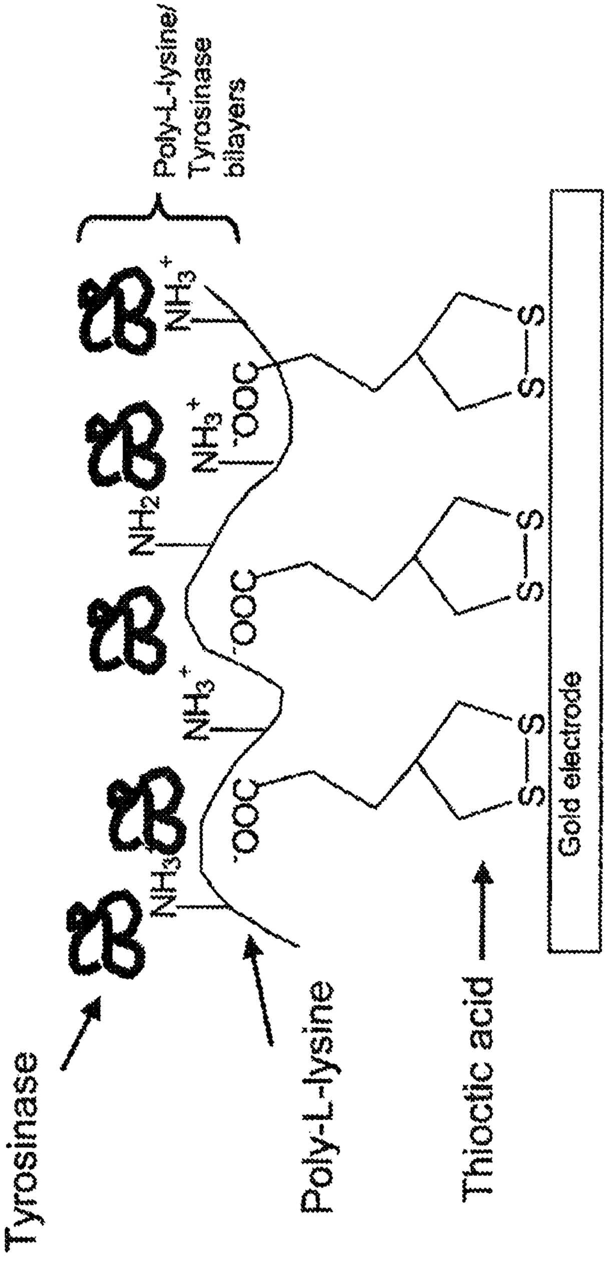

The inventors produced electrodes comprising human NTE and tyrosinase. The following procedure was used to make prototype biosensors of the present inventions that have the molecular architecture shown schematically in FIGS. 3A and 4B. For example, gold electrodes (3 cm×1 cm) were cleaned in Piranha solution, dried, and then dipped in 5 mM solution of thioctic acid for 30 minutes. The electrodes were then washed with ethanol, dried under nitrogen and dipped in PLL solution in 20 mM phosphate buffer (pH 8.75) for 45 minutes. The electrodes were then rinsed with water and dipped in an aqueous solution of tyrosinase (0.2 mg/ml) for 1 hour. The last two steps of soaking and rinsing in PLL and tyrosinase were repeated 3.5 times to create 3.5 PLL-Tyr bilayers with PLL as the topmost layer. These tyrosinase electrodes were then washed with water and dipped in a solution of NEST protein (0.1 mg/ml) in 100 mM phosphate buffer, pH (7.0) for 1 hour (a schematic of tyrosinase binding to a substrate is shown in FIG. 4A). The NEST electrodes (as shown schematically in FIG. 4B) were then washed with water, dried under nitrogen, and dipped in phosphate buffer (0.1 M, pH 7.0) for testing described herein. This electrode rapidly (within seconds) detected the presence of an NTE inhibitor added to the substrate solution. In one embodiment, organophosphates were detected via the interruption of electrical current generated by the general reactions described in brief below. Some advantages of using electrodes of the present inventions include ability for economical production of these electrodes in combination with rapid time response (within several seconds) with increased sensitivity over electrodes described in publications.

In the presence of certain substrates, such as phenyl valerate, functional NTE hydrolyzes phenyl valerate yielding an amount of phenol proportional to the functional activity of NTE. Tyrosinase then converts phenol to o-quionone, see, schematic in FIG. 8A. O-quionone then generates an electric current, in the presence of electron conducting materials, in proportion to its concentration that is in direct proportion to the initial phenol concentration.

Example IV

Ellipsometry and Electrochemical Impedance Spectroscopy (EIS) Measurements

Ellipsometry and electrochemical impedance spectroscopy (EIS) were used to confirm the deposition of different layers that make up the NEST biosensor. As shown in FIGS. 5A and 5B, the thickness increase following the addition of first PLL and Tyr bilayer was approximately 9.3±0.4 nm. Thickness increased for each of the next two PLL-Tyr bilayers at the same amount and equal to approximately 7.2±0.3 nm. The thickness further increased following the addition of final PLL-NEST bilayer of approximately 6.6±0.3 nm. EIS measurements in the presence of the negatively charged redox couple $[Fe(CN)_6]3-/4-$, were made on the gold electrode to probe the electrical properties of resulting films and provide further evidence of biosensor interface assembly. FIG. 5C shows the Nyquist plots obtained on a bare gold electrode following the successive addition of the following layers: thioctic acid (curve a), PLL-Tyr first bilayer (curve b), PLL-Tyr second bilayer (curve c), PLL-Tyr third bilayer (curve d), and PLL and NEST final bilayer (curve e). Nyquist plots were fitted with Randles equivalent circuit shown in FIG. 6. This circuit produced a semicircle at higher frequencies and a straight line at low frequencies. The semicircle at higher frequencies is related to the parallel combination of double-layer capacitance (Cdl) and charge transfer resistance (Rct). For this system, the Rct value was approximately equal to the diameter of the semicircle. At lower frequencies, a straight line results, at angle of 45° to the x-axis, that is related to the Warburg-diffusion impedance (Zw). In other words, at high frequencies (short time scales), the impedance is controlled by electron-transfer kinetics, and at low frequencies (long time scales), the impedance is diffusion-controlled. The Rct value is thought to be controlled by the thickness of the multilayered polymer assembly." (Harris, et al. (2000) Langmuir, 16:2006-2013; Pardo-Yissar, et al. (2001) Langmuir, 17:1110-1118; all of which are herein incorporated by reference). The Randles equivalent circuit model was fitted to impedance plots to obtain the values of different parameters such as Rct, Cdl, Zw, and solution resistance, Rs. The average best-fit values of Ret are shown in Table 1.1. As expected, the Rct (which is also approximately equal to the diameter of the semicircle domain in the impedance spectra plotted as a Nyquist diagram), increased upon the successive addition of layers, due to increasing barriers for electron exchange between the conductive support and solubilized redox probe.

In summary, a phenyl valerate substrate demonstrated the highest current sensitivity for bi-enzyme electrodes consisting of the enzymes Tyrosinase and NEST, and for bi-enzyme electrodes containing tyrosinase and butyrylcholinesterase. In contrast, phenyl acetate demonstrated the highest sensitivity for bi-enzyme electrodes containing tyrosinase and acetylcholinesterase.

TABLE 1-1

The average best-fit values of $R_{ct}$ for different layers present on the gold electrode.*

| Different layers | Average $R_{ct}(\Omega cm^2)$ |
|---|---|
| Thioctic acid | 270 ± 60 |
| Thioctic acid-(PLL-Tyr)$_1$ | 990 ± 150 |
| Thioctic acid-(PLL-Tyr)$_2$ | 1570 ± 190 |
| Thioctic acid-(PLL-Tyr)$_3$ | 2334 ± 220 |
| Thioctic acid-(PLL-Tyr)$_3$(PLL-NEST)$_1$ | 3150 ± 300 |

Figure 6:
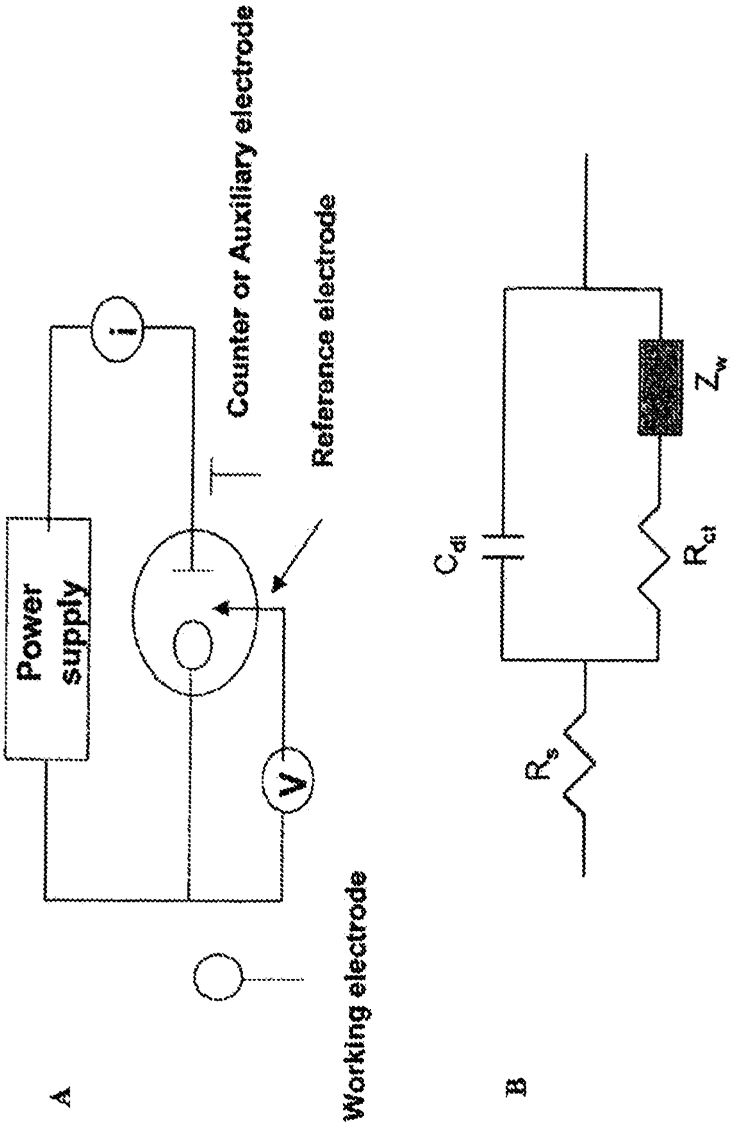
FIG. 6 shows an exemplary schematic of a sensing technique comprising step voltammetry (A) and shows an exemplary schematic of a Randles equivalent circuit comprising a double-layer capacitance ($C_{dl}$), charge transfer resistance ($R_{et}$), solution resistance ($R_s$) and Warburg impedance ($Z_w$) of the present inventions (B).

*The values were obtained by fitting the experimental data (FIG. 5C) to the equivalent circuit shown in FIG. 6 using Z-view.

Example V

The electrodes were tested by dipping each one in phosphate buffer (0.1 M, pH 7.0) containing test molecules. The resulting electrode signals were measured by electrically combining the electrode with a BAS-50 W electrochemical analyzer that maintained the electrode at a constant potential of −100 mV (vs. Ag/AgCl). An exemplary circuit diagram of the present invention is shown in FIG. 6. In one test for measuring NTE esterase activity, a small aliquot of 8 μM phenyl valerate was added to a stirred buffer solution containing the biosensor, and the resulting current was recorded.

Example VI

Amperometric Response Dependence of Current Response on Working Potential and pH.

Figure 7A:
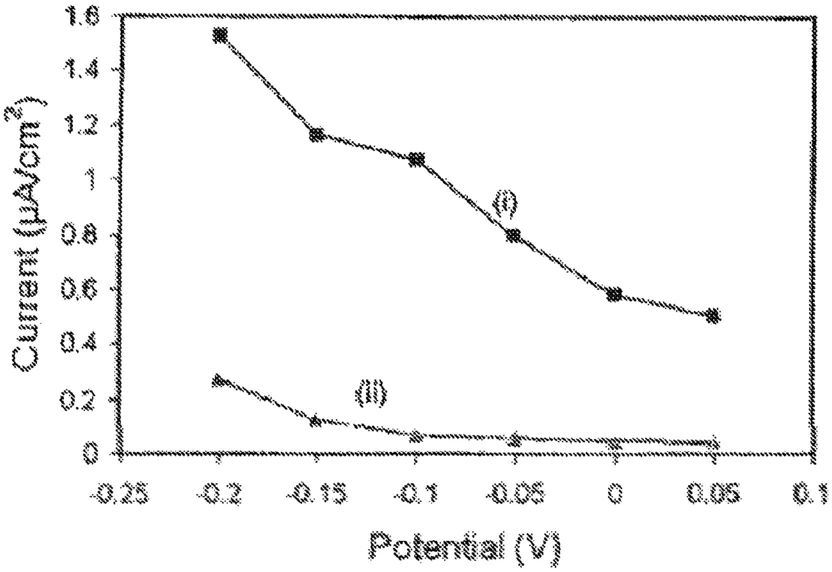
FIGS. 7A-7B show exemplary effects of a working potential on the response current of an esterase enzyme electrode in FIG. 7A using 0.1 M phosphate buffer (pH 7.0) with (i) and without (ii) 12 μM phenyl valerate solution in 0.1 M phosphate buffer at an applied potential of −0.1 V vs. Ag/AgCl reference electrode, and in FIG. 7B an exemplary effect of pH on the response current of an electrode of the present invention, in the presence of 12 μM phenyl valerate solution, in 0.1 M phosphate buffer at an applied potential of −0.1 V vs. Ag/AgCl reference electrode.

The various experimental parameters (such as pH and applied potential), which can affect the amperometric determination of phenyl valerate, were optimized. The effect of applied potential on the amperometric response of the sensor was tested in the range between 0.05 and −0.20 V (FIG. 7A). FIG. 7A shows the steady state response of the biosensor both in the presence and absence (background current) of phenyl valerate. The background current was thought to result largely from the direct reduction of dissolved oxygen in the substrate solution. The highest signal-to background (noise) ratio was obtained at −0.1 V. At working potential more negative then −0.1 V, higher signals were obtained, but the background current also distinctly increased. Therefore, a working potential of −0.1 V was used for further studies.

Figure 7B:
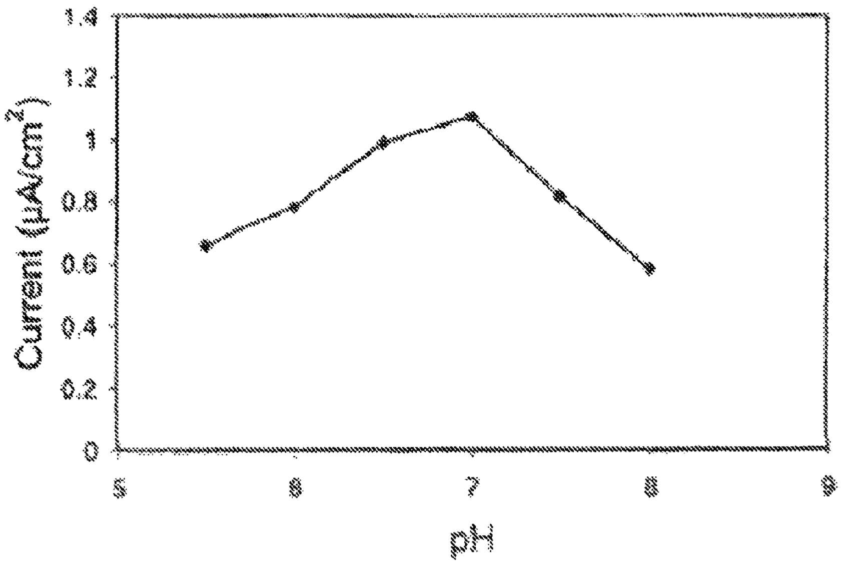

The effect of pH was also studied in the pH range 5.5 to 8.0 in 0.1 M phosphate buffer at working potential of −0.1 Volts. As shown in FIG. 7B, the response current attained a maximum value at pH 7.0. Therefore, pH 7.0 was used for the following studies.

Example VII

Measurement of Esterase Activity Using a NEST Biosensor.

Figure 8E:
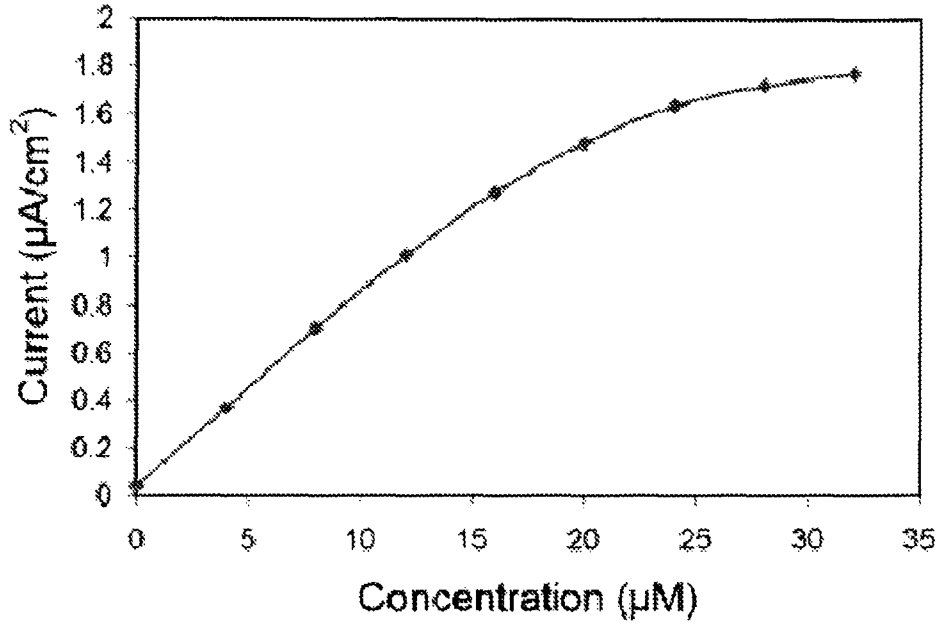

An exemplary current-time response under optimal experimental conditions was obtained after successive additions of equal aliquots of 4 μM phenyl valerate to the phosphate buffer (FIG. 8D). The response time of the electrode was less then 20 s, and further, a well-defined step increase in current indicated a response time less than 10 seconds. The bionsensor's rapid response was contemplated due to the nano-scale thickness of the biosensor interface. An exemplary well-defined reduction current, proportional to the amount of phenyl valerate, was observed (FIG. 7A). The current increase in response to phenyl valerate was linear (r=0.991) in the range 0.5 μM to 12 μM, ($R^2$=0.981) and reached saturation at approximately 30 μM (FIG. 8E). The limit of detection was 0.5 μM at a signal-to-noise ratio of three.

Figure 3C:
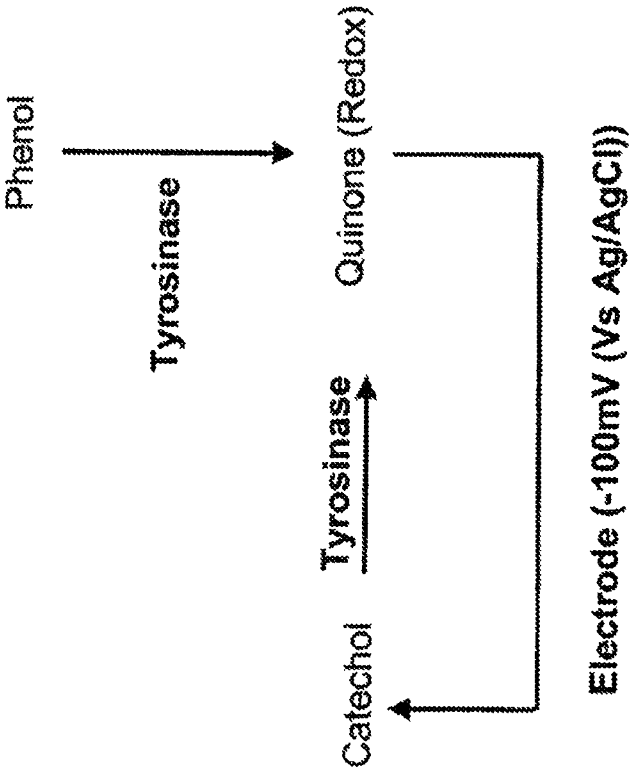
Figure 3D:
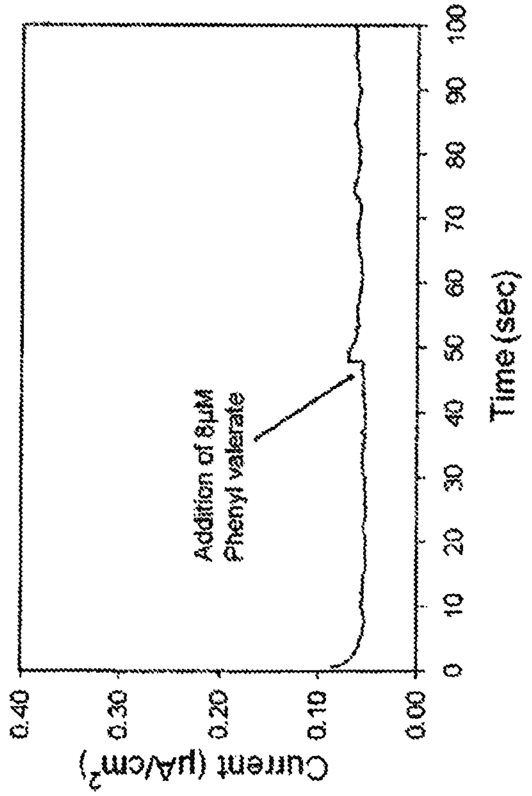

The reproducibility of the sensor was investigated at a phenyl valerate concentration of 4 μM using a mean current of approximately 348 nA $cm^{-2}$, with a relative standard deviation of 9.9% (approximately 10%) with n=10 electrodes. FIG. 3C shows a control experiment using an electrode with poly-L-lysine and tyrosinase bilayers without NEST (FIG. 3A) or with NEST (FIG. 8D). As expected, a relatively very small rise in steady state current was observed on the addition of phenyl valerate (FIG. 3D). The small rise from the electrode test without NEST was attributed to the presence of small amount of phenol produced due to auto hydrolysis of phenyl valerate solution.

Example VIII

Amperometric Response to Catechol and Phenol.

Figure 3E:
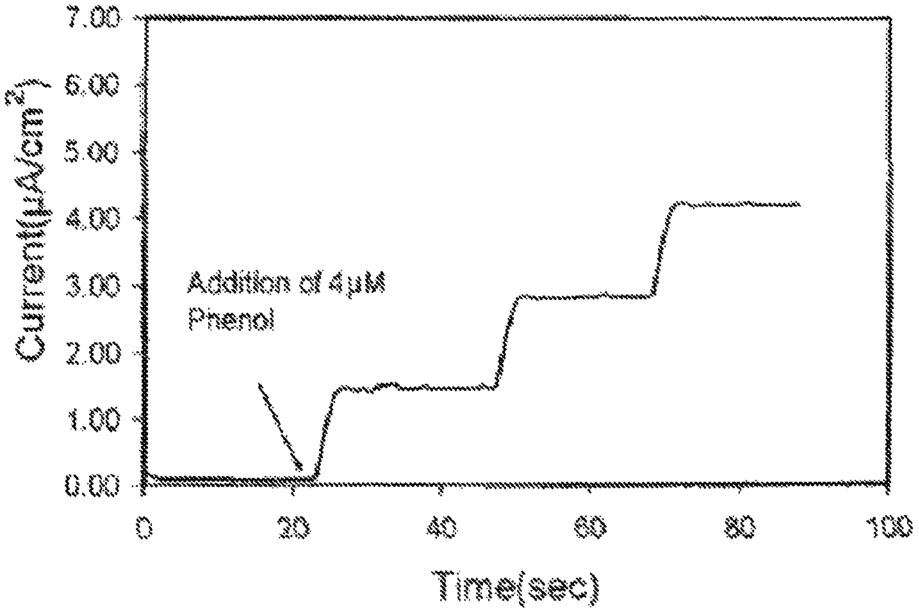
Figure 3F:
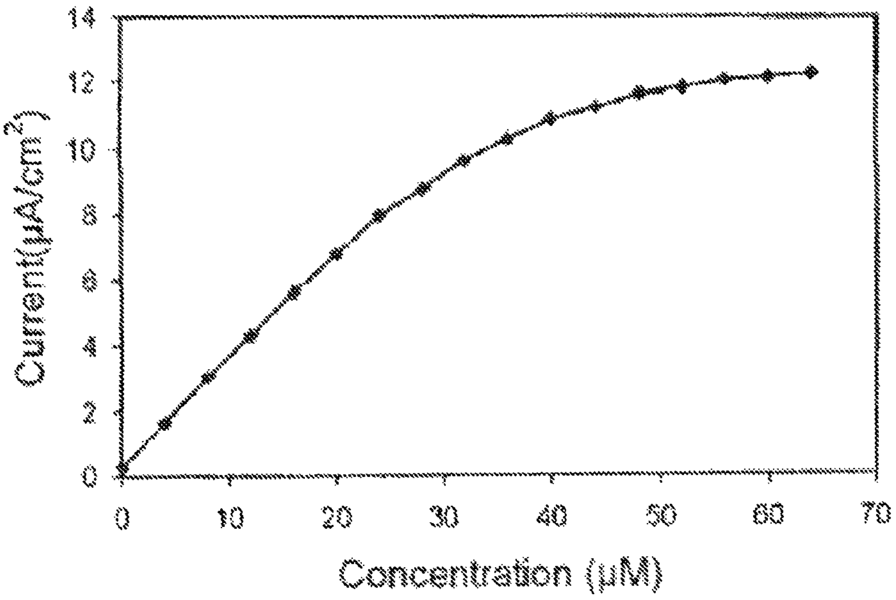

Since tyrosinase can convert both catechol and phenol to quinone, the amperometric response of the NEST biosensor to these compounds was also studied. FIG. 3E shows an exemplary current-time response curve after the successive addition of aliquots of 4 μM phenol. FIG. 8B shows an exemplary current-time response curve after the successive addition of aliquots of 8 μM catechol, showing a corresponding phenol and catechol calibration curves FIGS. 3F and 8C, respectively. The response to phenol was linear (t=0.990) in the range 1 μM to 25 μM, with an average sensitivity of approximately (410±30) nAμ$M^{-1}$ $cm^{-2}$. Saturation was reached at approximately 75 μM. On the other hand, the response to catechol was linear in the range 1 μM to 40 μM, with a sensitivity of (2.5±0.1) μAμ$M^{-1}$ $cm^{-2}$. Saturation was reached at approximately 85 μM.

Example IX

Measuring Inhibition of the Esterase Activity.

A known quantity of phenylnlethylsulfonyl fluoride (PMSF), a compound previously shown to inhibit NTE esterase activity, was added to the phosphate buffer solution, to measure the resulting drop in current. The measured drop was found to be dose-dependent on PMSF concentration (see, FIGS. 8H-8K).

Figure 8F:
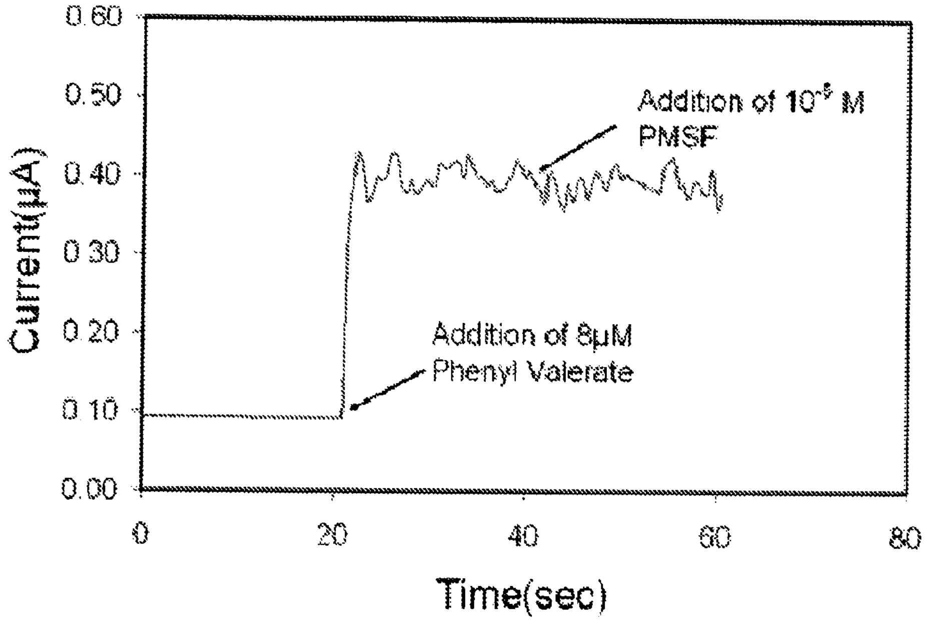
Figure 8G:
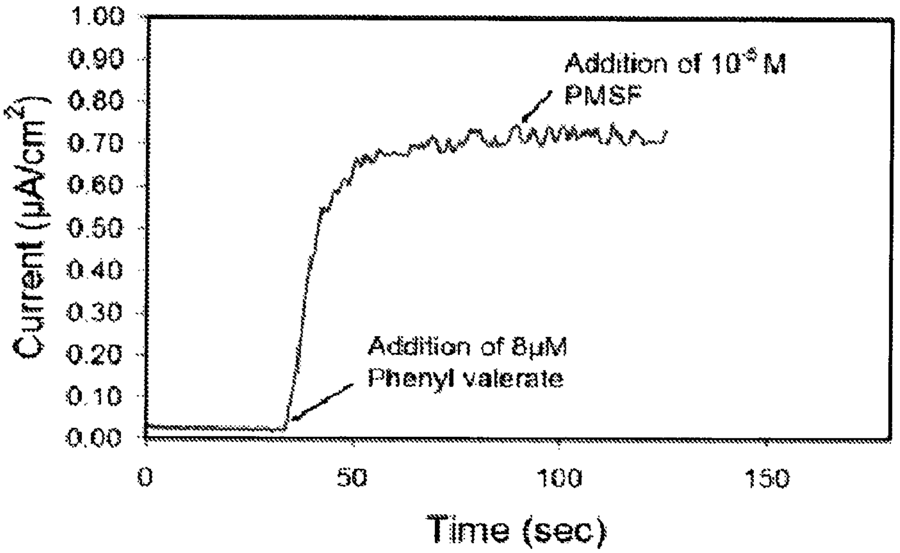
Figure 8H:
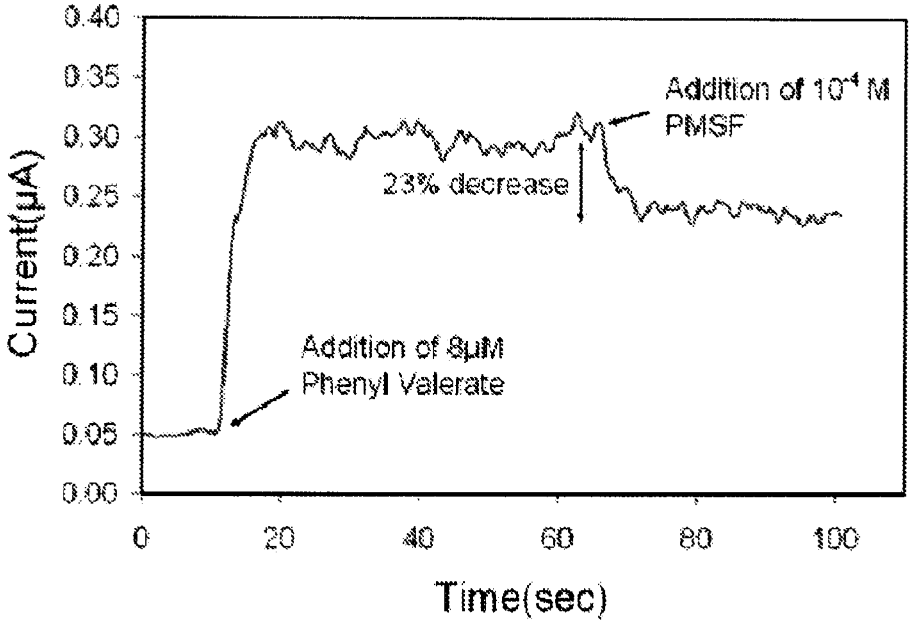
Figure 8I:
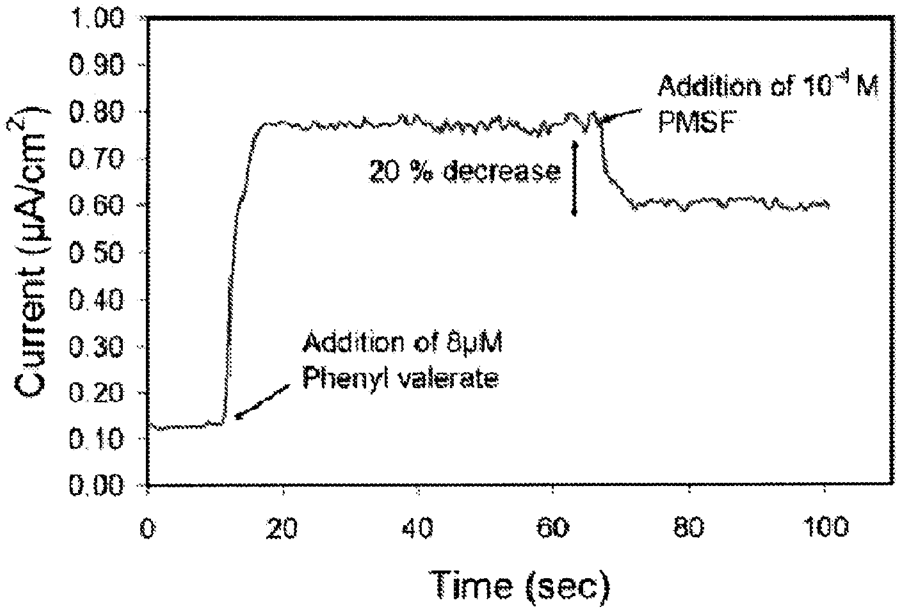
Figure 8J:
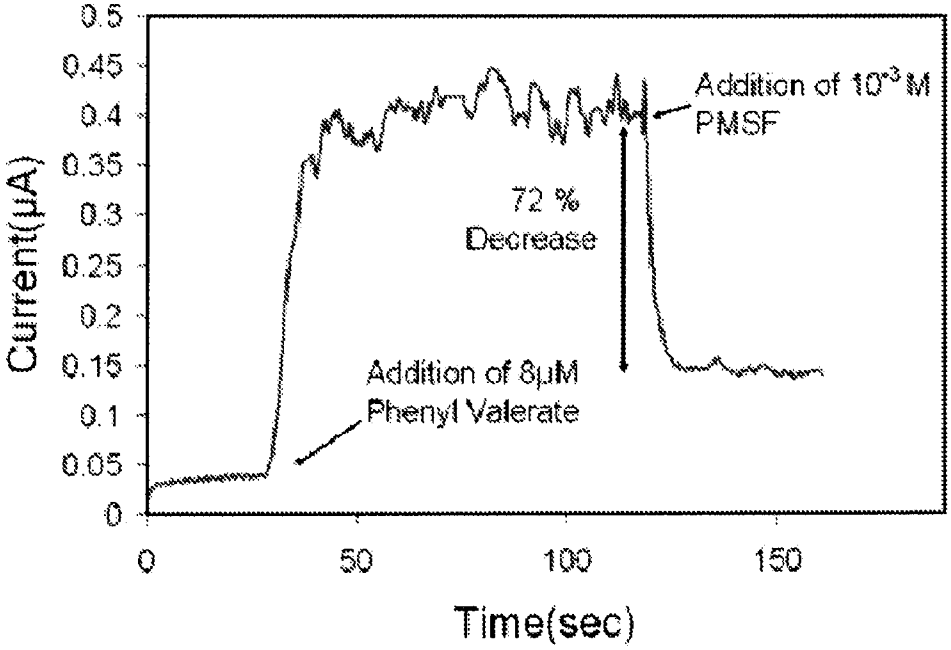
Figure 8K:
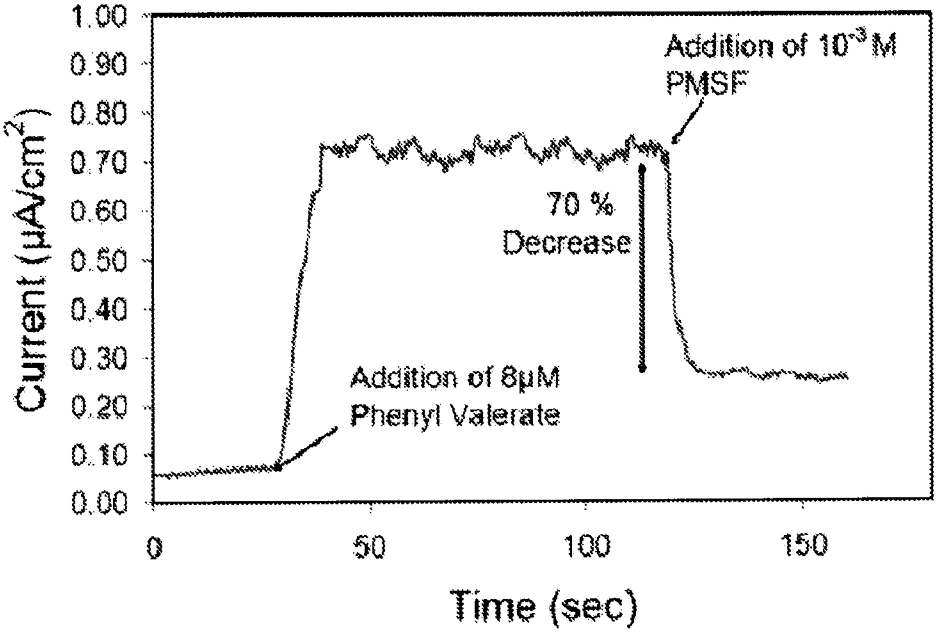

Specifically, the inventor's measured inhibition of the esterase activity after immersing an electrode of the present inventions into a phosphate buffer solution, then adding an aliquot of phenyl valerate to activate an NTE generated current. After a steady biosensor signal was obtained, a known quantity of phenylmethylsulfonyl fluoride (PMSF), a non-neuropathic compound previously shown to inhibit NEST (and NTE) esterase activity, was added to the phosphate buffer solution after which a drop in current was measured following a sufficient addition of amount of inhibitor. As shown in FIGS. 8F and 8G, there was no decrease on the addition of 10 μM PMSF, a 20% (±3%) decrease in response to the addition of 100 μM PMSF, see, FIGS. 8H and 8I, and a 70% (±4%) decrease on the addition of 1000 μM PMSF, see, FIGS. 8J and 8K. PMSF inhibition of NEST esterase activity reduced the amount of phenol and subsequently o-quinone produced. Therefore, less o-quinone was reduced at the electrode surface resulting in a lowered current. The inventors observed a similar dose-dependent drop in current after a neuropathic OP compound, MIPAFOX (50 mM mipafox), was added to the phosphate buffer. These results demonstrated that a NEST biosensor of the present inventions were used for dose dependent detection of NEST inhibitors.

Example X

Storage Stability Tests.

The following example demonstrates storage stability of the biosensors for at least one month. The storage stability of the sensors provided using methods described herein, were tested by storing at 4° C. in phosphate buffer, pH 7.0. The electrode was used at least once a day for over 30 days to obtain measurements of a current response to a chosen concentration of phenyl valerate standard solution. The results showed that the activity of sensor remained stable for a month and then reduced gradually, with a half-life of 12 days.

Example XI

Immobilization of Acetylcholinesterase and Butyrylcholinesterase.

Figure 9:
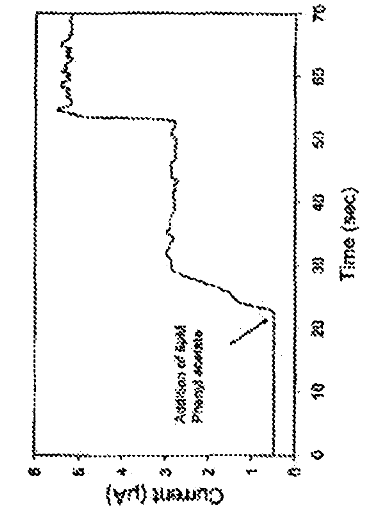
FIG. 9 shows an exemplary current time response of a bi-enzyme electrode, wherein the 2 enzymes consist of tyrosinase and acetylcholinesterase, following the addition of aliquots of 8 μM phenyl acetate, in 0.1 M phosphate buffer, pH 7.0, at an applied potential of −0.1 V (vs Ag/AgCl).

During the course of providing a biosensor of the present inventions, the inventors used the same PLL-Tyr multilayer interface to immobilize and measure the activity of other esterases such as acetylcholinesterase and butyrylcholinesterase in place of NEST. A typical current-time response, for a bi-enzyme electrode consisting of tyrosinase and acetylcholinesterase, after the successive addition of aliquots of 8 μM phenyl acetate to the phosphate buffer is shown in FIG. 9. A response to phenyl acetate was found to be linear (r=0.989) in the range 0.5 μM to 16 μM. The response reached saturation at approximately 40 μM. However, no significant rise in current was observed when phenyl valerate instead of phenyl acetate was used as a substrate on this interface. These results demonstrated that phenyl acetate provides a better substrate for acetylcholinesterase than phenyl valerate. Current time response curves were also obtained with a bi-enzyme electrode consisting of tyrosinase and butyrylcholinesterase, with the highest current sensitivity being obtained when phenyl valerate was used as a substrate (results similar to exemplary FIG. 9). Table 1-2 summarizes the current sensitivities obtained with three different bi-enzyme interfaces. Control experiments were done in which each of the substrates was exposed to a gold electrode containing PLL-Tyr bilayers without an esterase layer. The current sensitivities obtained in these control experiments were always less than 0.5 nAμM$^{-1}$ cm$^{-2}$. Collectively, these interfaces were used for simultaneously detecting the presence of a variety of compounds that inhibit cholinesterases in addition to studying kinetics of cholinesterase reactions.

Example XII

Experimental Results Obtained from Mathematical Models of Biosensor Function.

Mathematical models demonstrating mass transfer and reactions at the biosensor interface of an NTE esterase electrode were developed for use in the present inventions. These models were used to elucidate the fundamental nanoscale phenomena that govern performance of the biosensors of the present inventions. These models comprised mass balance equations for each of phenyl valerate, phenol, catechol, and o-quinone, see, FIGS. 13-15. These mathematical models developed and used during the development of the present inventions predicted a five-fold signal amplification via recycling in the prototype NTE esterase biosensor.

Figure 10:
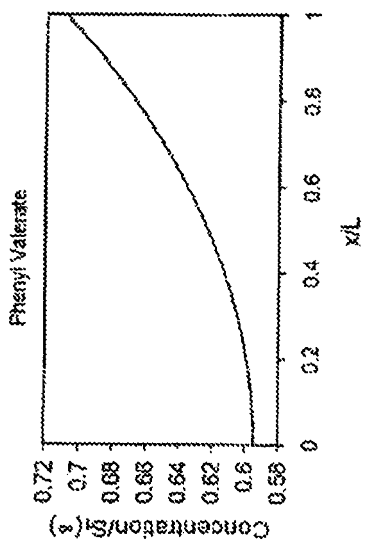
FIGS. 10A-10C show exemplary concentration profiles of phenyl valerate in FIG. 10A, and in FIGS. 10B and 10C of catechol, o-quinone, and phenol across a biosensor interface of the present invention as predicted by a mathematical model as described herein.
Figure 10B:
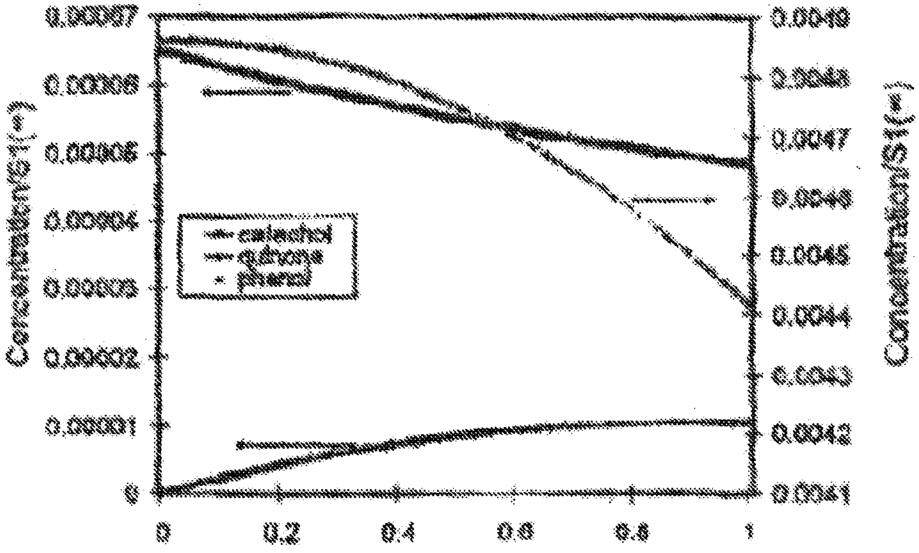
Figure 10C:
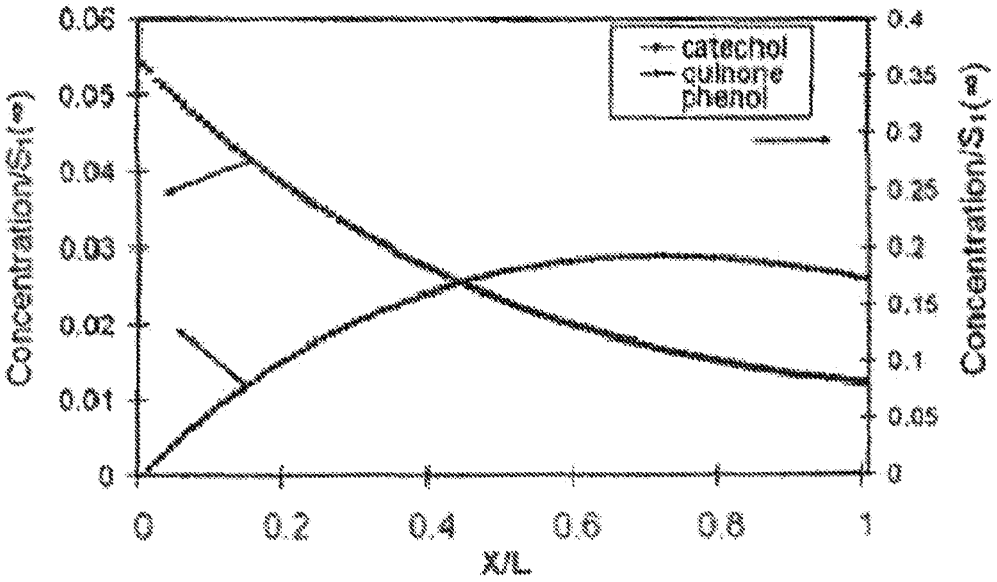
Figure 11:
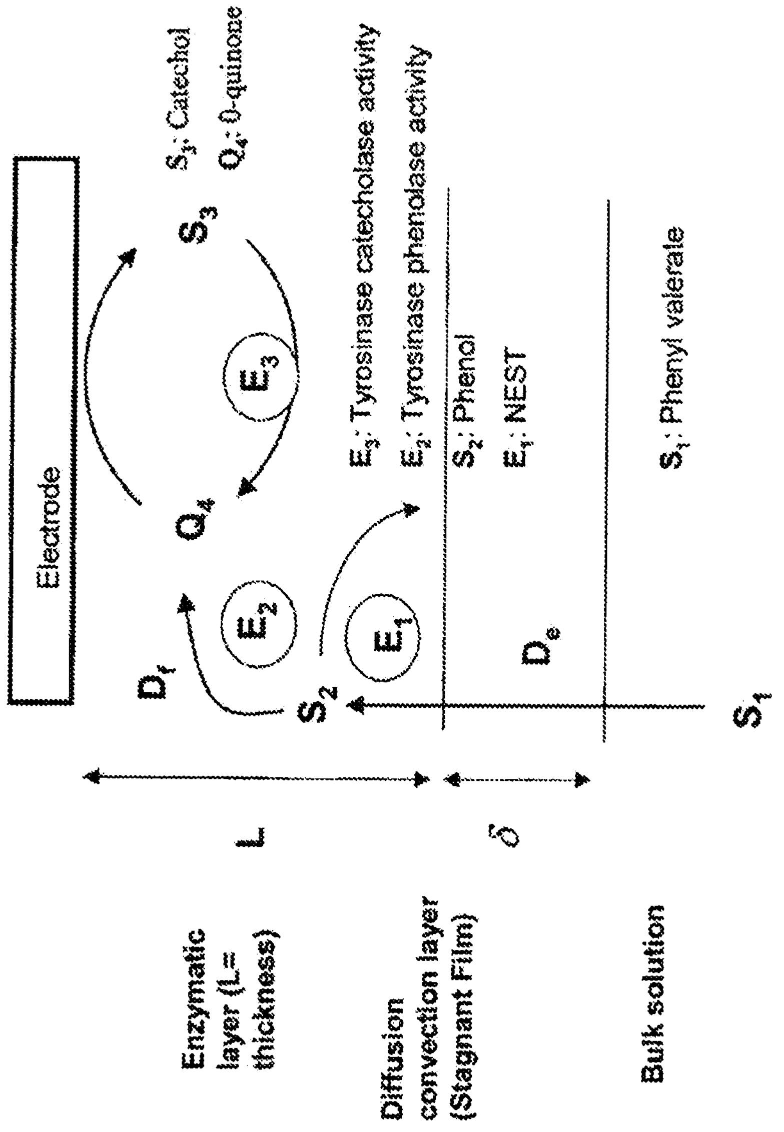
FIGS. 11A-11D show an exemplary schematic illustration of signal amplification using a recycle mechanism of a biosensor comprising NEST in FIG. 11A, and in FIGS. 11B and 11C, exemplary effects of specific amounts of NEST (θ1) and tyrosinase (θ3) activities on interface current, with actual results superimposed on a prediction model in FIG. 11D.
Figure 11B:
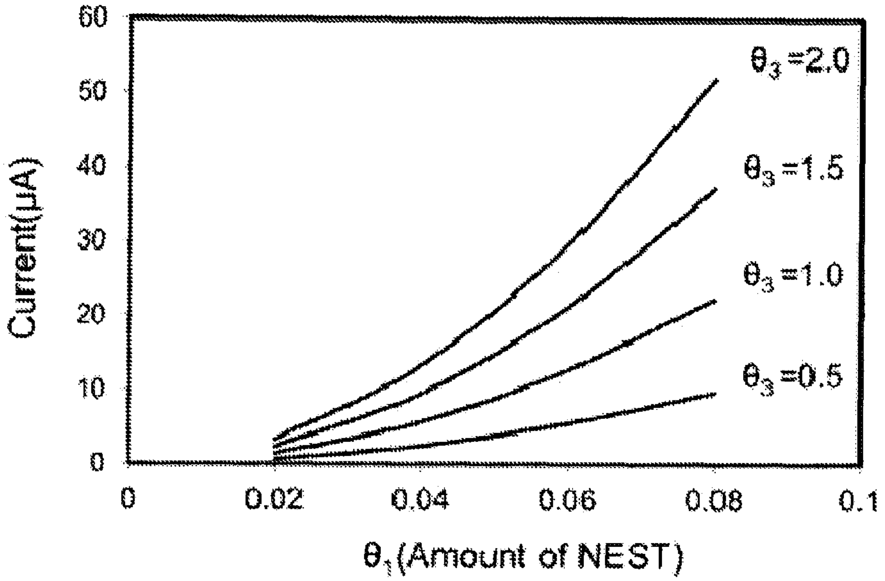
Figure 11C:
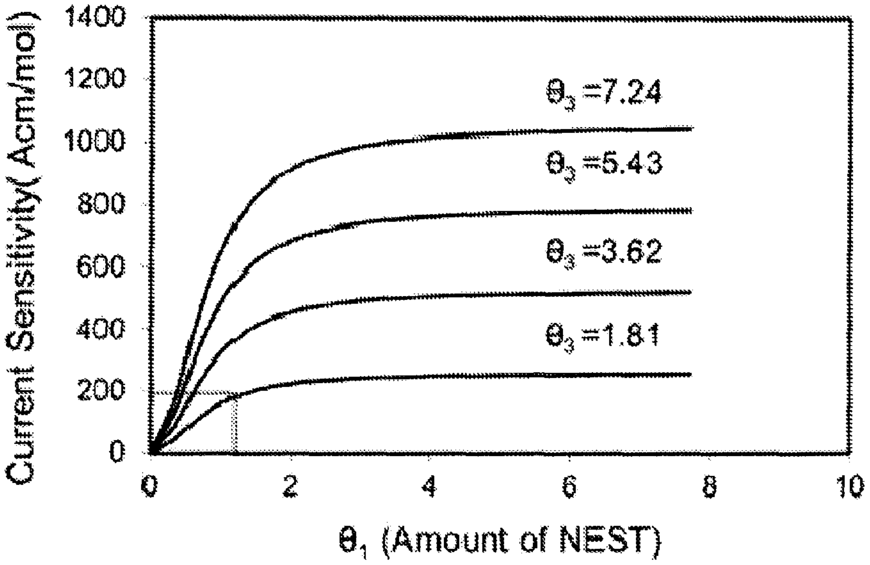
Figure 11D:
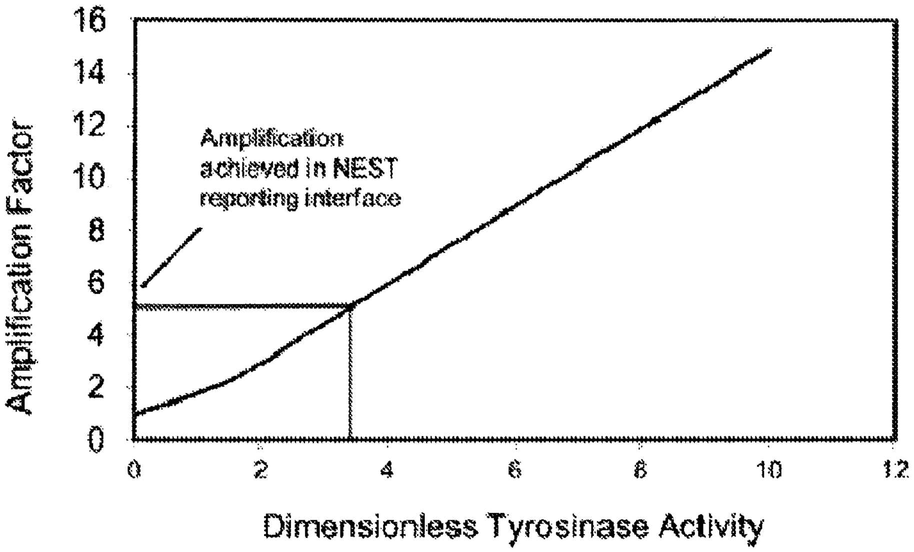

Analytical solutions to these equations were charted which demonstrated the concentration profiles of phenyl valerate, phenol, catechol, and quinone as a function of relative position (x/L) within the biosensor interface, as well as current density as a function of phenyl valerate bulk concentration, as a Sherwood number and Thiele modulus. Example concentration profiles for catechol, quinone, and phenol based on reasonable values of parameters are shown in FIGS. 10 and 11, normalized to the bulk concentration of the phenyl valerate substrate. The current produced by the reporting interface as a function of amount of NTE esterase loading (θ1) and amount of tyrosinase loading (θ3) is predicted by the model (FIGS. 11B and 11C), allowing the model to assist the inventors in optimizing operational characteristics of the interface. Thus the inventors designed biosensors of the present inventions to achieve greater signal amplification for dramatically increased sensitivity of the biosensor. Amplification was achieved by electrochemically recycling the enzymatic reaction product (quinone) back to the intermediate (catechol) for re-use as a tyrosinase substrate.

TABLE 1-2

Exemplary performance of bi-enzyme electrodes of the present inventions consisting of tyrosinase with an esterase or a phosphatase in the presence of a substrate.

| Enzyme | Substrate used | Average sensitivity (nAμM$^{-1}$cm$^{-2}$) |
|---|---|---|
| NEST | Phenyl valerate | 87 ± 8 |
| Acetylcholinesterase | Phenyl acetate | 180 ± 25 |
| Butyrylcholinesterase | Phenyl valerate | 25 ± 10 |

| Enzyme | Substrate Used | Average sensitivity (nAμM$^{-1}$cm$^{-2}$) | Average sensitivity (control experiments) (nAμM$^{-1}$cm$^{-2}$) |
|---|---|---|---|
| NEST | Phenyl valerate | 88 ± 6 | 0.5 |
| Acetylcholinesterase | Phenyl acetate | 180 ± 8 | 0.4 |
| Butyrylcholinesterase | Phenyl valerate | 70 ± 5 | 0.3 |
| Alkaline phosphatase | Phenyl phosphate | 236 ± 10 | 0.3 |

Example XIII

This example presents a theoretical model for an actual bi-enzyme rotating disk electrode consisting of NEST and tyrosinase as described in Example III. The molecular architecture of the bi-enzyme electrode is shown in FIG. 4. In this model, as in the previous Examples demonstrating stationary electrodes, a NEST protein converts phenyl valerate to phenol, which is converted to o-quinone by tyrosinase. The o-quinone is electrochemically reduced to catechol at the electrode's surface, resulting in current. A portion of the catechol produced is then converted to o-quinone by tyrosinase. Catechol thus serves as shuttle analyte that can undergo successive cycles of enzymatic oxidation-electrochemical reduction (substrate recycling), resulting in an amplification of biosensor's response.

This theoretical model further comprises the influence of the mass transport, permeation through the enzyme layers and enzyme kinetics. This model is expressed in dimensionless form to minimize the number of constants that must be evaluated. The biosensor was assembled on a rotating disk electrode, and the biosensor's performance was measured at a variety of rotational velocities and substrate concentrations to evaluate the constants and validate the model.

Enzyme Kinetics of the Biosensors of the Present Inventions.

Tyrosinase is a binuclear copper containing enzyme that catalyzes the oxidation of catechols to o-quinone (catecholase activity). For catechol as the substrate, it was reported (Coche-Guerente, Labbe et al. 1999; herein incorporated by reference) that the overall rate (v) in solution was described by Michaelis-Menten formalism (Equation 1.1) with an apparent Michaelis constant $K_m^{app}$=~220 μM.

$$v = \frac{k_{cat}[E_t][S]}{K_m^{app} + S} \quad (1.1)$$

where $E_t$, S and $k_{cat}$ represent the enzyme concentration, catechol concentration and turnover number, respectively.

In contrast, the experiments conducted in the course of developing the present inventions involve substrate concentrations around two orders of magnitude less than $K_m^{app}$. Thus kinetics were contemplated herein to be first order relative to the substrate concentration.

Besides of its catecholase activity, tyrosinase is also able to catalyze orthohydroxylation (monophenolase activity) of monophenols to o-diphenols (catechols) that, in turn, are oxidized to corresponding o-quinones (catecholase activity). Because the hydroxylation activity of tyrosinase is expressed in conjunction with oxidation of o-diphenol to its o-quinone, some authors have defined monophenolase activity as the complete conversion of monophenols to o-quinone. Indeed, the hydroxylation step proceeds and has been shown to be much slower than the oxidation of o-diphenol to o-quinone and is therefore considered to be the rate limiting (Coche-Guerente, Labbe et al. 2001; herein incorporated by reference). The enzymatic oxidation of phenol to o-quinone has also been shown to follow Michaelis-Menten formalism (Coche-Guerente, Labbe et al. 2001; herein incorporated by reference), with an apparent $K_m^{app}$ of ~250 μM in homogeneous solution.

Similarly, the esterase activity of NTE (or NEST) can convert phenyl valerate to phenol, and for simplicity, this reaction is suggested to follow Michaelis-Menten formalism.

Modeling Criteria for Efficiency of Rotating Disk Electrodes.

FIG. 11A is a schematic representation of a bi-enzyme rotating disk electrode, modified with an enzyme layer that contains NEST and tyrosinase, and has a thickness L. The sequential steps that lead to an electrochemical signal in the presence of phenyl valerate substrate $S_1$ are as follows:

(1) Mass transfer of phenyl valerate ($S_1$), phenol ($S_2$), catechol ($S_3$), and quinone ($Q_4$ through a stagnant film between the bulk and the enzyme layer. For rotating disk electrode, this film has a thickness $\delta=1.61D_e^{1/3}\nu^{1/6}\omega^{-1/2}$ (Coche-Guerente, Labbe et al. 1999; herein incorporated by reference). where $D_e$, ν and ω represent the diffusion coefficient, kinematic viscosity and rotation speed, respectively. For simplicity, the diffusion coefficients of $S_1$, $S_2$, $S_3$ and $Q_4$ in the bulk aqueous phase and stagnant film were assumed to be identical ($D_e$).

(2) Partitioning of $S_1$, $S_2$, $S_3$ and $Q_4$ from the stagnant film into the enzyme layer. The kinetics of partitioning were assumed to be rapid so that the interfacial concentrations in the film and enzyme layers remained at equilibrium. The partition coefficients ($k_p$) were assumed to be identical for $S_1$, $S_2$, $S_3$ and $Q_4$. Thus, yielding the following equilibrium expressions.

$$[S_1]_{L-}=k_p[S_1]_{L+} \quad (1.2)$$

$$[S_2]_{L-}=k_p[S_2]_{L+} \quad (1.3)$$

$$[S_3]_{L-}=k_p[S_3]_{L+} \quad (1.4)$$

$$[Q_4]_{L-}=k_p[Q_4]_{L+} \quad (1.5)$$

(3) Diffusion of $S_1$, $S_2$, $S_3$ and $Q_4$ within the enzymatic layer of thickness L. The enzymatic layer was assumed to behave like a semi-permeable membrane. The model was simplified by assuming an identical diffusion coefficient ($D_f$) for $S_1$, $S_2$, $S_3$ and $Q_4$.

(4) At steady state conditions, all the substrates $S_1$, $S_2$, $S_3$ and $Q_4$ are present in the enzymatic layer, although only $S_1$ is present in the bulk solution. Inside the enzyme layer, for low concentrations of phenyl valerate, the conversion of phenyl valerate ($S_1$) to phenol can be given by the following first order equation:

$$v_1 = \frac{k_1[E_1][S_1]}{K_1} \quad (1.6)$$

where $E_1$ denotes the total concentration of active NEST, and $K_1$ is the apparent $K_m$ value. The rate of conversion of phenol to o-quinone and catechol to o-quinone has been shown to be given by similar first order expressions (Coche-Guerente, et al. 1999, Cochc-Guerente et al. 2001; herein incorporated by reference):

$$v_2 = \frac{k_2[E_2][S_2]}{K_2} \quad (1.7)$$

$$v_3 = \frac{k_3[E_3][S_3]}{K_3} \quad (1.8)$$

Where, $E_2$ and $E_3$ represent the concentrations of monophenolase and catecholase active sites, respectively.

(5) Electrode potential was assumed to be sufficiently negative so that the electrochemical reduction step is not rate limiting.

Model equations based upon criteria presented above.

Using the same approach as the one already reported in a theoretical treatment of biosensors (Bartlett and Whitaker 1987; Coche-Guerente, Labbe et al. 1999; Coche-Guerente, Labbe et al. 2001; herein incorporated by reference), the equations describing the concentrations of $S_1$, $S_2$, $S_3$ and $Q_4$ at steady state are as follows:

$$\frac{\partial^2 S_1}{\partial x^2} - \frac{S_1}{\lambda_1^2} = 0 \quad (1.9)$$

$$\frac{\partial^2 S_2}{\partial x^2} - \frac{S_2}{\lambda_2^2} + \frac{S_1}{\lambda_1^2} = 0 \quad (1.10)$$

$$\frac{\partial^2 S_3}{\partial x^2} - \frac{S_3}{\lambda_3^2} = 0 \quad (1.11)$$

$$\frac{\partial^2 Q_4}{\partial x^2} + \frac{S_2}{\lambda_2^2} + \frac{S_3}{\lambda_3^2} = 0 \quad (1.12)$$

where x is the distance from electrode surface. As defined below, $\lambda_1$, $\lambda_2$ and $\lambda_3$ represent the reaction lengths (Coche-Guerente, Labbe et al. 1999; herein incorporated by refer ence) related to phenyl valerate ($S_1$), phenol ($S_2$), and catechol ($S_3$):

$$\lambda_1 = \left(\frac{D_f K_1}{k_1 E_1}\right)^{\frac{1}{2}} \quad \lambda_2 = \left(\frac{D_f K_2}{k_2 E_2}\right)^{\frac{1}{2}} \quad \lambda_3 = \left(\frac{D_f K_3}{k_3 E_3}\right)^{\frac{1}{2}} \tag{1.13}$$

Boundary Conditions of Concentration Profiles as Determined Herein.

To determine concentration profiles within the enzyme layer, equations 1.9-1.12 were solved with the following boundary conditions:

Applied potential is sufficiently negative that $$[Q_4]_{x=0}=0 \tag{1.14}$$

2) Since Phenyl Valerate and Phenol are not Electro-Active $$\left[\frac{\partial S_1}{\partial x}\right]_{x=0} = 0, \left[\frac{\partial S_2}{\partial x}\right]_{x=0} = 0 \tag{1.15}$$

3) Only Phenyl Valerate is Present in the Bulk $$[S_1]_{x=\infty}=S_1(\infty), [S_2]_{x=\infty}=0, [S_2]_{x=\infty}=0, [Q_4]_{x=\infty}=0 \tag{1.16}$$

At steady state, flux of phenyl valerate, phenol, catechol and quinone across the film equals that entering the enzyme layer.

$$D_f\left[\frac{\partial S_1}{\partial x}\right]_{x=L} = \frac{D_e}{k_p\delta}[k_p S_1(\infty) - [S_1]_{x=L}] \tag{1.17}$$

$$D_f\left[\frac{\partial S_2}{\partial x}\right]_{x=L} = -\frac{D_e}{k_p\delta}[S_2]_{x=L} \tag{1.18}$$

$$D_f\left[\frac{\partial S_3}{\partial x}\right]_{x=L} = -\frac{D_e}{k_p\delta}[S_3]_{x=L} \tag{1.19}$$

$$D_f\left[\frac{\partial Q_4}{\partial x}\right]_{x=L} = -\frac{D_e}{k_p\delta}[Q_4]_{x=L} \tag{1.20}$$

From law of conservation of mass, for any x inside the enzyme layer:

$$[Q_4]+[S_1]+[S_2]+[S_3]=k_p S_1(\infty) \tag{1.21}$$

$$\text{6) Current density} = J = \frac{i}{A} = -nFD_f\left[\frac{\partial S_3}{\partial x}\right]_{x=0} = nFD_f\left[\frac{\partial Q_4}{\partial x}\right]_{x=0} \tag{1.22}$$

Solution of equations 1.9 to 1.12 gave the following analytical expressions for concentration profiles of $S_1$, $S_2$, $S_3$ and $Q_4$. The following expressions were also confirmed by Mathematica.

$$S_1 = \frac{k_p S_1(\infty)}{\frac{P_m\theta_1}{m_e}\sinh\theta_1 + \cosh\theta_1}\cosh\left(\frac{x}{\lambda_1}\right) \tag{1.23}$$

-continued $$S_2 = \frac{k_p S_1(\infty)}{\frac{P_m\theta_1}{m_e}\sinh\theta_1 + \cosh\theta_1} \left(\frac{\theta_1^2}{\theta_2^2 - \theta_1^2}\right)\left[\cosh\left(\frac{x}{\lambda_1}\right) - \left(\frac{\frac{P_m\theta_1}{m_e}\sinh\theta_1 + \cosh\theta_1}{\frac{P_m\theta_2}{m_e}\sinh\theta_2 + \cosh\theta_2}\right)\cosh\frac{x}{\lambda_2}\right] \tag{1.24}$$

$$S_3 = k_p S_1(\infty)\left[1 - \frac{1}{\frac{P_m\theta_1}{m_e}\sinh\theta_1 + \cosh\theta_1} - \frac{1}{\frac{P_m\theta_1}{m_e}\sinh\theta_1 + \cosh\theta_1} \left(\frac{\theta_1^2}{\theta_2^2 - \theta_1^2}\right) \times \left(1 - \frac{\frac{P_m\theta_1}{m_e}\sinh\theta_1 + \cosh\theta_1}{\frac{P_m\theta_2}{m_e}\sinh\theta_2 + \cosh\theta_2}\right)\right] \times \left[\cosh\frac{x}{\lambda_3} - \frac{\frac{P_m\theta_3}{m_e}\sinh\theta_3 + \cosh\theta_3}{\frac{P_m\theta_3}{m_e}\cosh\theta_3 + \sinh\theta_3}\sinh\frac{x}{\lambda_3}\right] \tag{1.25}$$

$$Q_4 = k_p S_1(\infty) - S_1 - S_2 - S_3 \tag{1.26}$$

$$\text{where } m_e = \frac{D_e}{\delta} \; P_m = \frac{k_p D_f}{L} \; \theta_1 = \frac{L}{\lambda_1}, \theta_2 = \frac{L}{\lambda_2}, \theta_3 = \frac{L}{\lambda_3}$$

$m_e$ is the mass transfer coefficient across the stagnant film, and $P_m$ denotes the permeability inside the enzyme layer. The ratio $$\frac{P_m}{m_e}$$

which compares the mass transfer in enzyme layer to that in bulk is also known as the Sherwood number. The dimensionless parameters $\theta_1$, $\theta_2$, and $\theta_3$, also known as Thiele modulus, compare the enzymatic reaction rates of phenyl valerate, phenol and catechol substrates, respectively, with their diffusion in the enzymatic layer of thickness L.

The cathodic current sensitivity ($S_{pv}^c$); of the electrode toward phenyl valerate substrate was derived from Equations 1.25 and 1.22:

$$S_{pv}^c = \frac{J_{pv}}{S_1(\infty)} = 2FP_m\theta_3\left[1 - \frac{1}{\frac{P_m\theta_1}{m_e}\sinh\theta_1 + \cosh\theta_1} - \frac{1}{\frac{P_m\theta_1}{m_e}\sinh\theta_1 + \cosh\theta_1}\left(\frac{\theta_1^2}{\theta_2^2 - \theta_1^2}\right) \times \left(1 - \frac{\frac{P_m\theta_1}{m_e}\sinh\theta_1 + \cosh\theta_1}{\frac{P_m\theta_2}{m_e}\sinh\theta_2 + \cosh\theta_2}\right)\right] \times \left[\frac{\frac{P_m\theta_3}{m_e}\sinh\theta_3 + \cosh\theta_3}{\frac{P_m\theta_3}{m_e}\cosh\theta_3 + \sinh\theta_3}\right] \tag{1.27}$$

where $S_1(\infty)$ denotes the bulk phenyl valerate concentration. This equation demonstrates that the bio-electrode response is affected by the rate of mass transport in the stagnant film ($m_e$) and the enzyme layer ($P_m$), as well as by the enzymatic activities toward phenyl valerate ($\theta_1$), phenol ($\theta_2$) and catechol ($\theta_3$). Equation 1.27 was derived assuming that only phenyl valerate is present in the bulk. However, if only phenol is present in the bulk, then it has been shown that the following relation can be (Coche-Guerente, Labbe et al. 2001; herein incorporated by reference):

$$S_{ph}^{c}=\frac{J_{ph}}{S_2(\infty)}=2FP_m\theta_3\left(1-\frac{1}{\frac{P_m}{m_e}\theta_2\sinh\theta_2+\cosh\theta_2}\right)\times\left(\frac{\frac{P_m}{m_e}\theta_3\sinh\theta_3+\cosh\theta_3}{\frac{P_m}{m_e}\theta_3\cosh\theta_3+\sinh\theta_3}\right) \quad (1.28)$$

where $S_{ph}^{c}$ and $S_2(\infty)$ denote the phenol sensitivity and bulk concentration, respectively. Similarly, if only catechol is present in the bulk, then the following relations can be derived (Coche-Guerente, et al. 1999; herein incorporated by reference):

$$S_{ct}^{c}=\frac{J_{ct}^{c}}{S_3(\infty)}=-2FP_m\frac{1-\frac{P_m\theta_3}{m_e}\sinh\theta_3-\cosh\theta_3}{\frac{P_m}{m_e}\cosh\theta_3+\frac{\sinh\theta_3}{\theta_3}} \quad (1.29)$$

$$S_{ct}^{a}=\frac{J_{ct}^{a}}{S_3(\infty)}=2FP_m\frac{1}{\frac{P_m}{m_e}\cosh\theta_3+\frac{\sinh\theta_3}{\theta_3}} \quad (1.30)$$

where $S_{ct}^{c}$ denotes the sensitivity of the electrode in the presence of catechol at an applied potential of −0.1 V (where major contribution to current comes from the reduction of o-quinone), and $S_{ct}^{a}$ denotes the sensitivity at an applied potential of 0.5 V (where major contribution to current comes from oxidation of catechol which couldn't be converted to o-quinone by tyrosinase). For rotating disk electrodes we can assume $m_e$ to be given by the following Levich equation (Coche-Guerente, et al. 1999; herein incorporated by reference):

$$m_e=\frac{D_e^{2/3}}{1.613\nu^{1/6}\omega^{-1/2}} \quad (1.31)$$

On rearranging equations 1.29 and 1.30 and substituting the value of $m_e$ from equation 1.31, the following relations can be obtained. The following relations were used by us (data shown in the next section) to validate the model and also estimate some parameters.

$$\frac{S_{ct}^{c}}{S_{ct}^{a}}=(-1+\cosh\theta_3)+(1.613P_mD_e^{-2/3}\nu^{1/6}\theta_3\sinh\theta_3)\omega^{-\frac{1}{2}} \quad (1.32)$$

$$\frac{1}{S_{ct}^{a}}=\left(\frac{1}{2FP_m}\frac{\sinh\theta_3}{\theta_3}\right)+\left(1.613\frac{D_e^{-2/3}\nu^{1/6}\cosh\theta_3}{2F}\right)\omega^{-\frac{1}{2}} \quad (1.33)$$

Example IVX

This example describes the preparation and use of a biosensor of the present invention using a rotating disk electrode.

Figure 4B:
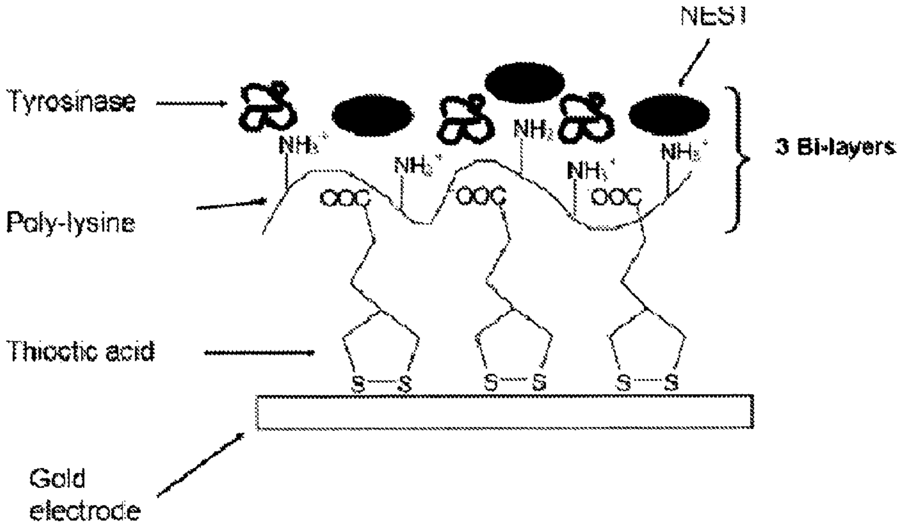
Figure 4C:
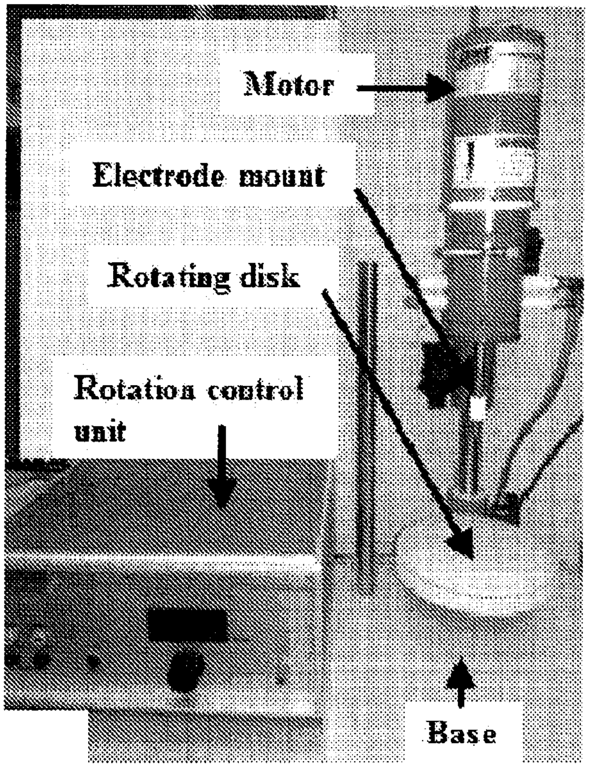
Figure 4D:
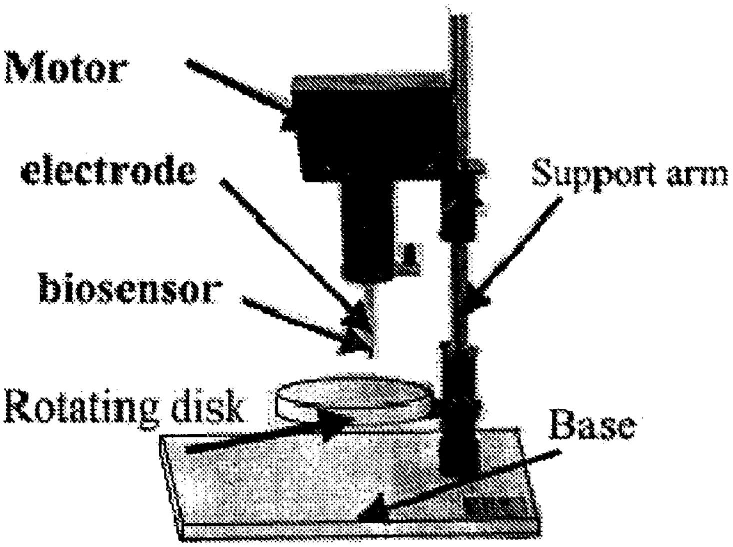

Preparation of a Rotating Gold Electrode for Use with the Present Inventions:

The molecular architecture of the biosensor is shown schematically in FIG. 4B. Gold rotating disk electrodes (electrodes capable of being mechanically rotated) (Metrohm Limited, Herisau, Switzerland) were polished with alumina powder and dipped in 5 mM solution of thioctic acid in ethanol for 30 min. The electrodes were washed with ethanol, dried under nitrogen and dipped in PLL solution for 45 min. The PLL solution was prepared by adding 12 mg of polylysine in 50 ml of 20 mM phosphate buffer (pH 8.5). The electrodes were then rinsed with water and dipped in equimolar solution of tyrosinase and NEST in 0.1 M phosphate buffer for 45 min. The last two steps were repeated 3 times to create 3 bilayers of PLL and tyrosinase/NEST. The electrodes were then washed with water, dried under nitrogen and dipped in phosphate buffer (0.1 M, pH 7.0) for testing. These experiments were done at room temperature.

Chronoamperometry and Other Measurements for Rotating NEST Biosensors of the Present Inventions:

The bi-enzyme rotating disk electrodes containing NEST and tyrosinase were maintained at a potential of −100 mV (vs Ag/AgCl reference electrode) using a CHI 660B electrochemical analyzer (CH instruments, Austin, Tex.). Electrochemical measurements were performed a bi-enzyme rotating disk electrode (area=0.07 $cm^2$) dipped in 0.1 M phosphate buffer (pH 7.0), into which small aliquots of phenyl valerate, phenol or catechol solution were added. The steady state current was then measured at different rotating speeds. Ellipsometric measurements were done using a WVASE 32 (J.A. Woollam Co. Inc., Lincoln, Nebr.) ellipsometer. The angle of incidence was 75° for these experiments. The refractive indices of films were estimated to be n=1.5, k=0.

Validation of the Model.

The model was validated using NEST and tyrosinase containing bi-enzyme electrodes. Four electrodes (A, B, C and D) were used, and the steady state cathodic and anodic current sensitivities $S_{ct}^{c}$ and $S_{ct}^{a}$, were measured at two different catechol concentrations (3 and 5 μM), under varying electrode rotation speeds. Similarly the cathodic current sensitivities, $S_{ph}^{c}$ and $S_{pv}^{c}$, were also measured at different phenol (3 and 5 μM) and phenyl valerate concentrations (3 and 5 μM). While, the cathodic sensitivity, $S_{ct}^{c}$, remained practically constant with rotation rate, $S_{ph}^{c}$ and $S_{pv}^{c}$, decreased with rotation rate.

Figure 16:
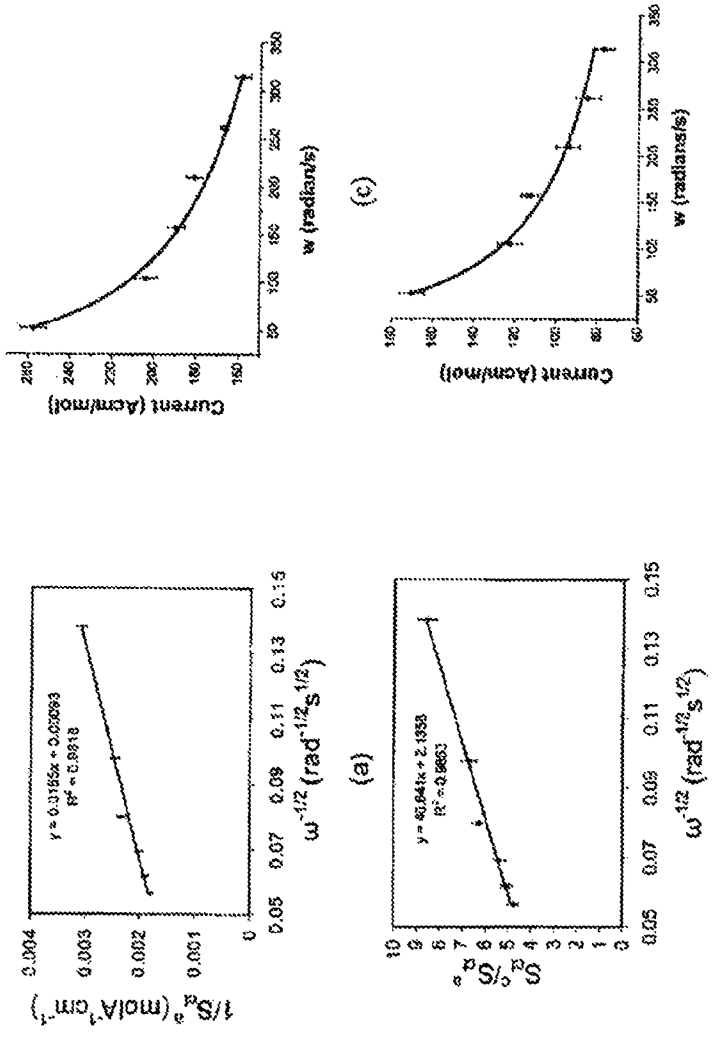
FIG. 16 shows exemplary reciprocal plots of $$1/S_{ct}^{a} \text{ and } \frac{S_{ct}^{c}}{S_{ct}^{a}}$$

FIG. 16 shows reciprocal plots of A)

$$S_{ct}^{a} \text{ and } B)\frac{S_{ct}^{c}}{S_{ct}^{a}}$$

versus the square root of rotation rate. Both plots, as predicted by the model (equations 1.32 and 1.33), showed linearity with correlation coefficients ($R^2$) greater than 0.98, suggesting that the model reasonably represent the electro-enzymatic processes occurring in the presence of catechol. From the slopes and intercepts of the fitted lines in FIGS. 3*a* and 3*b*, Equations 1.32 and 1.33 can be used to determine $\theta_3$=1.81 (±0.2), $P_m$=0.0091 (±0.0015) cm/s and $D_e$=2.2 (±1.2×$10^{-5}$) $cm^2$/s. Alternatively, $D_e$ can also be determined separately using Levich plot on a bare gold electrode. The obtained value of $D_e$ compares well with published values of $D_e$ for catechol (Coche-Guerente, et al. 1999; herein incorporated by reference).

FIG. 16C shows the current sensitivity to phenol as a function of electrode rotation speed. The sensitivity of the electrode was found to decrease with increasing rotation rates. In principle, Equation 1.28 could be fit to the data shown in FIGS. 16A and B and determine $\theta_2$, $P_m$ and $\theta_3$. The rotating disk electrode system used herein provides specific data points at six rotation speeds. To obtain more precise values of the parameters, the values of $P_m$ and $\theta_3$ were obtained with catechol present in the bulk solution, and Equation 1.28 was used fit to the data in FIG. 16 to give a best fit value of $\theta_2$=0.23 (±0.05).

FIG. 16D shows the current sensitivity to phenyl valerate as a function of electrode rotation speed. Like phenol, the sensitivity of the electrode to phenyl valerate decreased with increasing rotation rate. Equation 1.27 was fitted to the experimental data using the previously determined $P_m$. $\theta_2$ and $\theta_3$ parameters ($\theta_3$=1.81, $\theta_2$=0.23, $P_m$=0.0091 cm/s). A best fit value of $\theta_1$=1.1 (±0.25) was obtained.

In a summary of results, the average values of $P_m$, $\theta_1$, $\theta_2$ and $\theta_3$ yielded 0.0091 cm/s, 1.1, 0.23 and 1.81, respectively. The thickness of the interface (L) as measured using an ellipsometer was 25 nm. When the inventors contemplated a partition coefficient of $k_p$ as 1, then the value of $D_f$, using the relation, $$P_m = \frac{D_f k_p}{L},$$

was $2.27\times10^{-8}$ cm²/s. Although these calculations are approximate, they lead to the suggestion that the diffusion in the enzyme film is approximately 3 orders of magnitude slower than in bulk electrolyte. Similar effects were reported in layered polyelectrolyte films (Coche-Guerente, et al. 2001; herein incorporated by reference). In further theoretical computations, immobilized tyrosinase showed the same kinetic constants as in the homogeneous solution, where concentrations $[E_2]$ and $[E_3]$ of monophenolase and catecholase active sites were determined using the following relations:

$$(k_2/K_2)[E_2] = \frac{D_f\theta_2^2}{L^2} \quad (1.34)$$

$$(k_3/K_3)[E_3] = \frac{D_f\theta_3^2}{L^2} \quad (1.35)$$

Table 1.3 shows the calculated values of $[E_2]$ and $[E_3]$ along with the reported values of kinetic constants used to determine them (Coche-Guerente, et al. 2001; herein incorporated by reference). Although these calculations are coarse approximation, they suggest monophenolase active sites represent only 66% of the catecholase sites and about 40% of the total sites.

TABLE 1-3

Kinetic characteristics of tyrosinase immobilized in bi-enzyme electrode. Values of k and K were obtained from the literature them (Coche-Guerente, et al. 2001; herein incorporated by reference). However, enzyme concentration was calculated using equations 1.34 and 1.35.

| | Monophenolase activity | Catecholase activity |
|---|---|---|
| K (mol/cm³) | $(2.5 \pm 0.3)\times10^{-7}$ | $(2.2 \pm 0.2)\times10^{-7}$ |
| K ($s^{-1}$) | 20 ± 2 | 760 ± 30 |
| k/K ($mol^{-1}\,cm^3\,s^{-1}$) | $8.4\times10^{7}$ | $3.45\times10^{9}$ |
| Enzyme concentration (mol/cm³) | $2.29\times10^{-6}$ | $3.45\times10^{-6}$ |

Actual Experimental Information Using Biosensors of the Present Inventions Provided on Rotating Disk Electrodes and Using Rotating Disks During Measurements.

FIG. 17 show the simulated concentration profiles of phenyl valerate (A), phenol, catechol and o-quinone (collectively shown in B) normalized to a phenyl valerate bulk concentration ($S_1(\infty)$) as a function of relative position (x/L) within the interface. The concentration profile was simulated using equations 1.23-1.26, along with the experimentally determined values of different parameters ($P_m$=0.0091 cm/s, $\theta_1$=1.1, $\theta_2$=0.23, $\theta_3$=1.81, ω=500 rpm and $D_e=2.2\times10^{-5}$ cm²/s). As expected, the concentration of o-quinone, and the concentration gradients of phenyl valerate $$\left(\frac{\partial S_1}{\partial x}\right)$$

and phenol concentration $$\left(\frac{\partial S_2}{\partial x}\right),$$

at the electrode surface (x=0) were zero.

The model's predictions help explain the observed (FIG. 16 (D)) decrease in current with increasing rotation rates in the presence of phenyl valerate. The electrochemical transduction step regenerates catechol from o-quinone. A portion of the catechol is lost by diffusion through the stagnant film, and the remainder is oxidized to o-quinone, which increases the sensor's output. As the electrode rotation rate increases, the film mass transfer coefficient also increases and increasing fraction of the catechol is lost. As a consequence, less catechol is recycled to o-quinone, and the o-quinone concentration at the electrode is reduced, leading to lower sensitivity for phenyl valerate detection. Consistent with this mechanism, FIG. 17(C) shows that the predicted concentration gradient of o-quinone at x=0 decreases as the rotation rate increases.

FIG. 17 (D) shows the simulated current sensitivity, $S_{pv}^c$, as a function of amount of NEST esterase activity ($\theta_1$) and tyrosinase's catecholase activity ($\theta_3$), assuming $P_m$=0.0091 cm/s and ω=500 rpm. At low $\theta_1$ values, $S_{pv}^c$ increases as $\theta_1$ increases, indicating that the NEST activity is rate limiting. However, as $\theta_1$ increases, the $S_{pv}^c$ curve approaches an asymptote, indicating that the biosensor response is becoming limited by the catechol recycling ($\theta_3$). For a given, $\theta_1$, the current sensitivity $S_{pv}^c$ increases with $\theta_3$, because at higher values of catecholase activity enzymatic recycling of o-quinone becomes more and more efficient, leading to amplified responses or higher sensitivities.

Amplification factor (AF) can be defined as the ratio of current sensitivities in the presence ($S_{pv}^c$) and absence of catecholase activity ($S_{pv,\theta_3=0}^c$).

$$AF = \frac{S_{pv}^c}{S_{pv,\theta_3=0}^c} \quad (1.36)$$

The following relation for the AF can be derived from Equation 1.36 and 1.27. This equation shows that AF is a function of Thiele modulus $\theta_3$ and the ratio $$\frac{P_m}{m_e},$$

which is the reciprocal of Sherwood number.

$$AF = \left(1 + \frac{P_m}{m_e}\right)\theta_3\left(\frac{\frac{P_m}{m_e}\theta_3\sinh\theta_3 + \cosh\theta_3}{\frac{P_m}{m_e}\theta_3\cosh\theta_3 + \sinh\theta_3}\right) \quad (1.37)$$

FIG. 18 shows predicted AF values as a function of $\theta_3$, assuming experimentally realistic values of $P_m$=0.0091 cm/s and ω=500 rpm. Amplification increases with $\theta_3$ and, depending upon the rotation rate, amplification factors as high as 20 can be achieved. The mathematical model predicts about 2.5-fold signal amplification via recycling for our bi-enzyme electrode at a rotation speed of 500 rpm.

Collectively, the results of the experiments described herein present methods for optimization of bi-enzyme biosensors that involve substrate recycling, such as those provided in the present inventions. The results show strategies and methods for increasing biosensor sensitivity. When these methods were applied to NEST biosensors of the present inventions, a demonstration was provided for increasing the tyrosinase concentration while decreasing the mass transfer coefficient gave higher electrical signals (signal amplification) for a given NEST loading on the electrode. This result is particularly important to electrodes of the present inventions since tyrosinase is relatively inexpensive and commercially available, while NEST is not commercially available. Further NEST/NTE expression and purification requires special expertise.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention should not be unduly limited to such specific embodiments. Indeed, various modifications of the described modes for carrying out the invention which are obvious to those skilled in chemistry, medicine, diagnostics, molecular biology or related fields are intended to be within the scope of the present invention and the following Claims.

We claim:

1. A device, comprising: a linker attached to an electrode, said linker positioned between said electrode and an enzyme immobilizing layer, said layer interacting with an oxidase and a neuropathy target esterase.

2. The device of claim 1, wherein said enzyme immobilizing layer comprises a plurality of ammonium ions.

3. The device of claim 1, wherein said enzyme immobilizing layer comprises poly-L-lysine.

4. The device of claim 1, wherein said linker comprises thioctic acid.

5. The device of claim 1, wherein said oxidase is a tyrosinase.

6. The device of claim 1, wherein said electrode is an amperometric electrode.

7. The device of claim 1, wherein the neuropathy target esterase is an esterase domain of neuropathy target esterase (NEST).

8. A device, comprising: a linker attached to an electrode, said linker positioned between said electrode and a first enzyme immobilizing layer, said first layer interacting with an oxidase, said oxidase positioned between said first enzyme immobilizing layer and a second enzyme immobilizing layer, said second layer interacting with a neuropathy target esterase.

9. The device of claim 8, wherein said first and second enzyme immobilizing layers comprises a plurality of ammonium ions.

10. The device of claim 8, wherein said first and second layers comprises poly-L-lysine.

11. The device of claim 8, wherein said linker comprises thioctic acid.

12. The device of claim 8, wherein said oxidase is a tyrosinase.

13. The device of claim 8, wherein said electrode is an amperometric electrode.

14. The device of claim 8, wherein the neuropathy target esterase is an esterase domain of neuropathy target esterase (NEST).

15. A method, comprising, a) providing, i) a device, comprising: a linker attached to an electrode, said linker positioned between said electrode and an enzyme immobilizing layer, said layer interacting with an oxidase and a neuropathy target esterase;

ii) a substrate, and b) contacting said device with said substrate; and c) measuring enzyme activity.

16. The method of claim 15, wherein said substrate is an esterase substrate.

17. The method of claim 16, wherein said substrate is in solution.

18. The method of claim 17, wherein said enzyme activity measured in step c) is esterase activity.

19. The method of claim 18, wherein said substrate is phenyl valerate.

20. The method of claim 18, wherein said enzyme activity measured in step c) is measured in real-time.

21. The method of claim 15, wherein the neuropathy target esterase is an esterase domain of neuropathy target esterase (NEST).

* * * * *

SEQUENCE LISTING

```
<160> NUMBER OF SEQ ID NOS: 5

<210> SEQ ID NO 1
<211> LENGTH: 1470
<212> TYPE: DNA
<213> ORGANISM: Homo sapiens

<400> SEQUENCE: 1

ctcaccaacc cagccagcaa cctggcaact gtggcaatcc tgcctgtgtg tgctgaggtc     60

cccatggtgg ccttcacgct ggagctgcag cacgccctgc aggccatcgg tccgacgcta    120

ctccttaaca gtgacatcat ccgggcacgc ctgggggcct ccgcactgga tagcatccaa    180

gagttccggc tgtcagggtg gctggcccag caggaggatg cacaccgtat cgtactctac    240

cagacggacg cctcgctgac gccctggacc gtgcgctgcc tgcgacaggc cgactgcatc    300

ctcattgtgg gcctggggga ccaggagcct accctcggcc agctggagca gatgctggag    360

aacacggctg tgcgcgccct taagcagcta gtcctgctcc accgagagga gggtgcgggc    420

cccacgcgca ccgtggagtg gctaaatatg cgcagctggt gctcggggca cctgcacctg    480

cgctgtccgc gccgcctctt ttcgcgccgc agccctgcca agctgcatga gctctacgag    540

aaggttttct ccaggcgcgc ggaccggcac agcgacttct cccgcttggc gagggtgctc    600

acggggaaca ccattgccct tgtgctaggc gggggcgggg ccaggggctg ctcgcacatc    660

ggagtactaa aggcattaga ggaggcgggg gtccccgtgg acctggtggg cggcacgtcc    720

attggctctt tcatcggagc gttgtacgcg gaggagcgca gcgccagccg cacgaagcag    780

cgggcccggg agtgggccaa gagcatgact tcggtgctgg aacctgtgtt ggacctcacg    840

tacccagtca cctccatgtt cactgggtct gcctttaacc gcagcatcca tcgggtcttc    900

caggataagc agattgagga cctgtggctg ccttacttca acgtgaccac agatatcacc    960

gcctcagcca tgcgagtcca caaagatggc tccctgtggc ggtacgtgcg cgccagcatg   1020

acgctgtcgg gctacctgcc cccgctgtgc gaccccaagg acgggcacct actcatggat   1080

ggcggctaca tcaacaatct gccagcggac atcgcccgca gcatgggtgc caaaacggtc   1140

atcgccattg acgtggggag ccaggatgag acggacctca gcacctacgg ggacagcctg   1200

tccggctggt ggctgctgtg gaagcggctg aatccctggg ctgacaaggt aaaggttcca   1260

gacatggctg aaatccagtc ccgcctggcc tacgtgtcct gtgtgcggca gctagaggtt   1320

gtcaagtcca gctcctactg cgagtacctg cgcccgccca tcgactgctt caagaccatg   1380
```

gactttggga agttcgacca gatctatgat gtgggctacc agtacgggaa ggcggtgttt 1440
ggaggctgga gccgtggcaa cgtcattgag 1470

<210> SEQ ID NO 2
<211> LENGTH: 490
<212> TYPE: PRT
<213> ORGANISM: Homo sapiens

<400> SEQUENCE: 2

Leu Thr Asn Pro Ala Ser Asn Leu Ala Thr Val Ala Ile Leu Pro Val
1 5 10 15

Cys Ala Glu Val Pro Met Val Ala Phe Thr Leu Glu Leu Gln His Ala
20 25 30

Leu Gln Ala Ile Gly Pro Thr Leu Leu Leu Asn Ser Asp Ile Ile Arg
35 40 45

Ala Arg Leu Gly Ala Ser Ala Leu Asp Ser Ile Gln Glu Phe Arg Leu
50 55 60

Ser Gly Trp Leu Ala Gln Gln Glu Asp Ala His Arg Ile Val Leu Tyr
65 70 75 80

Gln Thr Asp Ala Ser Leu Thr Pro Trp Thr Val Arg Cys Leu Arg Gln
85 90 95

Ala Asp Cys Ile Leu Ile Val Gly Leu Gly Asp Gln Glu Pro Thr Leu
100 105 110

Gly Gln Leu Glu Gln Met Leu Glu Asn Thr Ala Val Arg Ala Leu Lys
115 120 125

Gln Leu Val Leu Leu His Arg Glu Glu Gly Ala Gly Pro Thr Arg Thr
130 135 140

Val Glu Trp Leu Asn Met Arg Ser Trp Cys Ser Gly His Leu His Leu
145 150 155 160

Arg Cys Pro Arg Arg Leu Phe Ser Arg Arg Ser Pro Ala Lys Leu His
165 170 175

Glu Leu Tyr Glu Lys Val Phe Ser Arg Arg Ala Asp Arg His Ser Asp
180 185 190

Phe Ser Arg Leu Ala Arg Val Leu Thr Gly Asn Thr Ile Ala Leu Val
195 200 205

Leu Gly Gly Gly Gly Ala Arg Gly Cys Ser His Ile Gly Val Leu Lys
210 215 220

Ala Leu Glu Glu Ala Gly Val Pro Val Asp Leu Val Gly Gly Thr Ser
225 230 235 240

Ile Gly Ser Phe Ile Gly Ala Leu Tyr Ala Glu Glu Arg Ser Ala Ser
245 250 255

Arg Thr Lys Gln Arg Ala Arg Glu Trp Ala Lys Ser Met Thr Ser Val
260 265 270

Leu Glu Pro Val Leu Asp Leu Thr Tyr Pro Val Thr Ser Met Phe Thr
275 280 285

Gly Ser Ala Phe Asn Arg Ser Ile His Arg Val Phe Gln Asp Lys Gln
290 295 300

Ile Glu Asp Leu Trp Leu Pro Tyr Phe Asn Val Thr Thr Asp Ile Thr
305 310 315 320

Ala Ser Ala Met Arg Val His Lys Asp Gly Ser Leu Trp Arg Tyr Val
325 330 335

Arg Ala Ser Met Thr Leu Ser Gly Tyr Leu Pro Pro Leu Cys Asp Pro
340 345 350

Lys Asp Gly His Leu Leu Met Asp Gly Gly Tyr Ile Asn Asn Leu Pro
355 360 365

-continued

```
Ala Asp Ile Ala Arg Ser Met Gly Ala Lys Thr Val Ile Ala Ile Asp
    370                 375                 380

Val Gly Ser Gln Asp Glu Thr Asp Leu Ser Thr Tyr Gly Asp Ser Leu
385                 390                 395                 400

Ser Gly Trp Trp Leu Leu Trp Lys Arg Leu Asn Pro Trp Ala Asp Lys
                405                 410                 415

Val Lys Val Pro Asp Met Ala Glu Ile Gln Ser Arg Leu Ala Tyr Val
            420                 425                 430

Ser Cys Val Arg Gln Leu Glu Val Val Lys Ser Ser Ser Tyr Cys Glu
        435                 440                 445

Tyr Leu Arg Pro Pro Ile Asp Cys Phe Lys Thr Met Asp Phe Gly Lys
    450                 455                 460

Phe Asp Gln Ile Tyr Asp Val Gly Tyr Gln Tyr Gly Lys Ala Val Phe
465                 470                 475                 480

Gly Gly Trp Ser Arg Gly Asn Val Ile Glu
                485                 490


<210> SEQ ID NO 3
<211> LENGTH: 3981
<212> TYPE: DNA
<213> ORGANISM: Homo sapiens

<400> SEQUENCE: 3

atggaggctc cgctgcaaac tggaatggtg cttggcgtga tgatcggggc cggagtggcg      60

gtggtggtca cggccgtgct catcctcctg gtggtgcgga ggctgcgagt gccaaaaacc     120

ccagccccgg atggcccccg gtatcggttc cggaagaggg acaaagtgct cttctatggc     180

cggaagatta tgcggaaggt gtcacaatcc acctcctccc tcgtggatac ctctgtctcc     240

gccacctccc ggccacgcat gaggaagaaa ctgaagatgc tcaacattgc caagaagatc     300

ctgcgcatcc agaaagagac gcccacgctg cagcggaagg agcccccgcc cgcagtgcta     360

gaagctgacc tgaccgaggg cgacctggct aactcccatc tgccctctga agtgctttat     420

atgctcaaga acgtccgggt gctgggccac ttcgagaagc cactcttcct ggagctctgc     480

cgccacatgg tcttccagcg gctgggccag ggtgactacg tcttccggcc gggccagcca     540

gatgccagca tctacgtggt gcaggacggg ctgctggagc tctgtctgcc agggcctgac     600

gggaaggagt gtgtggtgaa ggaagtggtt cctggggaca gcgtcaacag ccttctcagc     660

atcctggatg tcatcaccgg tcaccagcat ccccagcgga ccgtgtctgc ccgggcggcc     720

cgggactcca cggtgctgcg cctgccggtg gaagcattct ccgcggtctt caccaagtac     780

ccggagagct tggtgcgggt cgtgcagatc atcatggtgc ggctgcagcg agtcaccttc     840

ctggcactgc acaactacct gggtctgacc aatgagctct tcagccacga gatccagccc     900

ctgcgtctgt tccccagccc cggcctccca actcgcacca gccctgtgcg gggctccaag     960

agaatggtca gcacctcagc tacagacgag cccagggaga ccccagggcg gccacccgat    1020

cccaccgggg ccccgctgcc tggacctaca ggggaccctg tgaagcccac atccctggaa    1080

accccctcgg cccctctgct gagccgctgc gtctccatgc caggggacat ctcaggcttg    1140

cagggtggcc cccgctccga cttcgacatg gcctatgagc gtggccggat ctccgtgtcc    1200

ctgcaggaag aggcctccgg ggggtccctg gcagcccccg ctcggacccc cactcaggag    1260

cctcgtgagc agccggcagg cgcctgtgaa tacagctact gtgaggatga gtcggccact    1320

ggtggctgcc ctttcgggcc ctaccagggc cgccagacca gcagcatctt cgaggcagca    1380

aagcaggagc tggccaagct gatgcggatt gaggacccct ccctcctgaa cagcagagtc    1440
```

-continued

```
ttgctgcacc acgccaaagc tggcaccatc attgcccgcc agggagacca ggacgtgagc   1500
ctgcacttcg tgctctgggg ctgcctgcac gtgtaccagc gcatgatcga caaggcggag   1560
gacgtgtgcc tgttcgtagc gcagcccggg gaactggtgg ggcagctggc ggtgctcact   1620
ggcgaacctc tcatcttcac actgcgagcc caacgcgact gcaccttcct gcggatctcc   1680
aagtccgact tctatgagat catgcgcgca cagcccagtg tggtgctgag tgcggcgcac   1740
acggtggcag ccaggatgtc gcccttcgtg cgccagatgg acttcgccat cgactggact   1800
gcagtggagg cgggacgcgc gctgtacagg cagggcgacc gctccgactg cacttacatc   1860
gtgctcaatg ggcggctgcg tagcgtgatc cagcgaggca gtggcaagaa ggagctggtg   1920
ggcgagtacg gccgcggcga cctcatcggc gtggtggagg cactgacccg gcagccgcga   1980
gccacgacgg tgcacgcggt gcgcgacacg gagctagcca agcttcccga gggcaccttg   2040
ggtcacatca aacgccggta cccgcaggtc gtgacccgcc ttatccacct actgagccag   2100
aaaattctag ggaatttgca gcagctgcaa ggacccttcc cagcaggctc tgggttgggt   2160
gtgcccccac actcggaact caccaaccca gccagcaacc tggcaactgt ggcaatcctg   2220
cctgtgtgtg ctgaggtccc catggtggcc ttcacgctgg agctgcagca cgccctgcag   2280
gccatcggtc cgacgctact ccttaacagt gacatcatcc gggcacgcct gggggcctcc   2340
gcactggata gcatccaaga gttccggctg tcagggtggc tggcccagca ggaggatgca   2400
caccgtatcg tactctacca gacggacgcc tcgctgacgc cctggaccgt gcgctgcctg   2460
cgacaggccg actgcatcct cattgtgggc ctgggggacc aggagcctac cctcggccag   2520
ctggagcaga tgctggagaa cacggctgtg cgcgccctta agcagctagt cctgctccac   2580
cgagaggagg gtgcgggccc cacgcgcacc gtggagtggc taaatatgcg cagctggtgc   2640
tcggggcacc tgcacctgcg ctgtccgcgc cgcctctttt cgcgccgcag ccctgccaag   2700
ctgcatgagc tctacgagaa ggttttctcc aggcgcgcgg accggcacag cgacttctcc   2760
cgcttggcga gggtgctcac ggggaacacc attgcccttg tgctaggcgg gggcggggcc   2820
aggggctgct cgcacatcgg agtactaaag gcattagagg aggcgggggt ccccgtggac   2880
ctggtgggcg gcacgtccat tggctctttc atcggagcgt tgtacgcgga ggagcgcagc   2940
gccagccgca cgaagcagcg ggcccgggag tgggccaaga gcatgacttc ggtgctggaa   3000
cctgtgttgg acctcacgta cccagtcacc tccatgttca ctgggtctgc ctttaaccgc   3060
agcatccatc gggtcttcca ggataagcag attgaggacc tgtggctgcc ttacttcaac   3120
gtgaccacag atatcaccgc ctcagccatg cgagtccaca aagatggctc cctgtggcgg   3180
tacgtgcgcg ccagcatgac gctgtcgggc tacctgcccc cgctgtgcga ccccaaggac   3240
gggcacctac tcatggatgg cggctacatc aacaatctgc cagcggacat cgcccgcagc   3300
atgggtgcca aaacggtcat cgccattgac gtggggagcc aggatgagac ggacctcagc   3360
acctacgggg acagcctgtc cggctggtgg ctgctgtgga agcggctgaa tccctgggct   3420
gacaaggtaa aggttccaga catggctgaa atccagtccc gcctggccta cgtgtcctgt   3480
gtgcggcagc tagaggttgt caagtccagc tcctactgcg agtacctgcg cccgcccatc   3540
gactgcttca agaccatgga ctttgggaag ttcgaccaga tctatgatgt gggctaccag   3600
tacgggaagg cggtgtttgg aggctggagc cgtggcaacg tcattgagaa aatgctcaca   3660
gaccggcggt ctacagacct taatgagagc cgccgtgcag acgtgcttgc cttcccaagc   3720
tctggcttca ctgacttggc agagattgtg tcccggattg agccccccac gagctatgtc   3780
tctgatggct gtgctgacgg agaggagtca gattgtctga cagagtatga ggaggacgcc   3840
```

-continued ggacccgact gctcgaggga tgaagggggg tcccccgagg gcgcaagtcc cagcactgcc 3900
tccgagatgg aggaggagaa gtcgattctc cggcaacgac gctgtctgcc ccaggagccg 3960
cccggctcag ccacagatgc c 3981

<210> SEQ ID NO 4
<211> LENGTH: 1327
<212> TYPE: PRT
<213> ORGANISM: Homo sapiens

<400> SEQUENCE: 4

Met Glu Ala Pro Leu Gln Thr Gly Met Val Leu Gly Val Met Ile Gly
1 5 10 15

Ala Gly Val Ala Val Val Val Thr Ala Val Leu Ile Leu Leu Val Val
20 25 30

Arg Arg Leu Arg Val Pro Lys Thr Pro Ala Pro Asp Gly Pro Arg Tyr
35 40 45

Arg Phe Arg Lys Arg Asp Lys Val Leu Phe Tyr Gly Arg Lys Ile Met
50 55 60

Arg Lys Val Ser Gln Ser Thr Ser Ser Leu Val Asp Thr Ser Val Ser
65 70 75 80

Ala Thr Ser Arg Pro Arg Met Arg Lys Lys Leu Lys Met Leu Asn Ile
85 90 95

Ala Lys Lys Ile Leu Arg Ile Gln Lys Glu Thr Pro Thr Leu Gln Arg
100 105 110

Lys Glu Pro Pro Pro Ala Val Leu Glu Ala Asp Leu Thr Glu Gly Asp
115 120 125

Leu Ala Asn Ser His Leu Pro Ser Glu Val Leu Tyr Met Leu Lys Asn
130 135 140

Val Arg Val Leu Gly His Phe Glu Lys Pro Leu Phe Leu Glu Leu Cys
145 150 155 160

Arg His Met Val Phe Gln Arg Leu Gly Gln Gly Asp Tyr Val Phe Arg
165 170 175

Pro Gly Gln Pro Asp Ala Ser Ile Tyr Val Val Gln Asp Gly Leu Leu
180 185 190

Glu Leu Cys Leu Pro Gly Pro Asp Gly Lys Glu Cys Val Val Lys Glu
195 200 205

Val Val Pro Gly Asp Ser Val Asn Ser Leu Leu Ser Ile Leu Asp Val
210 215 220

Ile Thr Gly His Gln His Pro Gln Arg Thr Val Ser Ala Arg Ala Ala
225 230 235 240

Arg Asp Ser Thr Val Leu Arg Leu Pro Val Glu Ala Phe Ser Ala Val
245 250 255

Phe Thr Lys Tyr Pro Glu Ser Leu Val Arg Val Val Gln Ile Ile Met
260 265 270

Val Arg Leu Gln Arg Val Thr Phe Leu Ala Leu His Asn Tyr Leu Gly
275 280 285

Leu Thr Asn Glu Leu Phe Ser His Glu Ile Gln Pro Leu Arg Leu Phe
290 295 300

Pro Ser Pro Gly Leu Pro Thr Arg Thr Ser Pro Val Arg Gly Ser Lys
305 310 315 320

Arg Met Val Ser Thr Ser Ala Thr Asp Glu Pro Arg Glu Thr Pro Gly
325 330 335

Arg Pro Pro Asp Pro Thr Gly Ala Pro Leu Pro Gly Pro Thr Gly Asp
340 345 350

-continued

```
Pro Val Lys Pro Thr Ser Leu Glu Thr Pro Ser Ala Pro Leu Leu Ser
        355                 360                 365

Arg Cys Val Ser Met Pro Gly Asp Ile Ser Gly Leu Gln Gly Gly Pro
    370                 375                 380

Arg Ser Asp Phe Asp Met Ala Tyr Glu Arg Gly Arg Ile Ser Val Ser
385                 390                 395                 400

Leu Gln Glu Glu Ala Ser Gly Gly Ser Leu Ala Ala Pro Ala Arg Thr
                405                 410                 415

Pro Thr Gln Glu Pro Arg Glu Gln Pro Ala Gly Ala Cys Glu Tyr Ser
            420                 425                 430

Tyr Cys Glu Asp Glu Ser Ala Thr Gly Gly Cys Pro Phe Gly Pro Tyr
        435                 440                 445

Gln Gly Arg Gln Thr Ser Ser Ile Phe Glu Ala Ala Lys Gln Glu Leu
    450                 455                 460

Ala Lys Leu Met Arg Ile Glu Asp Pro Ser Leu Leu Asn Ser Arg Val
465                 470                 475                 480

Leu Leu His His Ala Lys Ala Gly Thr Ile Ile Ala Arg Gln Gly Asp
                485                 490                 495

Gln Asp Val Ser Leu His Phe Val Leu Trp Gly Cys Leu His Val Tyr
            500                 505                 510

Gln Arg Met Ile Asp Lys Ala Glu Asp Val Cys Leu Phe Val Ala Gln
        515                 520                 525

Pro Gly Glu Leu Val Gly Gln Leu Ala Val Leu Thr Gly Glu Pro Leu
    530                 535                 540

Ile Phe Thr Leu Arg Ala Gln Arg Asp Cys Thr Phe Leu Arg Ile Ser
545                 550                 555                 560

Lys Ser Asp Phe Tyr Glu Ile Met Arg Ala Gln Pro Ser Val Val Leu
                565                 570                 575

Ser Ala Ala His Thr Val Ala Ala Arg Met Ser Pro Phe Val Arg Gln
            580                 585                 590

Met Asp Phe Ala Ile Asp Trp Thr Ala Val Glu Ala Gly Arg Ala Leu
        595                 600                 605

Tyr Arg Gln Gly Asp Arg Ser Asp Cys Thr Tyr Ile Val Leu Asn Gly
    610                 615                 620

Arg Leu Arg Ser Val Ile Gln Arg Gly Ser Gly Lys Lys Glu Leu Val
625                 630                 635                 640

Gly Glu Tyr Gly Arg Gly Asp Leu Ile Gly Val Val Glu Ala Leu Thr
                645                 650                 655

Arg Gln Pro Arg Ala Thr Thr Val His Ala Val Arg Asp Thr Glu Leu
            660                 665                 670

Ala Lys Leu Pro Glu Gly Thr Leu Gly His Ile Lys Arg Arg Tyr Pro
        675                 680                 685

Gln Val Val Thr Arg Leu Ile His Leu Leu Ser Gln Lys Ile Leu Gly
    690                 695                 700

Asn Leu Gln Gln Leu Gln Gly Pro Phe Pro Ala Gly Ser Gly Leu Gly
705                 710                 715                 720

Val Pro Pro His Ser Glu Leu Thr Asn Pro Ala Ser Asn Leu Ala Thr
                725                 730                 735

Val Ala Ile Leu Pro Val Cys Ala Glu Val Pro Met Val Ala Phe Thr
            740                 745                 750

Leu Glu Leu Gln His Ala Leu Gln Ala Ile Gly Pro Thr Leu Leu Leu
        755                 760                 765

Asn Ser Asp Ile Ile Arg Ala Arg Leu Gly Ala Ser Ala Leu Asp Ser
```

-continued

```
        770                 775                 780

Ile Gln Glu Phe Arg Leu Ser Gly Trp Leu Ala Gln Gln Glu Asp Ala
785                 790                 795                 800

His Arg Ile Val Leu Tyr Gln Thr Asp Ala Ser Leu Thr Pro Trp Thr
                805                 810                 815

Val Arg Cys Leu Arg Gln Ala Asp Cys Ile Leu Ile Val Gly Leu Gly
            820                 825                 830

Asp Gln Glu Pro Thr Leu Gly Gln Leu Glu Gln Met Leu Glu Asn Thr
        835                 840                 845

Ala Val Arg Ala Leu Lys Gln Leu Val Leu Leu His Arg Glu Glu Gly
    850                 855                 860

Ala Gly Pro Thr Arg Thr Val Glu Trp Leu Asn Met Arg Ser Trp Cys
865                 870                 875                 880

Ser Gly His Leu His Leu Arg Cys Pro Arg Arg Leu Phe Ser Arg Arg
                885                 890                 895

Ser Pro Ala Lys Leu His Glu Leu Tyr Glu Lys Val Phe Ser Arg Arg
            900                 905                 910

Ala Asp Arg His Ser Asp Phe Ser Arg Leu Ala Arg Val Leu Thr Gly
        915                 920                 925

Asn Thr Ile Ala Leu Val Leu Gly Gly Gly Gly Ala Arg Gly Cys Ser
    930                 935                 940

His Ile Gly Val Leu Lys Ala Leu Glu Glu Ala Gly Val Pro Val Asp
945                 950                 955                 960

Leu Val Gly Gly Thr Ser Ile Gly Ser Phe Ile Gly Ala Leu Tyr Ala
                965                 970                 975

Glu Glu Arg Ser Ala Ser Arg Thr Lys Gln Arg Ala Arg Glu Trp Ala
            980                 985                 990

Lys Ser Met Thr Ser Val Leu Glu  Pro Val Leu Asp Leu  Thr Tyr Pro
        995                 1000                1005

Val Thr  Ser Met Phe Thr Gly  Ser Ala Phe Asn Arg  Ser Ile His
    1010                1015                1020

Arg Val  Phe Gln Asp Lys Gln  Ile Glu Asp Leu Trp  Leu Pro Tyr
    1025                1030                1035

Phe Asn  Val Thr Thr Asp Ile  Thr Ala Ser Ala Met  Arg Val His
    1040                1045                1050

Lys Asp  Gly Ser Leu Trp Arg  Tyr Val Arg Ala Ser  Met Thr Leu
    1055                1060                1065

Ser Gly  Tyr Leu Pro Pro Leu  Cys Asp Pro Lys Asp  Gly His Leu
    1070                1075                1080

Leu Met  Asp Gly Gly Tyr Ile  Asn Asn Leu Pro Ala  Asp Ile Ala
    1085                1090                1095

Arg Ser  Met Gly Ala Lys Thr  Val Ile Ala Ile Asp  Val Gly Ser
    1100                1105                1110

Gln Asp  Glu Thr Asp Leu Ser  Thr Tyr Gly Asp Ser  Leu Ser Gly
    1115                1120                1125

Trp Trp  Leu Leu Trp Lys Arg  Leu Asn Pro Trp Ala  Asp Lys Val
    1130                1135                1140

Lys Val  Pro Asp Met Ala Glu  Ile Gln Ser Arg Leu  Ala Tyr Val
    1145                1150                1155

Ser Cys  Val Arg Gln Leu Glu  Val Val Lys Ser Ser  Ser Tyr Cys
    1160                1165                1170

Glu Tyr  Leu Arg Pro Pro Ile  Asp Cys Phe Lys Thr  Met Asp Phe
    1175                1180                1185
```

-continued

```
Gly Lys  Phe Asp Gln Ile Tyr  Asp Val Gly Tyr Gln  Tyr Gly Lys
    1190                 1195                 1200

Ala Val  Phe Gly Gly Trp Ser  Arg Gly Asn Val Ile  Glu Lys Met
    1205                 1210                 1215

Leu Thr  Asp Arg Arg Ser Thr  Asp Leu Asn Glu Ser  Arg Arg Ala
    1220                 1225                 1230

Asp Val  Leu Ala Phe Pro Ser  Ser Gly Phe Thr Asp  Leu Ala Glu
    1235                 1240                 1245

Ile Val  Ser Arg Ile Glu Pro  Pro Thr Ser Tyr Val  Ser Asp Gly
    1250                 1255                 1260

Cys Ala  Asp Gly Glu Glu Ser  Asp Cys Leu Thr Glu  Tyr Glu Glu
    1265                 1270                 1275

Asp Ala  Gly Pro Asp Cys Ser  Arg Asp Glu Gly Gly  Ser Pro Glu
    1280                 1285                 1290

Gly Ala  Ser Pro Ser Thr Ala  Ser Glu Met Glu Glu  Glu Lys Ser
    1295                 1300                 1305

Ile Leu  Arg Gln Arg Arg Cys  Leu Pro Gln Glu Pro  Pro Gly Ser
    1310                 1315                 1320

Ala Thr  Asp Ala
    1325
```

<210> SEQ ID NO 5
<211> LENGTH: 4391
<212> TYPE: DNA
<213> ORGANISM: Homo sapiens

<400> SEQUENCE: 5

```
ccccacgcca ccccaagcat cccaggactc ttctgaaaca gggcagtgac ccgggaggaa     60

gtcaccaggt gcagaggacc gtgccctgtg gggacctgcc tgcaggctgc tgacagactc    120

cgggctacca gatcggccgt ccagctggaa tcaaccgatg gaggctccgc tgcaaactgg    180

aatggtgctt ggcgtgatga tcggggccgg agtggcggtg gtggtcacgg ccgtgctcat    240

cctcctggtg gtgcggaggc tgcgagtgcc aaaaacccca gccccggatg gcccccggta    300

tcggttccgg aagagggaca aagtgctctt ctatggccgg aagattatgc ggaaggtgtc    360

acaatccacc tcctccctcg tggatacctc tgtctccgcc acctcccggc cacgcatgag    420

gaagaaactg aagatgctca acattgccaa gaagatcctg cgcatccaga aagagacgcc    480

cacgctgcag cggaaggagc ccccgcccgc agtgctagaa gctgacctga ccgagggcga    540

cctggctaac tcccatctgc cctctgaagt gctttatatg ctcaagaacg tccgggtgct    600

gggccacttc gagaagccac tcttcctgga gctctgccgc cacatggtct tccagcggct    660

gggccagggt gactacgtct tccggccggg ccagccagat gccagcatct acgtggtgca    720

ggacgggctg ctggagctct gtctgccagg gcctgacggg aaggagtgtg tggtgaagga    780

agtggttcct ggggacagcg tcaacagcct tctcagcatc ctggatgtca tcaccggtca    840

ccagcatccc cagcggaccg tgtctgcccg ggcggcccgg gactccacgg tgctgcgcct    900

gccggtggaa gcattctccg cggtcttcac caagtacccg gagagcttgg tgcgggtcgt    960

gcagatcatc atggtgcggc tgcagcgagt caccttcctg gcactgcaca actacctggg   1020

tctgaccaat gagctcttca gccacgagat ccagcccctg cgtctgttcc ccagccccgg   1080

cctcccaact cgcaccagcc ctgtgcgggg ctccaagaga atggtcagca cctcagctac   1140

agacgagccc agggagaccc cagggcggcc acccgatccc accggggccc cgctgcctgg   1200

acctacaggg gaccctgtga agcccacatc cctggaaacc ccctcggccc ctctgctgag   1260
```

-continued

```
ccgctgcgtc tccatgccag gggacatctc aggcttgcag ggtggccccc gctccgactt   1320
cgacatggcc tatgagcgtg gccggatctc cgtgtccctg caggaagagg cctccggggg   1380
gtccctggca gcccccgctc ggacccccac tcaggagcct cgtgagcagc cggcaggcgc   1440
ctgtgaatac agctactgtg aggatgagtc ggccactggt ggctgccctt tcgggcccta   1500
ccagggccgc cagaccagca gcatcttcga ggcagcaaag caggagctgg ccaagctgat   1560
gcggattgag gacccctccc tcctgaacag cagagtcttg ctgcaccacg ccaaagctgg   1620
caccatcatt gcccgccagg gagaccagga cgtgagcctg cacttcgtgc tctggggctg   1680
cctgcacgtg taccagcgca tgatcgacaa ggcggaggac gtgtgcctgt tcgtagcgca   1740
gcccggggaa ctggtggggc agctggcggt gctcactggc gaacctctca tcttcacact   1800
gcgagcccaa cgcgactgca ccttcctgcg gatctccaag tccgacttct atgagatcat   1860
gcgcgcacag cccagtgtgg tgctgagtgc ggcgcacacg gtggcagcca ggatgtcgcc   1920
cttcgtgcgc cagatggact tcgccatcga ctggactgca gtggaggcgg gacgcgcgct   1980
gtacaggcag ggcgaccgct ccgactgcac ttacatcgtg ctcaatgggc ggctgcgtag   2040
cgtgatccag cgaggcagtg gcaagaagga gctggtgggc gagtacggcc gcggcgacct   2100
catcggcgtg gtggaggcac tgacccggca gccgcgagcc acgacggtgc acgcggtgcg   2160
cgacacggag ctagccaagc ttcccgaggg caccttgggt cacatcaaac gccggtaccc   2220
gcaggtcgtg acccgcctta tccacctact gagccagaaa attctaggga atttgcagca   2280
gctgcaagga cccttcccag caggctctgg gttgggtgtg cccccacact cggaactcac   2340
caacccagcc agcaacctgg caactgtggc aatcctgcct gtgtgtgctg aggtccccat   2400
ggtggccttc acgctggagc tgcagcacgc cctgcaggcc atcggtccga cgctactcct   2460
taacagtgac atcatccggg cacgcctggg ggcctccgca ctggatagca tccaagagtt   2520
ccggctgtca gggtggctgg cccagcagga ggatgcacac cgtatcgtac tctaccagac   2580
ggacgcctcg ctgacgccct ggaccgtgcg ctgcctgcga caggccgact gcatcctcat   2640
tgtgggcctg gggaccagg agcctaccct cggccagctg gagcagatgc tggagaacac    2700
ggctgtgcgc gcccttaagc agctagtcct gctccaccga gaggagggtg cgggccccac   2760
gcgcaccgtg gagtggctaa atatgcgcag ctggtgctcg gggcacctgc acctgcgctg   2820
tccgcgccgc ctcttttcgc gccgcagccc tgccaagctg catgagctct acgagaaggt   2880
tttctccagg cgcgcggacc ggcacagcga cttctcccgc ttggcgaggg tgctcacggg   2940
gaacaccatt gcccttgtgc taggcggggg cggggccagg ggctgctcgc acatcggagt   3000
actaaaggca ttagaggagg cgggggtccc cgtggacctg gtgggcggca cgtccattgg   3060
ctctttcatc ggagcgttgt acgcggagga gcgcagcgcc agccgcacga agcagcgggc   3120
ccgggagtgg gccaagagca tgacttcggt gctggaacct gtgttggacc tcacgtaccc   3180
agtcacctcc atgttcactg ggtctgcctt taaccgcagc atccatcggg tcttccagga   3240
taagcagatt gaggacctgt ggctgcctta cttcaacgtg accacagata tcaccgcctc   3300
agccatgcga gtccacaaag atggctccct gtggcggtac gtgcgcgcca gcatgacgct   3360
gtcgggctac ctgcccccgc tgtgcgaccc caaggacggg cacctactca tggatggcgg   3420
ctacatcaac aatctgccag cggacatcgc ccgcagcatg ggtgccaaaa cggtcatcgc   3480
cattgacgtg gggagccagg atgagacgga cctcagcacc tacggggaca gcctgtccgg   3540
ctggtggctg ctgtggaagc ggctgaatcc ctgggctgac aaggtaaagg ttccagacat   3600
ggctgaaatc cagtcccgcc tggcctacgt gtcctgtgtg cggcagctag aggttgtcaa   3660
```

-continued

| | |
|---|---|
| gtccagctcc tactgcgagt acctgcgccc gcccatcgac tgcttcaaga ccatggactt | 3720 |
| tgggaagttc gaccagatct atgatgtggg ctaccagtac gggaaggcgg tgtttggagg | 3780 |
| ctggagccgt ggcaacgtca ttgagaaaat gctcacagac cggcggtcta cagaccttaa | 3840 |
| tgagagccgc cgtgcagacg tgcttgcctt cccaagctct ggcttcactg acttggcaga | 3900 |
| gattgtgtcc cggattgagc cccccacgag ctatgtctct gatggctgtg ctgacggaga | 3960 |
| ggagtcagat tgtctgacag agtatgagga ggacgccgga cccgactgct cgagggatga | 4020 |
| aggggggtcc cccgagggcg caagtcccag cactgcctcc gagatggagg aggagaagtc | 4080 |
| gattctccgg caacgacgct gtctgcccca ggagccgccc ggctcagcca cagatgcctg | 4140 |
| aggacctcga caggggtcac cccctccctc ccacccctgg actgggctgg gggtggcccc | 4200 |
| gtgggggtag ctcactcccc ctcctgctgc tatgcctgtg acccccgcgg cccacacact | 4260 |
| ggactgacct gccctgagcg gggatgcagt gttgcactga tgacttgacc agcccctccc | 4320 |
| ccaataaact cgcctcttgg aaaaaaaaaa aaaaaaaaaa aaaaaaaaaa aaaaaaaaaa | 4380 |
| aaaaaaaaaa a | 4391 |